US005578448A

United States Patent [19]
Rota et al.

[11] Patent Number: 5,578,448
[45] Date of Patent: Nov. 26, 1996

[54] NUCLEIC ACIDS ENCODING WILD-TYPE MEASLES VIRUS CONSENSUS HEMAGGLUTININ AND FUSION POLYPEPTIDES AND METHODS OF DETECTION

[75] Inventors: Jennifer S. Rota, Decatur; William J. Bellini, Lilburn, both of Ga.

[73] Assignee: The United States of America as represented by the Department of Health and Human Services, Washington, D.C.

[21] Appl. No.: 279,700

[22] Filed: Jul. 25, 1994

Related U.S. Application Data

[63] Continuation of Ser. No. 866,033, Apr. 8, 1992, abandoned.

[51] Int. Cl.⁶ .......................... C07H 21/04; C12P 19/34; C12Q 1/68; C12Q 1/70

[52] U.S. Cl. .................. 435/5; 435/6; 435/91.1; 435/91.2; 435/91.53; 435/172.3; 435/320.1; 536/23.7; 536/23.72; 536/24.32; 536/24.33

[58] Field of Search .......................... 435/6, 91.1, 91.2, 435/5, 380.1, 91.53, 172.1; 536/23.7, 23.72, 24.32, 24.33

[56] References Cited

PUBLICATIONS

Cattaneo et al. Cell 55:255–256, 1988.
Gerald et al. J. Gen. Virol. 67:2695–2703, 1986.
Rota et al. Virology 188:135–142, 1992.
Buckland et al. J. Gen. Virology 68:1695–1703, 1987.
Chehab et al. Nature 329:293–294, 1987.
Alkhatlb et al., "The Predicted Primary Structure of the Measles Virus Hemagglutinin," Virology 150: 479–490 (1986) Spec. p. 12. lines 14–18.

Drillien et al., "Protection of mice from fatal measles encephalitis by vaccination with vaccinia virus recombinants encoding either the hemagglutinin or the fusion protein," Proc. Nat'l. Acad. Sci. USA 86: 1252–56 (1988).
Hilleman et al., "Development and Evaluation of the Moraten Measles Virus Vaccine," JAMA 206: 587–90 (1968) Spec. p. 1, lines 14–18.
Richardson et al., "The Nucleotide Sequence of the mRNA Encoding the Fusion Protein of Measles Virus (Edmonston Strain): A comparison of Fusion Proteins from Several Different Paramyxoviruses," Virology 155: 508–523 (1986) Spec. p. 12, lines 15–19.
K. Baczko et al., "Nucleotide sequence of the genes encoding the matrix protein of two wild–type virus strains", J. Gen. Virology, vol. 72, No. 9, Sep. 1991, Soc. Gen. Microbiol., Reading, UK; pp. 2279–2282.
M. J. Taylor et al. "Identification of several different lineages of measles virus", J. Gen. Virology, vol. 72, No. 1, Jan. 1991, Soc. Gen. Microbiol., Reading, UK; pp. 83–88.
R. Cattaneo et al., "Mutated and hypermutated genes of persistent measles viruses which caused lethal human brain diseases", Virology, vol. 173, No. 2, Dec. 1989, Academic Press Ince., NY, U.S; pp. 415–425.

Primary Examiner—Stephanie W. Zitomer
Assistant Examiner—Paul B. Tran
Attorney, Agent, or Firm—Needle & Rosenberg, PC

[57] ABSTRACT

The present invention provides nucleic acids encoding consensus hemagglutinin and consensus fusion polypeptides which contain at least one amino acid substitution relative to the Moraten vaccine strain that is found in at least one strain of wild-type measles virus. Nucleic acid reagents useful for detecting and differentiating wild-type measles strains by polymerase chain reaction and a method utilizing the same are provided. Recombinant vectors comprising nucleic acids encoding the consensus hemagglutinin and/or the consensus fusion polypeptides are also provided.

12 Claims, 34 Drawing Sheets

| | AMINO ACID # | Mor | JM | Mel | Chi-1 | SD | Chi-2 |
|---|---|---|---|---|---|---|---|
| | 4 | Q | . | . | H | H | . |
| | 19 | K | . | R | . | . | . |
| 1 | 174 | T | . | A | A | A | A |
| | 176 | T | . | V | A | A | . |
| 2 | 211 | G | S | N | S | S | S |
| | 235 | E | . | . | G | G | . |
| | 243 | R | G | G | G | G | G |
| | 252 | Y | . | H | H | H | H |
| 3–6 | 276 | L | F | F | F | F | F |
| | 284 | L | . | F | F | F | F |
| | 295 | K | . | . | R | R | . |
| 7 | 296 | L | . | F | F | F | F |
| 8 | 302 | G | . | R | R | R | R |
| | 303 | E | G | . | . | . | . |
| | 305 | S | . | . | . | . | F |
| | 306 | I | . | . | V | V | . |
| | 308 | I | . | . | V | V | . |
| | 320 | Q | . | . | . | . | R |
| | 339 | L | F | . | . | . | . |
| | 348 | R | . | . | . | . | K |
| | 367 | V | I | . | . | . | . |
| | 389 | K | . | . | . | . | R |
| | 390 | I | . | . | N | N | . |
| 9 | 416 | D | . | N | N | N | N |
| | 446 | S | . | . | T | T | . |
| | 451 | V | E | . | . | . | . |
| 10 | 481 | Y | N | N | N | N | N |
| | 485 | V | . | . | . | . | I |
| | 501 | P | . | . | . | . | S |
| | 544 | S | . | . | . | . | N |
| | 546 | S | . | . | G | . | . |
| | 559 | I | . | . | . | . | V |
| | 560 | K | . | R | . | . | . |
| | 562 | V | I | . | . | . | F |
| | 593 | H | . | Y | . | . | . |
| | 616 | R | S | . | . | . | . |

|  | AMINO ACID # | Mor | JM | McI | Chi-1 | SD | Chi-2 |
|---|---|---|---|---|---|---|---|
|  | 4 | Q | · | · | H | H | · |
|  | 19 | K | · | R | · | · | · |
| 1 | 174 | T | · | A | A | A | A |
|  | 176 | T | · | V | A | A | · |
| 2 | 211 | G | S | N | S | S | S |
|  | 235 | E | · | · | G | G | · |
| 3-6 | 243 | R | G | G | G | G | G |
|  | 252 | Y | · | H | H | H | H |
|  | 276 | L | F | F | F | F | F |
|  | 284 | L | · | F | F | F | F |
|  | 295 | K | · | · | R | R | · |
| 7 | 296 | L | · | F | F | F | F |
| 8 | 302 | G | · | R | R | R | R |
|  | 303 | E | G | · | · | · | · |
|  | 305 | S | · | · | · | · | F |
|  | 306 | I | · | · | V | V | · |
|  | 308 | I | · | · | V | V | · |
|  | 320 | Q | · | · | · | · | R |
|  | 339 | L | F | · | · | · | · |
|  | 348 | R | · | · | · | · | K |
|  | 367 | V | I | · | · | · | · |
|  | 389 | K | · | · | · | · | R |
|  | 390 | I | · | · | N | N | · |
| 9 | 416 | D | · | N | N | N | N |
|  | 446 | S | · | · | T | T | · |
|  | 451 | V | E | · | · | · | · |
| 10 | 481 | Y | N | N | N | N | N |
|  | 485 | V | · | · | · | · | I |
|  | 501 | P | · | · | · | · | S |
|  | 544 | S | · | · | · | · | N |
|  | 546 | S | · | · | G | · | · |
|  | 559 | I | · | · | · | · | V |
|  | 560 | K | · | R | · | · | · |
|  | 562 | V | I | · | · | · | F |
|  | 593 | H | · | Y | · | · | · |
|  | 616 | R | S | · | · | · | · |

FIG.1A

TOTAL NUCLEOTIDE DIFFERENCES

| | Mor | JM | McI | Ch2 | SD | Ch1 |
|---|---|---|---|---|---|---|
| Mor | 0 | 27 | 41 | 54 | 55 | 56 |
| JM | 10 | 0 | 50 | 62 | 64 | 65 |
| McI | 14 | 17 | 0 | 39 | 38 | 39 |
| Ch2 | 19 | 20 | 14 | 0 | 37 | 38 |
| SD | 18 | 20 | 12 | 17 | 0 | 3 |
| Ch1 | 19 | 21 | 13 | 18 | 1 | 0 |

TOTAL PREDICTED AMINO ACID DIFFERENCES

Moraten HA Nucleotide and Amino Acid Sequence

```
AGGGTGCAAG ATCATCCACA ATG TCA CCA CAA CGA GAC CGG ATA AAT GCC          50
                     Met Ser Pro Gln Arg Asp Arg Ile Asn Ala
                      1               5                   10

TTC TAC AAA GAT AAC CCC CAT CCC AAG GGA AGT AGG ATA GTC ATT AAC        98
Phe Tyr Lys Asp Asn Pro His Pro Lys Gly Ser Arg Ile Val Ile Asn
                15              20                  25

AGA GAA CAT CTT ATG ATT GAT AGA CCT TAT GTT TTG CTG GCT GTT CTG       146
Arg Glu His Leu Met Ile Asp Arg Pro Tyr Val Leu Leu Ala Val Leu
            30              35                  40

TTT GTC ATG TTT CTG AGC TTG ATC GGG TTG CTA GCC ATT GCA GGC ATT       194
Phe Val Met Phe Leu Ser Leu Ile Gly Leu Leu Ala Ile Ala Gly Ile
        45                  50                  55

AGA CTT CAT CGG GCA GCC ATC TAC ACC GCA GAG ATC CAT AAA AGC CTC       242
Arg Leu His Arg Ala Ala Ile Tyr Thr Ala Glu Ile His Lys Ser Leu
    60                  65                  70

AGC ACC AAT CTA GAT GTA ACT AAC TCA ATC GAG CAT CAG GTC AAG GAC       290
Ser Thr Asn Leu Asp Val Thr Asn Ser Ile Glu His Gln Val Lys Asp
75                  80                  85                  90

GTG CTG ACA CCA CTC TTC AAA ATC ATC GGT GAT GAA GTG GGC CTG AGG       338
Val Leu Thr Pro Leu Phe Lys Ile Ile Gly Asp Glu Val Gly Leu Arg
                95                  100                 105

ACA CCT CAG AGA TTC ACT GAC CTA GTG AAA TTC ATC TCT GAC AAG ATT       386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAT CTC ACT TGG       434
Lys Phe Leu Asn Pro Asp Arg Glu Tyr Asp Phe Arg Asp Leu Thr Trp
        125                 130                 135

TGT ATC AAC CCG CCA GAG AGA ATC AAA TTG GAT TAT GAT CAA TAC TGT       482
Cys Ile Asn Pro Pro Glu Arg Ile Lys Leu Asp Tyr Asp Gln Tyr Cys
    140                 145                 150

GCA GAT GTG GCT GCT GAA GAG CTC ATG AAT GCA TTG GTG AAC TCA ACT       530
Ala Asp Val Ala Ala Glu Glu Leu Met Asn Ala Leu Val Asn Ser Thr
155                 160                 165                 170

CTA CTG GAG ACC AGA ACA ACC AAT CAG TTC CTA GCT GTC TCA AAG GGA       578
Leu Leu Glu Thr Arg Thr Thr Asn Gln Phe Leu Ala Val Ser Lys Gly
                175                 180                 185

AAC TGC TCA GGG CCC ACT ACA ATC AGA GGT CAA TTC TCA AAC ATG TCG       626
Asn Cys Ser Gly Pro Thr Thr Ile Arg Gly Gln Phe Ser Asn Met Ser
            190                 195                 200

CTG TCC CTG TTA GAC TTG TAT TTA GGT CGA GGT TAC AAT GTG TCA TCT       674
Leu Ser Leu Leu Asp Leu Tyr Leu Gly Arg Gly Tyr Asn Val Ser Ser
        205                 210                 215

ATA GTC ACT ATG ACA TCC CAG GGA ATG TAT GGG GGA ACT TAC CTA GTG       722
Ile Val Thr Met Thr Ser Gln Gly Met Tyr Gly Gly Thr Tyr Leu Val
    220                 225                 230

GAA AAG CCT AAT CTG AGC AGC AAA AGG TCA GAG TTG TCA CAA CTG AGC       770
Glu Lys Pro Asn Leu Ser Ser Lys Arg Ser Glu Leu Ser Gln Leu Ser
235                 240                 245                 250
```

FIGURE 3

```
ATG TAC CGA GTG TTT GAA GTA GGT GTT ATC AGA AAT CCG GGT TTG GGG           818
Met Tyr Arg Val Phe Glu Val Gly Val Ile Arg Asn Pro Gly Leu Gly
            255                 260                 265

GCT CCG GTG TTC CAT ATG ACA AAC TAT CTT GAG CAA CCA GTC AGT AAT           866
Ala Pro Val Phe His Met Thr Asn Tyr Leu Glu Gln Pro Val Ser Asn
            270                 275                 280

GAT CTC AGC AAC TGT ATG GTG GCT TTG GGG GAG CTC AAA CTC GCA GCC           914
Asp Leu Ser Asn Cys Met Val Ala Leu Gly Glu Leu Lys Leu Ala Ala
            285                 290                 295

CTT TGT CAC GGG GAA GAT TCT ATC ACA ATT CCC TAT CAG GGA TCA GGG           962
Leu Cys His Gly Glu Asp Ser Ile Thr Ile Pro Tyr Gln Gly Ser Gly
300                 305                 310

AAA GGT GTC AGC TTC CAG CTC GTC AAG CTA GGT GTC TGG AAA TCC CCA          1010
Lys Gly Val Ser Phe Gln Leu Val Lys Leu Gly Val Trp Lys Ser Pro
315                 320                 325                 330

ACC GAC ATG CAA TCC TGG GTC CCC TTA TCA ACG GAT GAT CCA GTG ATA          1058
Thr Asp Met Gln Ser Trp Val Pro Leu Ser Thr Asp Asp Pro Val Ile
                335                 340                 345

GAC AGG CTT TAC CTC TCA TCT CAC AGA GGT GTT ATC GCT GAC AAT CAA          1106
Asp Arg Leu Tyr Leu Ser Ser His Arg Gly Val Ile Ala Asp Asn Gln
            350                 355                 360

GCA AAA TGG GCT GTC CCG ACA ACA CGA ACA GAT GAC AAG TTG CGA ATG          1154
Ala Lys Trp Ala Val Pro Thr Thr Arg Thr Asp Asp Lys Leu Arg Met
            365                 370                 375

GAG ACA TGC TTC CAA CAG GCG TGT AAG GGT AAA ATC CAA GCA CTC TGC          1202
Glu Thr Cys Phe Gln Gln Ala Cys Lys Gly Lys Ile Gln Ala Leu Cys
380                 385                 390

GAG AAT CCC GAG TGG GCA CCA TTG AAG GAT AAC AGG ATT CCT TCA TAC          1250
Glu Asn Pro Glu Trp Ala Pro Leu Lys Asp Asn Arg Ile Pro Ser Tyr
395                 400                 405                 410

GGG GTC TTG TCT GTT GAT CTG AGT CTG ACA GTT GAG CTT AAA ATC AAA          1298
Gly Val Leu Ser Val Asp Leu Ser Leu Thr Val Glu Leu Lys Ile Lys
                415                 420                 425

ATT GCT TCG GGA TTC GGG CCA TTG ATC ACA CAC GGT TCA GGG ATG GAC          1346
Ile Ala Ser Gly Phe Gly Pro Leu Ile Thr His Gly Ser Gly Met Asp
            430                 435                 440

CTA TAC AAA TCC AAC CAC AAC AAT GTG TAT TGG CTG ACT ATC CCG CCA          1394
Leu Tyr Lys Ser Asn His Asn Asn Val Tyr Trp Leu Thr Ile Pro Pro
            445                 450                 455

ATG AAG AAC CTA GCC TTA GGT GTA ATC AAC ACA TTG GAG TGG ATA CCG          1442
Met Lys Asn Leu Ala Leu Gly Val Ile Asn Thr Leu Glu Trp Ile Pro
460                 465                 470

AGA TTC AAG GTT AGT CCC TAC CTC TTC ACT GTC CCA ATT AAG GAA GCA          1490
Arg Phe Lys Val Ser Pro Tyr Leu Phe Thr Val Pro Ile Lys Glu Ala
475                 480                 485                 490

GGC GAA GAC TGC CAT GCC CCA ACA TAC CTA CCT GCG GAG GTG GAT GGT          1538
Gly Glu Asp Cys His Ala Pro Thr Tyr Leu Pro Ala Glu Val Asp Gly
                495                 500                 505

GAT GTC AAA CTC AGT TCC AAT CTG GTG ATT CTA CCT GGT CAA GAT CTC          1586
Asp Val Lys Leu Ser Ser Asn Leu Val Ile Leu Pro Gly Gln Asp Leu
            510                 515                 520
```

FIGURE 3

```
CAA TAT GTT TTG GCA ACC TAC GAT ACT TCC AGG GTT GAA CAT GCT GTG        1634
Gln Tyr Val Leu Ala Thr Tyr Asp Thr Ser Arg Val Glu His Ala Val
        525                 530                 535

GTT TAT TAC GTT TAC AGC CCA AGC CGC TCA TTT TCT TAC TTT TAT CCT        1682
Val Tyr Tyr Val Tyr Ser Pro Ser Arg Ser Phe Ser Tyr Phe Tyr Pro
        540                 545                 550

TTT AGG TTG CCT ATA AAG GGG GTC CCC ATC GAA TTA CAA GTG GAA TGC        1730
Phe Arg Leu Pro Ile Lys Gly Val Pro Ile Glu Leu Gln Val Glu Cys
555                 560                 565                 570

TTC ACA TGG GAC CAA AAA CTC TGG TGC CGT CAC TTC TGT GTG CTT GCG        1778
Phe Thr Trp Asp Gln Lys Leu Trp Cys Arg His Phe Cys Val Leu Ala
                575                 580                 585

GAC TCA GAA TCT GGT GGA CAT ATC ACT CAC TCT GGG ATG GTG GGC ATG        1826
Asp Ser Glu Ser Gly Gly His Ile Thr His Ser Gly Met Val Gly Met
                590                 595                 600

GGA GTC AGC TGC ACA GTC ACC CGG GAA GAT GGA ACC AAT CGC AGA TAGGGCTGCT
1881
Gly Val Ser Cys Thr Val Thr Arg Glu Asp Gly Thr Asn Arg Arg
        605                 610                 615

AGTGAACCAA TCTCATGATG TCACCCAGAC ATCAGGCA                              1919
```

FIGURE 4

Consensus Nucleotide and Amino Acid Sequence

| | | |
|---|---|---|
| AGGGTGCAAG ATCATCCACA ATG TCA CCA CAC CGA GAC CGA ATA AAT GCC<br>                                             Met Ser Pro His Arg Asp Arg Ile Asn Ala<br>                                              1           5                        10 | 50 |
| TTC TAC AAA GAC AAC CCC CAT CCT AAG GGA AGT AGG ATA GTT ATT AAC<br>Phe Tyr Lys Asp Asn Pro His Pro Lys Gly Ser Arg Ile Val Ile Asn<br>               15                    20                   25 | 98 |
| AGA GAA CAT CTT ATG ATT GAT AGA CCT TAT GTT TTG CTG GCT GTT CTA<br>Arg Glu His Leu Met Ile Asp Arg Pro Tyr Val Leu Leu Ala Val Leu<br>            30                       35                 40 | 146 |
| TTC GTC ATG TTT CTG AGC TTG ATC GGG TTG CTA GCC ATT GCA GGC ATT<br>Phe Val Met Phe Leu Ser Leu Ile Gly Leu Leu Ala Ile Ala Gly Ile<br>         45                   50                55 | 194 |
| AGA CTC CAT CGG GCA GCC ATC TAC ACC GCA GAG ATC CAT AAG AGC CTC<br>Arg Leu His Arg Ala Ala Ile Tyr Thr Ala Glu Ile His Lys Ser Leu<br>    60                   65                 70 | 242 |
| AGC ACC AAT CTA GAT GTA ACT AAC TCA ATC GAG CAT CAG GTC AAG GAC<br>Ser Thr Asn Leu Asp Val Thr Asn Ser Ile Glu His Gln Val Lys Asp<br>75                 80                 85                 90 | 290 |
| GTG CTG ACA CCA CTC TTC AAG ATC ATC GGT GAT GAA GTG GGC CTG AGG<br>Val Leu Thr Pro Leu Phe Lys Ile Ile Gly Asp Glu Val Gly Leu Arg<br>                   95                 100              105 | 338 |
| ACA CCT CAG AGA TTC ACT GAC CTA GTG AAA TTC ATC TCT GAC AAA ATT<br>Thr Pro Gln Arg Phe Thr Asp Leu Val Lys Phe Ile Ser Asp Lys Ile<br>           110                   115                120 | 386 |
| AAA TTC CTT AAT CCG GAT AGG GAG TAC GAC TTC AGA GAT CTC ACT TGG<br>Lys Phe Leu Asn Pro Asp Arg Glu Tyr Asp Phe Arg Asp Leu Thr Trp<br>        125                   130                135 | 434 |
| TGT ATC AAC CCG CCA GAG AGA ATC AAA TTG GAT TAT GAT CAA TAC TGT<br>Cys Ile Asn Pro Pro Glu Arg Ile Lys Leu Asp Tyr Asp Gln Tyr Cys<br>    140                   145                 150 | 482 |
| GCA GAT GTG GCT GCT GAA GAA CTC ATG AAT GCA TTG GTG AAC TCA ACT<br>Ala Asp Val Ala Ala Glu Glu Leu Met Asn Ala Leu Val Asn Ser Thr<br>155                 160                 165                170 | 530 |
| CTA CTG GAG GCC AGG GCA ACC AAT CAG TTC CTA GCT GTC TCA AAG GGA<br>Leu Leu Glu Ala Arg Ala Thr Asn Gln Phe Leu Ala Val Ser Lys Gly<br>                175                 180               185 | 578 |
| AAC TGC TCA GGG CCC ACT ACA ATC AGA GGT CAA TTC TCA AAC ATG TCG<br>Asn Cys Ser Gly Pro Thr Thr Ile Arg Gly Gln Phe Ser Asn Met Ser<br>          190                   195                200 | 626 |
| CTG TCC CTG TTG GAC TTG TAT TTA AGT CGA GGT TAC AAT GTG TCA TCT<br>Leu Ser Leu Leu Asp Leu Tyr Leu Ser Arg Gly Tyr Asn Val Ser Ser<br>        205                   210                215 | 674 |
| ATA GTC ACC ATG ACA TCC CAG GGA ATG TAC GGG GGA ACT TAC CTA GTG<br>Ile Val Thr Met Thr Ser Gln Gly Met Tyr Gly Gly Thr Tyr Leu Val<br>          220                   225                230 | 722 |
| GGA AAG CCT AAT CTG AGC AGT AAA GGG TCA GAG TTG TCA CAA CTG AGC<br>Gly Lys Pro Asn Leu Ser Ser Lys Gly Ser Glu Leu Ser Gln Leu Ser<br>235                 240                 245                250 | 770 |

FIGURE 4

```
ATG CAC CGA GTG TTT GAA GTA GGG GTT ATC AGA AAT CCG GGT TTG GGG        818
Met His Arg Val Phe Glu Val Gly Val Ile Arg Asn Pro Gly Leu Gly
            255                 260                 265

GCT CCG GTG TTC CAT ATG ACA AAC TAT TTT GAG CAA CCA GTC AGT AAT        866
Ala Pro Val Phe His Met Thr Asn Tyr Phe Glu Gln Pro Val Ser Asn
            270                 275                 280

GAT TTC AGC AAC TGC ATG GTG GCT TTG GGG GAG CTC AGG TTC GCA GCC        914
Asp Phe Ser Asn Cys Met Val Ala Leu Gly Glu Leu Arg Phe Ala Ala
            285                 290                 295

CTC TGT CAC AGG GAA GAT TCT GTC ACG GTT CCC TAT CAG GGG TCA GGG        962
Leu Cys His Arg Glu Asp Ser Val Thr Val Pro Tyr Gln Gly Ser Gly
300             305                 310

AAA GGT GTC AGC TTC CAG CTC GTC AAG CTA GGT GTC TGG AAA TCC CCA       1010
Lys Gly Val Ser Phe Gln Leu Val Lys Leu Gly Val Trp Lys Ser Pro
315             320                 325                 330

ACC GAC ATG CAA TCC TGG GTC CCC CTA TCA ACG GAT GAT CCA GTG ATA       1058
Thr Asp Met Gln Ser Trp Val Pro Leu Ser Thr Asp Asp Pro Val Ile
                335                 340                 345

GAT AGG CTT TAC CTC TCA TCT CAC AGA GGT GTT ATC GCT GAC AAT CAA       1106
Asp Arg Leu Tyr Leu Ser Ser His Arg Gly Val Ile Ala Asp Asn Gln
            350                 355                 360

GCA AAA TGG GCT GTC CCG ACA ACA CGG ACA GAT GAC AAG TTG CGA ATG       1154
Ala Lys Trp Ala Val Pro Thr Thr Arg Thr Asp Asp Lys Leu Arg Met
        365                 370                 375

GAG ACA TGC TTC CAG CAG GCG TGT AAG GGT AAA AAC CAA GCA CTC TGC       1202
Glu Thr Cys Phe Gln Gln Ala Cys Lys Gly Lys Asn Gln Ala Leu Cys
        380                 385                 390

GAG AAT CCC GAG TGG GCA CCA TTG AAG GAT AAC AGG ATT CCT TCA TAC       1250
Glu Asn Pro Glu Trp Ala Pro Leu Lys Asp Asn Arg Ile Pro Ser Tyr
395                 400                 405                 410

GGG GTC TTG TCT GTT AAT CTG AGT CTG ACA GTT GAG CTT AAA ATC AAA       1298
Gly Val Leu Ser Val Asn Leu Ser Leu Thr Val Glu Leu Lys Ile Lys
                415                 420                 425

ATT GCT TCA GGA TTC GGG CCA TTG ATC ACA CAC GGT TCA GGG ATG GAC       1346
Ile Ala Ser Gly Phe Gly Pro Leu Ile Thr His Gly Ser Gly Met Asp
            430                 435                 440

CTA TAC AAA ACC AAC CAC AAC AAT GTG TAT TGG CTG ACT ATC CCG CCA       1394
Leu Tyr Lys Thr Asn His Asn Asn Val Tyr Trp Leu Thr Ile Pro Pro
            445                 450                 455

ATG AAG AAC CTA GCC TTA GGT GTA ATC AAC ACA TTG GAG TGG ATA CCG       1442
Met Lys Asn Leu Ala Leu Gly Val Ile Asn Thr Leu Glu Trp Ile Pro
460                 465                 470

AGA TTC AAG GTT AGT CCC AAC CTC TTC ACT GTT CCA ATC AAG GAA GCA       1490
Arg Phe Lys Val Ser Pro Asn Leu Phe Thr Val Pro Ile Lys Glu Ala
475                 480                 485                 490

GGC GAG GAC TGC CAT GCC CCA ACA TAC CTA CCT GCG GAG GTG GAT GGT       1538
Gly Glu Asp Cys His Ala Pro Thr Tyr Leu Pro Ala Glu Val Asp Gly
                495                 500                 505

GAT GTC AAA CTC AGT TCC AAT CTG GTA ATT CTA CCT GGT CAG GAT CTC       1586
Asp Val Lys Leu Ser Ser Asn Leu Val Ile Leu Pro Gly Gln Asp Leu
            510                 515                 520
```

FIGURE 4

```
CAA TAT GTT TTG GCA ACC TAC GAT ACT TCC AGG GTT GAA CAT GCT GTG         1634
Gln Tyr Val Leu Ala Thr Tyr Asp Thr Ser Arg Val Glu His Ala Val
        525                 530                 535

GTT TAT TAT GTT TAC AGC CCA AGC CGC TCA TTT TCT TAC TTT TAT CCT         1682
Val Tyr Tyr Val Tyr Ser Pro Ser Arg Ser Phe Ser Tyr Phe Tyr Pro
    540                 545                 550

TTT AGG TTG CCT ATA AAG GGG GTC CCA ATC GAA TTA CAA GTG GAA TGC         1730
Phe Arg Leu Pro Ile Lys Gly Val Pro Ile Glu Leu Gln Val Glu Cys
555                 560                 565                 570

TTC ACA TGG GAC CAA AAA CTC TGG TGC CGT CAC TTC TGT GTG CTT GCG         1778
Phe Thr Trp Asp Gln Lys Leu Trp Cys Arg His Phe Cys Val Leu Ala
                575                 580                 585

GAT TCA GAA TCT GGT GGA CAT ATC ACT CAC TCT GGG ATG GTG GGC ATG         1826
Asp Ser Glu Ser Gly Gly His Ile Thr His Ser Gly Met Val Gly Met
            590                 595                 600

GGA GTC AGC TGC ACA GTC ACT CGG GAA GAT GGA ACC AAT CGC AGA TA          1874
Gly Val Ser Cys Thr Val Thr Arg Glu Asp Gly Thr Asn Arg Arg
        605                 610                 615
```

FIGURE 5

Wild-Type Isolate San Diego HA Nucleotide and Amino Acid Sequence

```
AGGGTGCAAG ATCATCCACA ATG TCA CCA CAC CGA GAC CGA ATA AAT GCC       50
                      Met Ser Pro His Arg Asp Arg Ile Asn Ala
                       1           5                       10

TTC TAC AAA GAC AAC CCC CAT CCT AAG GGA AGT AGG ATA GTT ATT AAC      98
Phe Tyr Lys Asp Asn Pro His Pro Lys Gly Ser Arg Ile Val Ile Asn
                15                  20                  25

AGA GAA CAT CTT ATG ATT GAT CGA CCT TAT GTT TTG CTG GCT GTT CTA     146
Arg Glu His Leu Met Ile Asp Arg Pro Tyr Val Leu Leu Ala Val Leu
            30                  35                  40

TTC GTC ATG TTT CTG AGC TTG ATC GGG TTG CTA GCC ATT GCA GGC ATT     194
Phe Val Met Phe Leu Ser Leu Ile Gly Leu Leu Ala Ile Ala Gly Ile
        45                  50                  55

AGA CTC CAT CGG GCA GCC ATC TAC ACC GCA GAG ATC CAT AAG AGC CTC     242
Arg Leu His Arg Ala Ala Ile Tyr Thr Ala Glu Ile His Lys Ser Leu
    60                  65                  70

AGC ACC AAT CTA GAT GTA ACT AAC TCA ATC GAG CAT CAG GTC AAG GAC     290
Ser Thr Asn Leu Asp Val Thr Asn Ser Ile Glu His Gln Val Lys Asp
75                  80                  85                  90

GTG CTG ACA CCA CTC TTC AAG ATC ATC GGT GAT GAA GTG GGC CTG AGG     338
Val Leu Thr Pro Leu Phe Lys Ile Ile Gly Asp Glu Val Gly Leu Arg
                95                  100                 105

ACA CCT CAG AGA TTC ACT GAC CTA GTG AAA TTC ATC TCT GAC AAA ATT     386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAT CTC ACT TGG     434
Lys Phe Leu Asn Pro Asp Arg Glu Tyr Asp Phe Arg Asp Leu Thr Trp
        125                 130                 135

TGT ATC AAC CCG CCA GAG AGA ATC AAA TTG GAT TAT GAT CAA TAC TGT     482
Cys Ile Asn Pro Pro Glu Arg Ile Lys Leu Asp Tyr Asp Gln Tyr Cys
    140                 145                 150

GCA GAT GTG GCT GCT GAA GAA CTC ATG AAT GCA TTG GTG AAC TCA ACT     530
Ala Asp Val Ala Ala Glu Glu Leu Met Asn Ala Leu Val Asn Ser Thr
155                 160                 165                 170

CTA CTG GAG GCC AGG GCA ACC AAT CAG TTC CTA GCT GTC TCA AAG GGA     578
Leu Leu Glu Ala Arg Ala Thr Asn Gln Phe Leu Ala Val Ser Lys Gly
                175                 180                 185

AAC TGC TCA GGG CCC ACT ACA ATC AGA GGT CAA TTC TCA AAC ATG TCG     626
Asn Cys Ser Gly Pro Thr Thr Ile Arg Gly Gln Phe Ser Asn Met Ser
            190                 195                 200

CTG TCC CTG TTG GAC TTG TAT TTA AGT CGA GGT TAC AAT GTG TCA TCT     674
Leu Ser Leu Leu Asp Leu Tyr Leu Ser Arg Gly Tyr Asn Val Ser Ser
        205                 210                 215

ATA GTC ACC ATG ACA TCC CAG GGA ATG TAC GGG GGA ACT TAC CTA GTG     722
Ile Val Thr Met Thr Ser Gln Gly Met Tyr Gly Gly Thr Tyr Leu Val
    220                 225                 230

GGA AAG CCT AAT CTG AGC AGT AAA GGG TCA GAG TTG TCA CAA CTG AGC     770
Gly Lys Pro Asn Leu Ser Ser Lys Gly Ser Glu Leu Ser Gln Leu Ser
235                 240                 245                 250
```

FIGURE 5

```
ATG CAC CGA GTG TTT GAA GTA GGG GTT ATC AGA AAT CCG GGT TTG GGG      818
Met His Arg Val Phe Glu Val Gly Val Ile Arg Asn Pro Gly Leu Gly
        255                 260                 265

GCT CCG GTG TTC CAT ATG ACA AAC TAT TTT GAG CAA CCA GTC AGT AAT      866
Ala Pro Val Phe His Met Thr Asn Tyr Phe Glu Gln Pro Val Ser Asn
        270                 275                 280

GAT TTC AGC AAC TGC ATG GTG GCT TTG GGG GAG CTC AGG TTC GCA GCC      914
Asp Phe Ser Asn Cys Met Val Ala Leu Gly Glu Leu Arg Phe Ala Ala
        285                 290                 295

CTC TGT CAC AGG GAA GAT TCT GTC ACG GTT CCC TAT CAG GGG TCA GGG      962
Leu Cys His Arg Glu Asp Ser Val Thr Val Pro Tyr Gln Gly Ser Gly
300                 305                 310

AAA GGT GTC AGC TTC CAG CTC GTC AAG CTA GGT GTC TGG AAA TCC CCA     1010
Lys Gly Val Ser Phe Gln Leu Val Lys Leu Gly Val Trp Lys Ser Pro
315                 320                 325                 330

ACC GAC ATG CAA TCC TGG GTC CCC CTA TCA ACG GAT GAT CCA GTG ATA     1058
Thr Asp Met Gln Ser Trp Val Pro Leu Ser Thr Asp Asp Pro Val Ile
            335                 340                 345

GAT AGG CTT TAC CTC TCA TCT CAC AGA GGT GTT ATC GCT GAC AAT CAA     1106
Asp Arg Leu Tyr Leu Ser Ser His Arg Gly Val Ile Ala Asp Asn Gln
        350                 355                 360

GCA AAA TGG GCT GTC CCG ACA ACA CGG ACA GAT GAC AAG TTG CGA ATG     1154
Ala Lys Trp Ala Val Pro Thr Thr Arg Thr Asp Asp Lys Leu Arg Met
        365                 370                 375

GAG ACA TGC TTC CAG CAG GCG TGT AAG GGT AAA AAC CAA GCA CTC TGC     1202
Glu Thr Cys Phe Gln Gln Ala Cys Lys Gly Lys Asn Gln Ala Leu Cys
        380                 385                 390

GAG AAT CCC GAG TGG GCA CCA TTG AAG GAT AAC AGG ATT CCT TCA TAC     1250
Glu Asn Pro Glu Trp Ala Pro Leu Lys Asp Asn Arg Ile Pro Ser Tyr
395                 400                 405                 410

GGG GTC TTG TCT GTT AAT CTG AGT CTG ACA GTT GAG CTT AAA ATC AAA     1298
Gly Val Leu Ser Val Asn Leu Ser Leu Thr Val Glu Leu Lys Ile Lys
            415                 420                 425

ATT GCT TCA GGA TTC GGG CCA TTG ATC ACA CAC GGT TCA GGG ATG GAC     1346
Ile Ala Ser Gly Phe Gly Pro Leu Ile Thr His Gly Ser Gly Met Asp
        430                 435                 440

CTA TAC AAA ACC AAC CAC AAC AAT GTG TAT TGG CTG ACT ATC CCG CCA     1394
Leu Tyr Lys Thr Asn His Asn Asn Val Tyr Trp Leu Thr Ile Pro Pro
        445                 450                 455

ATG AAG AAC CTA GCC TTA GGT GTA ATC AAC ACA TTG GAG TGG ATA CCG     1442
Met Lys Asn Leu Ala Leu Gly Val Ile Asn Thr Leu Glu Trp Ile Pro
        460                 465                 470

AGA TTC AAG GTT AGT CCC AAC CTC TTC ACT GTT CCA ATC AAG GAA GCA     1490
Arg Phe Lys Val Ser Pro Asn Leu Phe Thr Val Pro Ile Lys Glu Ala
475                 480                 485                 490

GGC GAG GAC TGC CAT GCC CCA ACA TAC CTA CCT GCG GAG GTG GAT GGT     1538
Gly Glu Asp Cys His Ala Pro Thr Tyr Leu Pro Ala Glu Val Asp Gly
            495                 500                 505

GAT GTC AAA CTC AGT TCC AAT CTG GTA ATT CTA CCT GGT CAG GAT CTC     1586
Asp Val Lys Leu Ser Ser Asn Leu Val Ile Leu Pro Gly Gln Asp Leu
        510                 515                 520
```

FIGURE 5

```
CAA TAT GTT TTG GCA ACC TAC GAT ACT TCC AGG GTT GAA CAT GCT GTG         1634
Gln Tyr Val Leu Ala Thr Tyr Asp Thr Ser Arg Val Glu His Ala Val
        525                     530                 535

GTT TAT TAT GTT TAC AGC CCA AGC CGC TCA TTT TCT TAC TTT TAT CCT         1682
Val Tyr Tyr Val Tyr Ser Pro Ser Arg Ser Phe Ser Tyr Phe Tyr Pro
        540                     545                 550

TTT AGG TTG CCT ATA AAG GGG GTC CCA ATC GAA TTA CAA GTG GAA TGC         1730
Phe Arg Leu Pro Ile Lys Gly Val Pro Ile Glu Leu Gln Val Glu Cys
555                 560                 565                 570

TTC ACA TGG GAC CAA AAA CTC TGG TGC CGT CAC TTC TGT GTG CTT GCG         1778
Phe Thr Trp Asp Gln Lys Leu Trp Cys Arg His Phe Cys Val Leu Ala
                575                 580                 585

GAT TCA GAA TCT GGT GGA CAT ATC ACT CAC TCT GGG ATG GTG GGC ATG         1826
Asp Ser Glu Ser Gly Gly His Ile Thr His Ser Gly Met Val Gly Met
                590                 595                 600

GGA GTC AGC TGC ACA GTC ACC CGG GAA GAT GGA ACC AAT CGC AGA TAGGGCTGCT
1881
Gly Val Ser Cys Thr Val Thr Arg Glu Asp Gly Thr Asn Arg Arg
                605                 610                 615

AGTGAACCAA TCTCATGATG TCACCCAGAC ATCAGGCA                                1919
```

FIGURE 6

Wild-Type Isolate Chicago-1 HA Nucleotide and Amino Acid Sequence

```
AGGGTGCAAG ATCATCCACA ATG TCA CCA CAC CGA GAC CGA ATA AAT GCC         50
                     Met Ser Pro His Arg Asp Arg Ile Asn Ala
                      1             5                    10

TTC TAC AAA GAC AAC CCC CAT CCT AAG GGA AGT AGG ATA GTT ATT AAC         98
Phe Tyr Lys Asp Asn Pro His Pro Lys Gly Ser Arg Ile Val Ile Asn
            15                  20                      25

AGA GAA CAT CTT ATG ATT GAT AGA CCT TAT GTT TTG CTG GCT GTT CTA        146
Arg Glu His Leu Met Ile Asp Arg Pro Tyr Val Leu Leu Ala Val Leu
            30                  35                  40

TTC GTC ATG TTT CTG AGC TTG ATC GGG TTG CTA GCC ATT GCA GGC ATT        194
Phe Val Met Phe Leu Ser Leu Ile Gly Leu Leu Ala Ile Ala Gly Ile
            45                  50                  55

AGA CTC CAT CGG GCA GCC ATC TAC ACC GCA GAG ATC CAT AAG AGC CTC        242
Arg Leu His Arg Ala Ala Ile Tyr Thr Ala Glu Ile His Lys Ser Leu
        60                  65                  70

AGC ACC AAT CTA GAT GTA ACT AAC TCA ATC GAG CAT CAG GTC AAG GAC        290
Ser Thr Asn Leu Asp Val Thr Asn Ser Ile Glu His Gln Val Lys Asp
75              80                  85                      90

GTG CTG ACA CCA CTC TTC AAG ATC ATC GGT GAT GAA GTG GGC CTG AGG        338
Val Leu Thr Pro Leu Phe Lys Ile Ile Gly Asp Glu Val Gly Leu Arg
                95                  100                 105

ACA CCT CAG AGA TTC ACT GAC CTA GTG AAA TTC ATC TCT GAC AAA ATT        386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAT CTC ACT TGG        434
Lys Phe Leu Asn Pro Asp Arg Glu Tyr Asp Phe Arg Asp Leu Thr Trp
            125                 130                 135

TGT ATC AAC CCG CCA GAG AGA ATC AAA TTG GAT TAT GAT CAA TAC TGT        482
Cys Ile Asn Pro Pro Glu Arg Ile Lys Leu Asp Tyr Asp Gln Tyr Cys
    140                 145                 150

GCA GAT GTG GCT GCT GAA GAA CTC ATG AAT GCA TTG GTG AAC TCA ACT        530
Ala Asp Val Ala Ala Glu Glu Leu Met Asn Ala Leu Val Asn Ser Thr
155             160                 165                     170

CTA CTG GAG GCC AGG GCA ACC AAT CAG TTC CTA GCT GTC TCA AAG GGA        578
Leu Leu Glu Ala Arg Ala Thr Asn Gln Phe Leu Ala Val Ser Lys Gly
                175                 180                 185

AAC TGC TCA GGG CCC ACT ACA ATC AGA GGT CAA TTC TCA AAC ATG TCG        626
Asn Cys Ser Gly Pro Thr Thr Ile Arg Gly Gln Phe Ser Asn Met Ser
                190             195                 200

CTG TCC CTG TTG GAC TTG TAT TTA AGT CGA GGT TAC AAT GTG TCA TCT        674
Leu Ser Leu Leu Asp Leu Tyr Leu Ser Arg Gly Tyr Asn Val Ser Ser
            205                 210                 215

ATA GTC ACC ATG ACA TCC CAG GGA ATG TAC GGG GGA ACT TAC CTA GTG        722
Ile Val Thr Met Thr Ser Gln Gly Met Tyr Gly Gly Thr Tyr Leu Val
            220                 225                 230

GGA AAG CCT AAT CTG AGC AGT AAA GGG TCA GAG TTG TCA CAA CTG AGC        770
Gly Lys Pro Asn Leu Ser Ser Lys Gly Ser Glu Leu Ser Gln Leu Ser
235                 240                 245                 250
```

FIGURE 6

```
ATG CAC CGA GTG TTT GAA GTA GGG GTT ATC AGA AAT CCG GGT TTG GGG           818
Met His Arg Val Phe Glu Val Gly Val Ile Arg Asn Pro Gly Leu Gly
        255                 260                 265

GCT CCG GTG TTC CAT ATG ACA AAC TAT TTT GAG CAA CCA GTC AGT AAT           866
Ala Pro Val Phe His Met Thr Asn Tyr Phe Glu Gln Pro Val Ser Asn
        270                 275                 280

GAT TTC AGC AAC TGC ATG GTG GCT TTG GGG GAG CTC AGG TTC GCA GCC           914
Asp Phe Ser Asn Cys Met Val Ala Leu Gly Glu Leu Arg Phe Ala Ala
        285                 290                 295

CTC TGT CAC AGA GAA GAT TCT GTC ACG GTT CCC TAT CAG GGG TCA GGG           962
Leu Cys His Arg Glu Asp Ser Val Thr Val Pro Tyr Gln Gly Ser Gly
300                 305                 310

AAA GGT GTC AGC TTC CAG CTC GTC AAG CTA GGT GTC TGG AAA TCC CCA          1010
Lys Gly Val Ser Phe Gln Leu Val Lys Leu Gly Val Trp Lys Ser Pro
315                 320                 325                 330

ACC GAC ATG CAA TCC TGG GTC CCC CTA TCA ACG GAT GAT CCA GTG ATA          1058
Thr Asp Met Gln Ser Trp Val Pro Leu Ser Thr Asp Asp Pro Val Ile
                335                 340                 345

GAT AGG CTT TAC CTC TCA TCT CAC AGA GGT GTT ATC GCT GAC AAT CAA          1106
Asp Arg Leu Tyr Leu Ser Ser His Arg Gly Val Ile Ala Asp Asn Gln
                350                 355                 360

GCA AAA TGG GCT GTC CCG ACA ACA CGG ACA GAT GAC AAG TTG CGA ATG          1154
Ala Lys Trp Ala Val Pro Thr Thr Arg Thr Asp Asp Lys Leu Arg Met
        365                 370                 375

GAG ACA TGC TTC CAG CAG GCG TGT AAG GGT AAA AAC CAA GCA CTC TGC          1202
Glu Thr Cys Phe Gln Gln Ala Cys Lys Gly Lys Asn Gln Ala Leu Cys
380                 385                 390

GAG AAT CCC GAG TGG GCA CCA TTG AAG GAT AAC AGG ATT CCT TCA TAC          1250
Glu Asn Pro Glu Trp Ala Pro Leu Lys Asp Asn Arg Ile Pro Ser Tyr
395                 400                 405                 410

GGG GTC TTG TCT GTT AAT CTG AGT CTG ACA GTT GAG CTT AAA ATC AAA          1298
Gly Val Leu Ser Val Asn Leu Ser Leu Thr Val Glu Leu Lys Ile Lys
                415                 420                 425

ATT GCT TCA GGA TTC GGG CCA TTG ATC ACA CAC GGT TCA GGG ATG GAC          1346
Ile Ala Ser Gly Phe Gly Pro Leu Ile Thr His Gly Ser Gly Met Asp
                430                 435                 440

CTA TAC AAA ACC AAC CAC AAC AAT GTG TAT TGG CTG ACT ATC CCG CCA          1394
Leu Tyr Lys Thr Asn His Asn Asn Val Tyr Trp Leu Thr Ile Pro Pro
                445                 450                 455

ATG AAG AAC CTA GCC TTA GGT GTA ATC AAC ACA TTG GAG TGG ATA CCG          1442
Met Lys Asn Leu Ala Leu Gly Val Ile Asn Thr Leu Glu Trp Ile Pro
        460                 465                 470

AGA TTC AAG GTT AGT CCC AAC CTC TTC ACT GTT CCA ATC AAG GAA GCA          1490
Arg Phe Lys Val Ser Pro Asn Leu Phe Thr Val Pro Ile Lys Glu Ala
475                 480                 485                 490

GGC GAG GAC TGC CAT GCC CCA ACA TAC CTA CCT GCG GAG GTG GAT GGT          1538
Gly Glu Asp Cys His Ala Pro Thr Tyr Leu Pro Ala Glu Val Asp Gly
                495                 500                 505

GAT GTC AAA CTC AGT TCC AAT CTG GTA ATT CTA CCT GGT CAG GAT CTC          1586
Asp Val Lys Leu Ser Ser Asn Leu Val Ile Leu Pro Gly Gln Asp Leu
        510                 515                 520
```

FIGURE 6

```
CAA TAT GTT TTG GCA ACC TAC GAT ACT TCC AGG GTT GAA CAT GCT GTG      1634
Gln Tyr Val Leu Ala Thr Tyr Asp Thr Ser Arg Val Glu His Ala Val
        525                 530                 535

GTT TAT TAT GTT TAC AGC CCA GGC CGC TCA TTT TCT TAC TTT TAT CCT      1682
Val Tyr Tyr Val Tyr Ser Pro Gly Arg Ser Phe Ser Tyr Phe Tyr Pro
        540                 545                 550

TTT AGG TTG CCT ATA AAG GGG GTC CCA ATC GAA TTA CAA GTG GAA TGC      1730
Phe Arg Leu Pro Ile Lys Gly Val Pro Ile Glu Leu Gln Val Glu Cys
555                 560                 565                 570

TTC ACA TGG GAC CAA AAA CTC TGG TGC CGT CAC TTC TGT GTG CTT GCG      1778
Phe Thr Trp Asp Gln Lys Leu Trp Cys Arg His Phe Cys Val Leu Ala
                575                 580                 585

GAT TCA GAA TCT GGT GGA CAT ATC ACT CAC TCT GGG ATG GTG GGC ATG      1826
Asp Ser Glu Ser Gly Gly His Ile Thr His Ser Gly Met Val Gly Met
                590                 595                 600

GGA GTC AGC TGC ACA GTC ACC CGG GAA GAT GGA ACC AAT CGC AGA TAGGGCTGCT
1881
Gly Val Ser Cys Thr Val Thr Arg Glu Asp Gly Thr Asn Arg Arg
        605                 610                 615

AGTGAACCAA TCTCATGATG TCACCCAGAC ATCAGGCA                             1919
```

FIGURE 7

Wild-Type Isolate Chicago-2 HA Nucleotide and Amino Acid Sequence

```
AGGGTGCAAG ATCATCCACA ATG TCA CCA CAA CGA GAC CGA ATA AAT GCC      50
                     Met Ser Pro Gln Arg Asp Arg Ile Asn Ala
                      1           5                      10

TTC TAC AAA GAC AAC CCC CAT CCT AAG GGA AGT AGG ATA GTT ATT AAC    98
Phe Tyr Lys Asp Asn Pro His Pro Lys Gly Ser Arg Ile Val Ile Asn
            15                  20                      25

AGA GAA CAT CTT ATG ATT GAT AGA CCT TAT GTT TTG CTG GCT GTT CTA   146
Arg Glu His Leu Met Ile Asp Arg Pro Tyr Val Leu Leu Ala Val Leu
                30                  35                      40

TTC GTC ATG TTT CTG AGC TTG ATC GGG TTG CTA GCC ATT GCA GGC ATT   194
Phe Val Met Phe Leu Ser Leu Ile Gly Leu Leu Ala Ile Ala Gly Ile
            45                  50                      55

AGA CTT CAT CGG GCA GCC ATC TAC ACC GCA GAG ATC CAT AAA AGC CTC   242
Arg Leu His Arg Ala Ala Ile Tyr Thr Ala Glu Ile His Lys Ser Leu
        60                  65                  70

AGC ACC AAT CTA GAT GTA ACT AAC TCA ATC GAG CAT CAG GTC AAG GAC   290
Ser Thr Asn Leu Asp Val Thr Asn Ser Ile Glu His Gln Val Lys Asp
75                  80                  85                  90

GTG CTG ACA CCA CTC TTC AAG ATC ATC GGT GAT GAA GTG GGC CTG AGG   338
Val Leu Thr Pro Leu Phe Lys Ile Ile Gly Asp Glu Val Gly Leu Arg
                    95                 100                 105

ACA CCT CAG AGA TTC ACT GAC CTA GTG AAA TTC ATC TCT GAC AAG ATT   386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAC CTC ACT TGG   434
Lys Phe Leu Asn Pro Asp Arg Glu Tyr Asp Phe Arg Asp Leu Thr Trp
            125                 130                 135

TGC ATC AAC CCG CCA GAG AGA ATC AAA TTG GAT TAT GAT CAA TAC TGT   482
Cys Ile Asn Pro Pro Glu Arg Ile Lys Leu Asp Tyr Asp Gln Tyr Cys
        140                 145                 150

GCA GAT GTG GCT GCT GAA GAA CTC ATG AAT GCA TTG GTG AAC TCA ACT   530
Ala Asp Val Ala Ala Glu Glu Leu Met Asn Ala Leu Val Asn Ser Thr
155                 160                 165                 170

CTA CTG GAG GCC AGG ACA ACC AAT CAG TTC CTA GCT GTC TCA AAG GGA   578
Leu Leu Glu Ala Arg Thr Thr Asn Gln Phe Leu Ala Val Ser Lys Gly
                175                 180                 185

AAC TGC TCA GGG CCC ACT ACA ATC AGA GGT CAA TTC TCA AAC ATG TCG   626
Asn Cys Ser Gly Pro Thr Thr Ile Arg Gly Gln Phe Ser Asn Met Ser
                190                 195                 200

CTG TCC CTG TTG GAC TTG TAT TTA AGT CGA GGT TAC AAT GTA TCA TCT   674
Leu Ser Leu Leu Asp Leu Tyr Leu Ser Arg Gly Tyr Asn Val Ser Ser
            205                 210                 215

ATA GTC ACT ATG ACA TCC CAG GGA ATG TAC GGG GGA ACT TAC CTA GTG   722
Ile Val Thr Met Thr Ser Gln Gly Met Tyr Gly Gly Thr Tyr Leu Val
        220                 225                 230

GAA AAA CCT AAT CTG AGC AGT AAA GGG TCA GAG TTG TCA CAA CTG AGC   770
Glu Lys Pro Asn Leu Ser Ser Lys Gly Ser Glu Leu Ser Gln Leu Ser
235                 240                 245                 250
```

FIGURE 7

| | |
|---|---|
| ATG CAT CGA GTG TTT GAA GTA GGT GTT ATC AGA AAT CCG GGT TTG GGG<br>Met His Arg Val Phe Glu Val Gly Val Ile Arg Asn Pro Gly Leu Gly<br>255 260 265 | 818 |
| GCT CCG GTG TTC CAT ATG ACA AAC TAT TTT GAG CAA CCA GTC AGT AAT<br>Ala Pro Val Phe His Met Thr Asn Tyr Phe Glu Gln Pro Val Ser Asn<br>270 275 280 | 866 |
| GAT TTC AGC AAC TGC ATG GTG GCT TTG GGG GAG CTC AAA TTC GCA GCC<br>Asp Phe Ser Asn Cys Met Val Ala Leu Gly Glu Leu Lys Phe Ala Ala<br>285 290 295 | 914 |
| CTC TGT CAC AGG GAA GAT TTT ATC ACA ATT CCC TAT CAG GGG TCA GGG<br>Leu Cys His Arg Glu Asp Phe Ile Thr Ile Pro Tyr Gln Gly Ser Gly<br>300 305 310 | 962 |
| AAA GGT GTC AGC TTC CGG CTC GTC AAG CTA GGT GTC TGG AAA TCT CCA<br>Lys Gly Val Ser Phe Arg Leu Val Lys Leu Gly Val Trp Lys Ser Pro<br>315 320 325 330 | 1010 |
| ACC GAC ATG CAA TCC TGG GTC CCC CTA TCA ACG GAT GAT CCA GTG ATA<br>Thr Asp Met Gln Ser Trp Val Pro Leu Ser Thr Asp Asp Pro Val Ile<br>335 340 345 | 1058 |
| GAT AAG CTT TAC CTC TCA TCT CAC AGG GGT GTT ATC GCT GAC AAT CAA<br>Asp Lys Leu Tyr Leu Ser Ser His Arg Gly Val Ile Ala Asp Asn Gln<br>350 355 360 | 1106 |
| GCA AAA TGG GCT GTC CCG ACA ACA CGG ACA GAT GAC AAG TTG CGA ATG<br>Ala Lys Trp Ala Val Pro Thr Thr Arg Thr Asp Asp Lys Leu Arg Met<br>365 370 375 | 1154 |
| GAG ACA TGC TTC CAG CAG GCG TGT AAG GGT AGA ATC CAA GCA CTC TGC<br>Glu Thr Cys Phe Gln Gln Ala Cys Lys Gly Arg Ile Gln Ala Leu Cys<br>380 385 390 | 1202 |
| GAG AAT CCC GAG TGG GCA CCA TTG AAG GAT AAC AGG ATT CCT TCA TAC<br>Glu Asn Pro Glu Trp Ala Pro Leu Lys Asp Asn Arg Ile Pro Ser Tyr<br>395 400 405 410 | 1250 |
| GGG GTC TTG TCT GTT AAT CTG AGT CTG ACA GTT GAG CTT AAA ATC AAA<br>Gly Val Leu Ser Val Asn Leu Ser Leu Thr Val Glu Leu Lys Ile Lys<br>415 420 425 | 1298 |
| ATT GCT TCA GGA TTC GGG CCA TTG ATC ACA CAC GGT TCA GGG ATG GAC<br>Ile Ala Ser Gly Phe Gly Pro Leu Ile Thr His Gly Ser Gly Met Asp<br>430 435 440 | 1346 |
| CTA TAC AAA TCC AAC CAC AAC AAT GTG TAT TGG CTG ACT ATC CCG CCA<br>Leu Tyr Lys Ser Asn His Asn Asn Val Tyr Trp Leu Thr Ile Pro Pro<br>445 450 455 | 1394 |
| ATG AAG AAC CTA GCC TTA GGT GTA ATC AAC ACA TTG GAG TGG ATA CCG<br>Met Lys Asn Leu Ala Leu Gly Val Ile Asn Thr Leu Glu Trp Ile Pro<br>460 465 470 | 1442 |
| AGA TTC AAG GTT AGT CCC AAC CTC TTC ACT ATT CCA ATC AAG GAA GCA<br>Arg Phe Lys Val Ser Pro Asn Leu Phe Thr Ile Pro Ile Lys Glu Ala<br>475 480 485 490 | 1490 |
| GGC GAG GAC TGC CAT GCC CCA ACA TAC CTC TCT GCG GAG GTG GAT GGT<br>Gly Glu Asp Cys His Ala Pro Thr Tyr Leu Ser Ala Glu Val Asp Gly<br>495 500 505 | 1538 |
| GAT GTC AAA CTC AGT TCC AAT CTG GTA ATT CTA CCT GGC CAA GAT CTC<br>Asp Val Lys Leu Ser Ser Asn Leu Val Ile Leu Pro Gly Gln Asp Leu<br>510 515 520 | 1586 |

FIGURE 7

```
CAA TAT GTT TTG GCA ACC TAC GAT ACT TCC AGG GTT GAA CAT GCT GTG        1634
Gln Tyr Val Leu Ala Thr Tyr Asp Thr Ser Arg Val Glu His Ala Val
    525                 530                 535

GTT TAT TAT GTT TAC AAC CCA AGC CGC TCA TTT TCT TAC TTT TAT CCT        1682
Val Tyr Tyr Val Tyr Asn Pro Ser Arg Ser Phe Ser Tyr Phe Tyr Pro
    540                 545                 550

TTT AGG TTG CCT GTA AAG GGG TTC CCC ATC GAA TTA CAA GTG GAA TGC        1730
Phe Arg Leu Pro Val Lys Gly Phe Pro Ile Glu Leu Gln Val Glu Cys
555                 560                 565                 570

TTC ACA TGG GAC CAA AAA CTC TGG TGC CGT CAC TTC TGT GTG CTT GCG        1778
Phe Thr Trp Asp Gln Lys Leu Trp Cys Arg His Phe Cys Val Leu Ala
                575                 580                 585

GAC TCA GAA TCT GGT GGA CAT ATC ACT CAC TCT GGG ATG GTG GGC ATG        1826
Asp Ser Glu Ser Gly Gly His Ile Thr His Ser Gly Met Val Gly Met
                590                 595                 600

GGA GTC AGC TGC ACA GTC ACC CGG GAA GAT GGA ACC AAT CGC AGA TAGGGCTGCT
1881
Gly Val Ser Cys Thr Val Thr Arg Glu Asp Gly Thr Asn Arg Arg
    605                 610                 615

AGTGAACCAA TCTCATGATG TCACCCAGAC ATCAGGCA                               1919
```

FIGURE 8

Wild-Type Isolate McI HA Nucleotide and Amino Acid Sequence

```
AGGGTGCAAG ATCATCCACA ATG TCA CCA CAA CGA GAC CGG ATA AAT GCC          50
                     Met Ser Pro Gln Arg Asp Arg Ile Asn Ala
                      1           5                      10

TTC TAC AAA GAC AAC CCC CAT CCT AGG GGA AGT AGG ATA GTT ATT AAC        98
Phe Tyr Lys Asp Asn Pro His Pro Arg Gly Ser Arg Ile Val Ile Asn
            15                  20                  25

AGA GAA CAT CTT ATG ATT GAT AGA CCT TAT GTT TTG CTG GCT GTT CTA       146
Arg Glu His Leu Met Ile Asp Arg Pro Tyr Val Leu Leu Ala Val Leu
            30                  35                  40

TTC GTC ATG TTT CTG AGC TTG ATC GGG TTG CTA GCC ATT GCA GGC ATA       194
Phe Val Met Phe Leu Ser Leu Ile Gly Leu Leu Ala Ile Ala Gly Ile
            45                  50                  55

AGA CTT CAT CGG GCA GCC ATC TAC ACC GCA GAG ATC CAT AAA AGC CTC       242
Arg Leu His Arg Ala Ala Ile Tyr Thr Ala Glu Ile His Lys Ser Leu
        60                  65                  70

AGC ACC AAT CTA GAT GTA ACT AAC TCA ATC GAG CAT CAG GTC AAG GAC       290
Ser Thr Asn Leu Asp Val Thr Asn Ser Ile Glu His Gln Val Lys Asp
75                  80                  85                  90

GTG CTG ACA CCA CTC TTC AAG ATC ATC GGT GAT GAA GTG GGC CTG AGG       338
Val Leu Thr Pro Leu Phe Lys Ile Ile Gly Asp Glu Val Gly Leu Arg
                95                  100                 105

ACA CCT CAG AGA TTC ACC GAC CTA GTG AAA TTC ATC TCT GAC AAG ATT       386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAT CTC ACT TGG       434
Lys Phe Leu Asn Pro Asp Arg Glu Tyr Asp Phe Arg Asp Leu Thr Trp
        125                 130                 135

TGT ATC AAC CCG CCA GAG AGA ATC AAA TTG GAT TAT GAT CAA TAC TGT       482
Cys Ile Asn Pro Pro Glu Arg Ile Lys Leu Asp Tyr Asp Gln Tyr Cys
    140                 145                 150

GCA GAT GTG GCT GCT GAA GAA CTC ATG AAT GCA TTG GTG AAC TCA ACT       530
Ala Asp Val Ala Ala Glu Glu Leu Met Asn Ala Leu Val Asn Ser Thr
155                 160                 165                 170

CTA CTG GAG GCC AGG GTA ACC AAT CAG TTC CTA GCT GTC TCA AAG GGA       578
Leu Leu Glu Ala Arg Val Thr Asn Gln Phe Leu Ala Val Ser Lys Gly
                175                 180                 185

AAC TGC TCA GGG CCC ACT ACA ATC AGA GGT CAA TTC TCA AAC ATG TCG       626
Asn Cys Ser Gly Pro Thr Thr Ile Arg Gly Gln Phe Ser Asn Met Ser
            190                 195                 200

CTG TCC CTG TTG GAC TTG TAT TTA AAT CGA GGT TAC AAT GTG TCA TCT       674
Leu Ser Leu Leu Asp Leu Tyr Leu Asn Arg Gly Tyr Asn Val Ser Ser
        205                 210                 215

ATA GTC ACT ATG ACA TCC CAG GGA ATG TAC GGG GGA ACT TAC CTA GTG       722
Ile Val Thr Met Thr Ser Gln Gly Met Tyr Gly Gly Thr Tyr Leu Val
    220                 225                 230

GAA AAG CCT AAT CTG AGC AGT AAA GGG TCA GAG TTG TCA CAA CTG AGC       770
Glu Lys Pro Asn Leu Ser Ser Lys Gly Ser Glu Leu Ser Gln Leu Ser
235                 240                 245                 250
```

FIGURE 8

```
ATG CAC CGA GTG TTT GAA GTA GGT GTT ATC AGA AAT CCG GGT TTG GGG     818
Met His Arg Val Phe Glu Val Gly Val Ile Arg Asn Pro Gly Leu Gly
            255             260             265

GCT CCG GTG TTC CAT ATG ACA AAC TAT TTT GAG CAA CCA GTC AGT AAT     866
Ala Pro Val Phe His Met Thr Asn Tyr Phe Glu Gln Pro Val Ser Asn
            270             275             280

GAT TTC AGC AAC TGC ATG GTG GCT TTG GGG GAG CTC AAA TTC GCA GCC     914
Asp Phe Ser Asn Cys Met Val Ala Leu Gly Glu Leu Lys Phe Ala Ala
            285             290             295

CTT TGT CAC AGG GAA GAT TCT ATC ACA ATT CCC TAT CAG GGA TCA GGG     962
Leu Cys His Arg Glu Asp Ser Ile Thr Ile Pro Tyr Gln Gly Ser Gly
            300             305             310

AAA GGT GTC AGC TTC CAG CTC GTC AAG CTA GGT GTC TGG AAA TCC CCA    1010
Lys Gly Val Ser Phe Gln Leu Val Lys Leu Gly Val Trp Lys Ser Pro
315             320             325             330

ACC GAC ATG CAA TCC TGG GTC CCC CTA TCA ACG GAT GAT CCA GTG ATA    1058
Thr Asp Met Gln Ser Trp Val Pro Leu Ser Thr Asp Asp Pro Val Ile
            335             340             345

GAC AGG CTC TAC CTC TCA TCT CAC AGA GGC GTT ATC GCT GAC AAT CAA    1106
Asp Arg Leu Tyr Leu Ser Ser His Arg Gly Val Ile Ala Asp Asn Gln
            350             355             360

GCA AAA TGG GCT GTC CCG ACA ACA CGG ACA GAT GAC AAG TTG CGA ATG    1154
Ala Lys Trp Ala Val Pro Thr Thr Arg Thr Asp Asp Lys Leu Arg Met
            365             370             375

GAG ACA TGC TTC CAG CAG GCG TGT AAG GGT AAA ATC CAA GCA CTC TGC    1202
Glu Thr Cys Phe Gln Gln Ala Cys Lys Gly Lys Ile Gln Ala Leu Cys
            380             385             390

GAG AAT CCC GAG TGG GCA CCA TTG AAG GAT AAC AGG ATT CCT TCA TAC    1250
Glu Asn Pro Glu Trp Ala Pro Leu Lys Asp Asn Arg Ile Pro Ser Tyr
395             400             405             410

GGG GTC TTG TCT GTT AAT CTG AGT CTG ACA GTT GAG CTT AAA ATC AAA    1298
Gly Val Leu Ser Val Asn Leu Ser Leu Thr Val Glu Leu Lys Ile Lys
            415             420             425

ATT GCT TCA GGA TTC GGG CCA TTG ATC ACA CAC GGT TCA GGG ATG GAC    1346
Ile Ala Ser Gly Phe Gly Pro Leu Ile Thr His Gly Ser Gly Met Asp
            430             435             440

CTA TAC AAA TCC AAC CAC AAC AAT GTG TAT TGG CTG ACT ATC CCG CCA    1394
Leu Tyr Lys Ser Asn His Asn Asn Val Tyr Trp Leu Thr Ile Pro Pro
            445             450             455

ATG AAG AAC CTA GCC TTA GGT GTA ATC AAC ACA TTG GAG TGG ATA CCG    1442
Met Lys Asn Leu Ala Leu Gly Val Ile Asn Thr Leu Glu Trp Ile Pro
            460             465             470

AGA TTC AAG GTT AGT CCC AAC CTC TTC ACT GTT CCA ATT AAG GAA GCA    1490
Arg Phe Lys Val Ser Pro Asn Leu Phe Thr Val Pro Ile Lys Glu Ala
475             480             485             490

GGC GAG GAC TGC CAT GCC CCA ACA TAC CTA CCT GCG GAG GTG GAT GGT    1538
Gly Glu Asp Cys His Ala Pro Thr Tyr Leu Pro Ala Glu Val Asp Gly
            495             500             505

GAT GTC AAA CTC AGT TCC AAT CTG GTG ATT CTA CCT GGT CAA GAT CTC    1586
Asp Val Lys Leu Ser Ser Asn Leu Val Ile Leu Pro Gly Gln Asp Leu
            510             515             520
```

FIGURE 8

```
CAA TAT GTT TTG GCA ACC TAT GAT ACT TCC AGA GTT GAA CAT GCT GTG        1634
Gln Tyr Val Leu Ala Thr Tyr Asp Thr Ser Arg Val Glu His Ala Val
        525                 530                 535

GTT TAT TAC GTT TAC AGC CCA AGC CGC TCA TTT TCT TAC TTT TAT CCT        1682
Val Tyr Tyr Val Tyr Ser Pro Ser Arg Ser Phe Ser Tyr Phe Tyr Pro
        540                 545                 550

TTT AGG TTG CCT ATA AGG GGG GTC CCC ATC GAA TTA CAA GTG GAA TGC        1730
Phe Arg Leu Pro Ile Arg Gly Val Pro Ile Glu Leu Gln Val Glu Cys
555                 560                 565                 570

TTC ACA TGG GAC CAA AAA CTC TGG TGC CGT CAC TTC TGT GTG CTT GCG        1778
Phe Thr Trp Asp Gln Lys Leu Trp Cys Arg His Phe Cys Val Leu Ala
                575                 580                 585

GAC TCA GAA TCT GGT GGA TAT ATC ACT CAC TCT GGG ATG GTG GGC ATG        1826
Asp Ser Glu Ser Gly Gly Tyr Ile Thr His Ser Gly Met Val Gly Met
        590                 595                 600

GGA GTC AGC TGC ACA GTC ACC CGG GAA GAT GGA ACC AAC CGC AGA TAGGGCTGCT
1881
Gly Val Ser Cys Thr Val Thr Arg Glu Asp Gly Thr Asn Arg Arg
        605                 610                 615

AGTGAACCAA TCTCATGATG TCACCCAGAC ATCAGGCA                              1919
```

FIGURE 9

Wild-Type Isolate JM HA nucleotide and Amino Acid Sequence

```
AGGGTGCAAG ATCATCCACA ATG TCA CCA CAA CGA GAC CGG ATA AAT GCC         50
                     Met Ser Pro Gln Arg Asp Arg Ile Asn Ala
                      1           5                      10

TTC TAC AAA GAT AAC CCC CAT CCC AAG GGA AGT AGG ATA GTT ATC AAC        98
Phe Tyr Lys Asp Asn Pro His Pro Lys Gly Ser Arg Ile Val Ile Asn
             15                  20                  25

AGA GAA CAC CTT ATG ATT GAT AGA CCT TAT GTT TTG CTG GCT GTT CTG       146
Arg Glu His Leu Met Ile Asp Arg Pro Tyr Val Leu Leu Ala Val Leu
             30                  35                  40

TTC GTC ATG TTT CTG AGC TTG ATC GGG TTG CTA GCC ATT GCA GGC ATT       194
Phe Val Met Phe Leu Ser Leu Ile Gly Leu Leu Ala Ile Ala Gly Ile
             45                  50                  55

AGA CTT CAT CGG GCA GCC ATC TAC ACC GCA GAG ATC CAT AAA AGC CTC       242
Arg Leu His Arg Ala Ala Ile Tyr Thr Ala Glu Ile His Lys Ser Leu
     60                  65                  70

AGC ACC AAT CTA GAT GTA ACT AAC TCA ATT GAG CAT CAG GTC AAG GAC       290
Ser Thr Asn Leu Asp Val Thr Asn Ser Ile Glu His Gln Val Lys Asp
75                  80                  85                  90

GTG CTG ACA CCA CTC TTC AAA ATC ATC GGT GAT GAA GTG GGC CTG AGG       338
Val Leu Thr Pro Leu Phe Lys Ile Ile Gly Asp Glu Val Gly Leu Arg
                 95                 100                 105

ACA CCT CAG AGA TTC ACT GAC CTA GTG AAA TTC ATC TCT GAC AAG ATT       386
Thr Pro Gln Arg Phe Thr Asp Leu Val Lys Phe Ile Ser Asp Lys Ile
             110                 115                 120

AAA TTC CTT AAC CCG GAT AGG GAG TAC GAC TTC AGA GAT CTC ACT TGG       434
Lys Phe Leu Asn Pro Asp Arg Glu Tyr Asp Phe Arg Asp Leu Thr Trp
             125                 130                 135

TGT ATC AAC CCG CCA GAG AGA ATC AAA TTG GAT TAT GAT CAA TAC TGT       482
Cys Ile Asn Pro Pro Glu Arg Ile Lys Leu Asp Tyr Asp Gln Tyr Cys
    140                 145                 150

GCA GAT GTG GCT GCT GAA GAG CTC ATG AAT GCA TTG GTG AAC TCA ACT       530
Ala Asp Val Ala Ala Glu Glu Leu Met Asn Ala Leu Val Asn Ser Thr
155                 160                 165                 170

CTA CTG GAG ACC AGA ACA ACC AAT CAG TTC CTA GCT GTC TCA AAG GGA       578
Leu Leu Glu Thr Arg Thr Thr Asn Gln Phe Leu Ala Val Ser Lys Gly
                 175                 180                 185

AAC TGC TCA GGG CCC ACT ACA ATC AGA GGT CAA TTC TCA AAC ATG TCG       626
Asn Cys Ser Gly Pro Thr Thr Ile Arg Gly Gln Phe Ser Asn Met Ser
             190                 195                 200

CTG TCC CTG TTG GAC TTG TAT TTA AGT CGA GGT TAC AAT GTG TCA TCT       674
Leu Ser Leu Leu Asp Leu Tyr Leu Ser Arg Gly Tyr Asn Val Ser Ser
         205                 210                 215

ATA GTC ACT ATG ACA TCC CAG GGA ATG TAC GGG GGA ACT TAC CTA GTG       722
Ile Val Thr Met Thr Ser Gln Gly Met Tyr Gly Gly Thr Tyr Leu Val
    220                 225                 230

GAA AAG CCT AAT CTG AGC AGC AAA GGG TCA GAG TTG TCA CAA CTG AGC       770
Glu Lys Pro Asn Leu Ser Ser Lys Gly Ser Glu Leu Ser Gln Leu Ser
235                 240                 245                 250
```

FIGURE 9

| | | | | | | | | | | | | | | | | |
|---|---|---|---|---|---|---|---|---|---|---|---|---|---|---|---|---|
| ATG | TAC | CGA | GTG | TTT | GAA | GTA | GGT | GTT | ATC | AGA | AAT | CCG | GGT | TTG | GGG | 818 |
| Met | Tyr | Arg | Val | Phe | Glu | Val | Gly | Val | Ile | Arg | Asn | Pro | Gly | Leu | Gly | |
| | | | | 255 | | | | | 260 | | | | | 265 | | |

| | | | | | | | | | | | | | | | | |
|---|---|---|---|---|---|---|---|---|---|---|---|---|---|---|---|---|
| GCT | CCG | GTG | TTC | CAT | ATG | ACA | AAC | TAT | TTT | GAG | CAA | CCA | GTC | AGT | AAT | 866 |
| Ala | Pro | Val | Phe | His | Met | Thr | Asn | Tyr | Phe | Glu | Gln | Pro | Val | Ser | Asn | |
| | | | 270 | | | | | 275 | | | | | 280 | | | |

| | | | | | | | | | | | | | | | | |
|---|---|---|---|---|---|---|---|---|---|---|---|---|---|---|---|---|
| GAT | CTC | AGC | AAC | TGT | ATG | GTG | GCT | TTG | GGG | GAG | CTC | AAA | CTC | GCA | GCC | 914 |
| Asp | Leu | Ser | Asn | Cys | Met | Val | Ala | Leu | Gly | Glu | Leu | Lys | Leu | Ala | Ala | |
| | | 285 | | | | | 290 | | | | | 295 | | | | |

| | | | | | | | | | | | | | | | | |
|---|---|---|---|---|---|---|---|---|---|---|---|---|---|---|---|---|
| CTT | TGT | CAC | GGG | GGA | GAT | TCT | ATC | ACA | ATT | CCC | TAT | CAG | GGA | TCA | GGG | 962 |
| Leu | Cys | His | Gly | Gly | Asp | Ser | Ile | Thr | Ile | Pro | Tyr | Gln | Gly | Ser | Gly | |
| | 300 | | | | | 305 | | | | | 310 | | | | | |

| | | | | | | | | | | | | | | | | |
|---|---|---|---|---|---|---|---|---|---|---|---|---|---|---|---|---|
| AAA | GGT | GTC | AGC | TTT | CAG | CTC | GTC | AAG | CTA | GGT | GTC | TGG | AAA | TCC | CCA | 1010 |
| Lys | Gly | Val | Ser | Phe | Gln | Leu | Val | Lys | Leu | Gly | Val | Trp | Lys | Ser | Pro | |
| 315 | | | | | 320 | | | | | 325 | | | | | 330 | |

| | | | | | | | | | | | | | | | | |
|---|---|---|---|---|---|---|---|---|---|---|---|---|---|---|---|---|
| ACC | GAC | ATG | CAA | TCC | TGG | GTC | CCC | TTC | TCA | ACG | GAT | GAC | CCA | GTG | ATA | 1058 |
| Thr | Asp | Met | Gln | Ser | Trp | Val | Pro | Phe | Ser | Thr | Asp | Asp | Pro | Val | Ile | |
| | | | | 335 | | | | | 340 | | | | | 345 | | |

| | | | | | | | | | | | | | | | | |
|---|---|---|---|---|---|---|---|---|---|---|---|---|---|---|---|---|
| GAC | AGG | CTT | TAC | CTC | TCA | TCT | CAC | AGA | GGT | GTT | ATC | GCT | GAC | AAT | CAA | 1106 |
| Asp | Arg | Leu | Tyr | Leu | Ser | Ser | His | Arg | Gly | Val | Ile | Ala | Asp | Asn | Gln | |
| | | | 350 | | | | | 355 | | | | | 360 | | | |

| | | | | | | | | | | | | | | | | |
|---|---|---|---|---|---|---|---|---|---|---|---|---|---|---|---|---|
| GCA | AAA | TGG | GCT | ATC | CCG | ACA | ACA | AGA | ACA | GAT | GAC | AAG | TTG | CGA | ATG | 1154 |
| Ala | Lys | Trp | Ala | Ile | Pro | Thr | Thr | Arg | Thr | Asp | Asp | Lys | Leu | Arg | Met | |
| | | 365 | | | | | 370 | | | | | 375 | | | | |

| | | | | | | | | | | | | | | | | |
|---|---|---|---|---|---|---|---|---|---|---|---|---|---|---|---|---|
| GAG | ACA | TGC | TTC | CAG | CAG | GCG | TGT | AAG | GGT | AAA | ATC | CAA | GCA | CTC | TGC | 1202 |
| Glu | Thr | Cys | Phe | Gln | Gln | Ala | Cys | Lys | Gly | Lys | Ile | Gln | Ala | Leu | Cys | |
| | 380 | | | | | 385 | | | | | 390 | | | | | |

| | | | | | | | | | | | | | | | | |
|---|---|---|---|---|---|---|---|---|---|---|---|---|---|---|---|---|
| GAG | AAT | CCC | GAG | TGG | GCA | CCA | TTG | AAG | GAT | AAC | AGG | ATT | CCT | TCA | TAC | 1250 |
| Glu | Asn | Pro | Glu | Trp | Ala | Pro | Leu | Lys | Asp | Asn | Arg | Ile | Pro | Ser | Tyr | |
| 395 | | | | 400 | | | | | 405 | | | | | 410 | | |

| | | | | | | | | | | | | | | | | |
|---|---|---|---|---|---|---|---|---|---|---|---|---|---|---|---|---|
| GGA | GTC | TTG | TCT | GTT | GAT | CTG | AGT | CTA | ACA | GTT | GAG | CTT | AAA | ATC | AAA | 1298 |
| Gly | Val | Leu | Ser | Val | Asp | Leu | Ser | Leu | Thr | Val | Glu | Leu | Lys | Ile | Lys | |
| | | | | 415 | | | | | 420 | | | | | 425 | | |

| | | | | | | | | | | | | | | | | |
|---|---|---|---|---|---|---|---|---|---|---|---|---|---|---|---|---|
| ATT | GCT | TCG | GGA | TTC | GGG | CCA | TTG | ATC | ACA | CAC | GGT | TCA | GGG | ATG | GAC | 1346 |
| Ile | Ala | Ser | Gly | Phe | Gly | Pro | Leu | Ile | Thr | His | Gly | Ser | Gly | Met | Asp | |
| | | | 430 | | | | | 435 | | | | | 440 | | | |

| | | | | | | | | | | | | | | | | |
|---|---|---|---|---|---|---|---|---|---|---|---|---|---|---|---|---|
| CTA | TAC | AAG | TCC | AAC | CAC | AAC | AAT | GAG | TAT | TGG | CTG | ACT | ATC | CCG | CCA | 1394 |
| Leu | Tyr | Lys | Ser | Asn | His | Asn | Asn | Glu | Tyr | Trp | Leu | Thr | Ile | Pro | Pro | |
| | | 445 | | | | | 450 | | | | | 455 | | | | |

| | | | | | | | | | | | | | | | | |
|---|---|---|---|---|---|---|---|---|---|---|---|---|---|---|---|---|
| ATG | AAG | AAC | CTA | GCC | CTA | GGT | GTA | ATC | AAC | ACA | TTG | GAG | TGG | ATA | CCG | 1442 |
| Met | Lys | Asn | Leu | Ala | Leu | Gly | Val | Ile | Asn | Thr | Leu | Glu | Trp | Ile | Pro | |
| | 460 | | | | | 465 | | | | | 470 | | | | | |

| | | | | | | | | | | | | | | | | |
|---|---|---|---|---|---|---|---|---|---|---|---|---|---|---|---|---|
| AGA | TTC | AAG | GTT | AGT | CCC | AAC | CTC | TTC | ACT | GTC | CCA | ATT | AAG | GAA | GCA | 1490 |
| Arg | Phe | Lys | Val | Ser | Pro | Asn | Leu | Phe | Thr | Val | Pro | Ile | Lys | Glu | Ala | |
| 475 | | | | | 480 | | | | | 485 | | | | | 490 | |

| | | | | | | | | | | | | | | | | |
|---|---|---|---|---|---|---|---|---|---|---|---|---|---|---|---|---|
| GGC | GAA | GAC | TGC | CAT | GCC | CCA | ACA | TAC | CTA | CCT | GCG | GAG | GTG | GAT | GGT | 1538 |
| Gly | Glu | Asp | Cys | His | Ala | Pro | Thr | Tyr | Leu | Pro | Ala | Glu | Val | Asp | Gly | |
| | | | | 495 | | | | | 500 | | | | | 505 | | |

| | | | | | | | | | | | | | | | | |
|---|---|---|---|---|---|---|---|---|---|---|---|---|---|---|---|---|
| GAT | GTC | AAA | CTC | AGT | TCC | AAT | CTG | GTG | ATC | CTA | CCT | GGT | CAA | GAT | CTC | 1586 |
| Asp | Val | Lys | Leu | Ser | Ser | Asn | Leu | Val | Ile | Leu | Pro | Gly | Gln | Asp | Leu | |
| | | | 510 | | | | | 515 | | | | | 520 | | | |

FIGURE 9

```
CAA TAT GTT TTG GCA ACC TAC GAT ACT TCC AGG GTT GAA CAT GCT GTG      1634
Gln Tyr Val Leu Ala Thr Tyr Asp Thr Ser Arg Val Glu His Ala Val
        525             530             535

GTT TAT TAC GTT TAC AGC CCA AGC CGC TCA TTT TCT TAC TTT TAT CCT      1682
Val Tyr Tyr Val Tyr Ser Pro Ser Arg Ser Phe Ser Tyr Phe Tyr Pro
        540             545             550

TTT AGG TTG CCT ATA AAG GGG ATC CCC ATC GAA TTA CAA GTG GAA TGC      1730
Phe Arg Leu Pro Ile Lys Gly Ile Pro Ile Glu Leu Gln Val Glu Cys
555             560             565             570

TTC ACA TGG GAC CAA AAA CTC TGG TGC CGT CAC TTC TGT GTG CTT GCG      1778
Phe Thr Trp Asp Gln Lys Leu Trp Cys Arg His Phe Cys Val Leu Ala
        575             580             585

GAC TCA GAA TCT GGT GGA CAT ATC ACT CAC TCT GGG ATG GTG GGC ATG      1826
Asp Ser Glu Ser Gly Gly His Ile Thr His Ser Gly Met Val Gly Met
        590             595             600

GGA GTC AGC TGC ACA GTC ACC CGG GAA GAT GGA ACC AAT AGC AGA TAGGGCTGCT
1881
Gly Val Ser Cys Thr Val Thr Arg Glu Asp Gly Thr Asn Ser Arg
        605             610             615

AGTGAACCAA TCTCATGATG TCACCCAGAC ATCAGGCA                            1919
```

FIGURE 10

Moraten Fusion Nucleotide and Amino Acid Sequence

| | | |
|---|---|---|
| CATCCAATGT CCATC ATG GGT CTC AAG GTG AAC GTC TCT GCC ATA TTC ATG<br>                    Met Gly Leu Lys Val Asn Val Ser Ala Ile Phe Met<br>                     1                5                        10 | 51 |
| GCA GTA CTG TTA ACT CTC CAA ACA CCC ACC GGT CAA ATC CAT TGG GGC<br>Ala Val Leu Leu Thr Leu Gln Thr Pro Thr Gly Gln Ile His Trp Gly<br>         15                20                    25 | 99 |
| AAT CTC TCT AAG ATA GGG GTG GTA GGA ATA GGA AGT GCA AGC TAC AAA<br>Asn Leu Ser Lys Ile Gly Val Val Gly Ile Gly Ser Ala Ser Tyr Lys<br>     30               35                40 | 147 |
| GTT ATG ACT CGT TCC AGC CAT CAA TCA TTA GTC ATA AAA TTA ATG CCC<br>Val Met Thr Arg Ser Ser His Gln Ser Leu Val Ile Lys Leu Met Pro<br>45               50               55                60 | 195 |
| AAT ATA ACT CTC CTC AAT AAC TGC ACG AGG GTA GAG ATT GCA GAA TAC<br>Asn Ile Thr Leu Leu Asn Asn Cys Thr Arg Val Glu Ile Ala Glu Tyr<br>             65                70               75 | 243 |
| AGG AGA CTA CTG AGA ACA GTT TTG GAA CCA ATT AGA GAT GCA CTT AAT<br>Arg Arg Leu Leu Arg Thr Val Leu Glu Pro Ile Arg Asp Ala Leu Asn<br>         80                85                90 | 291 |
| GCA ATG ACC CAG AAT ATA AGA CCG GTT CAG AGT GTA GCT TCA AGT AGG<br>Ala Met Thr Gln Asn Ile Arg Pro Val Gln Ser Val Ala Ser Ser Arg<br>             95              100             105 | 339 |
| AGA CAC AAG AGA TTT GCG GGA GTA GTC CTG GCA GGT GCG GCC CTA GGC<br>Arg His Lys Arg Phe Ala Gly Val Val Leu Ala Gly Ala Ala Leu Gly<br>110                  115               120 | 387 |
| GTT GCC ACA GCT GCT CAG ATA ACA GCC GGC ATT GCA CTT CAC CAG TCC<br>Val Ala Thr Ala Ala Gln Ile Thr Ala Gly Ile Ala Leu His Gln Ser<br>125              130               135             140 | 435 |
| ATG CTG AAC TCT CAA GCC ATC GAC AAT CTG AGA GCG AGC CTG GAA ACT<br>Met Leu Asn Ser Gln Ala Ile Asp Asn Leu Arg Ala Ser Leu Glu Thr<br>             145              150             155 | 483 |
| ACT AAT CAG GCA ATT GAG ACA ATC AGA CAA GCA GGG CAG GAG ATG ATA<br>Thr Asn Gln Ala Ile Glu Thr Ile Arg Gln Ala Gly Gln Glu Met Ile<br>         160                165               170 | 531 |
| TTG GCT GTT CAG GGT GTC CAA GAC TAC ATC AAT AAT GAG CTG ATA CCG<br>Leu Ala Val Gln Gly Val Gln Asp Tyr Ile Asn Asn Glu Leu Ile Pro<br>             175              180             185 | 579 |
| TCT ATG AAC CAA CTA TCT TGT GAT TTA ATC GGC CAG AAG CTC GGG CTC<br>Ser Met Asn Gln Leu Ser Cys Asp Leu Ile Gly Gln Lys Leu Gly Leu<br>         190                195             200 | 627 |
| AAA TTG CTC AGA TAC TAT ACA GAA ATC CTG TCA TTA TTT GGC CCC AGT<br>Lys Leu Leu Arg Tyr Tyr Thr Glu Ile Leu Ser Leu Phe Gly Pro Ser<br>205                  210               215             220 | 675 |
| TTA CGG GAC CCC ATA TCT GCG GAG ATA TCT ATC CAG GCT TTG AGC TAT<br>Leu Arg Asp Pro Ile Ser Ala Glu Ile Ser Ile Gln Ala Leu Ser Tyr<br>             225              230             235 | 723 |
| GCG CTT GGA GGA GAC ATC AAT AAG GTG TTA GAA AAG CTC GGA TAC AGT<br>Ala Leu Gly Gly Asp Ile Asn Lys Val Leu Glu Lys Leu Gly Tyr Ser<br>         240                245             250 | 771 |

FIGURE 10

| | | | | | | | | | | | | | | | | |
|---|---|---|---|---|---|---|---|---|---|---|---|---|---|---|---|---|
| GGA | GGT | GAT | TTA | CTG | GGC | ATC | TTA | GAG | AGC | GGA | GGA | ATA | AAG | GCC | CGG | 819 |
| Gly | Gly | Asp | Leu | Leu | Gly | Ile | Leu | Glu | Ser | Gly | Gly | Ile | Lys | Ala | Arg | |
| | | 255 | | | | 260 | | | | | | 265 | | | | |
| ATA | ACT | CAC | GTC | GAC | ACA | GAG | TCC | TAC | TTC | ATT | GTC | CTC | AGT | ATA | GCC | 867 |
| Ile | Thr | His | Val | Asp | Thr | Glu | Ser | Tyr | Phe | Ile | Val | Leu | Ser | Ile | Ala | |
| | | 270 | | | | 275 | | | | | | 280 | | | | |
| TAT | CCG | ACG | CTG | TCC | GAG | ATT | AAG | GGG | GTG | ATT | GTC | CAC | CGG | CTA | GAG | 915 |
| Tyr | Pro | Thr | Leu | Ser | Glu | Ile | Lys | Gly | Val | Ile | Val | His | Arg | Leu | Glu | |
| 285 | | | | | 290 | | | | | 295 | | | | | 300 | |
| GGG | GTC | TCG | TAC | AAC | ATA | GGC | TCT | CAA | GAG | TGG | TAT | ACC | ACT | GTG | CCC | 963 |
| Gly | Val | Ser | Tyr | Asn | Ile | Gly | Ser | Gln | Glu | Trp | Tyr | Thr | Thr | Val | Pro | |
| | | | | 305 | | | | | 310 | | | | | 315 | | |
| AAG | TAT | GTT | GCA | ACC | CAA | GGG | TAC | CTT | ATC | TCG | AAT | TTT | GAT | GAG | TCA | 1011 |
| Lys | Tyr | Val | Ala | Thr | Gln | Gly | Tyr | Leu | Ile | Ser | Asn | Phe | Asp | Glu | Ser | |
| | | | | 320 | | | | | 325 | | | | | 330 | | |
| TCG | TGT | ACT | TTC | ATG | CCA | GAG | GGG | ACT | GTG | TGC | AGC | CAA | AAT | GCC | TTG | 1059 |
| Ser | Cys | Thr | Phe | Met | Pro | Glu | Gly | Thr | Val | Cys | Ser | Gln | Asn | Ala | Leu | |
| | | 335 | | | | 340 | | | | | | 345 | | | | |
| TAC | CCG | ATG | AGT | CCT | CTG | CTC | CAA | GAA | TGC | CTC | CGG | GGG | TAC | ACC | AAG | 1107 |
| Tyr | Pro | Met | Ser | Pro | Leu | Leu | Gln | Glu | Cys | Leu | Arg | Gly | Tyr | Thr | Lys | |
| | | 350 | | | | 355 | | | | | | 360 | | | | |
| TCC | TGT | GCT | CGT | ACA | CTC | GTA | TCC | GGG | TCT | TTT | GGG | AAC | CGG | TTC | ATT | 1155 |
| Ser | Cys | Ala | Arg | Thr | Leu | Val | Ser | Gly | Ser | Phe | Gly | Asn | Arg | Phe | Ile | |
| 365 | | | | | 370 | | | | | 375 | | | | | 380 | |
| TTA | TCA | CAA | GGG | AAC | CTA | ATA | GCC | AAT | TGT | GCA | TCA | ATC | CTT | TGC | AAG | 1203 |
| Leu | Ser | Gln | Gly | Asn | Leu | Ile | Ala | Asn | Cys | Ala | Ser | Ile | Leu | Cys | Lys | |
| | | | | 385 | | | | | 390 | | | | | 395 | | |
| TGT | TAC | ACA | ACA | GGA | ACG | ATC | ATT | AAT | CAA | GAC | CCT | GAC | AAG | ATC | CTA | 1251 |
| Cys | Tyr | Thr | Thr | Gly | Thr | Ile | Ile | Asn | Gln | Asp | Pro | Asp | Lys | Ile | Leu | |
| | | | 400 | | | | | 405 | | | | | 410 | | | |
| ACA | TAC | ATT | GCT | GCC | GAT | CAC | TGC | CCG | GTA | GTC | GAG | GTG | AAC | GGC | GTG | 1299 |
| Thr | Tyr | Ile | Ala | Ala | Asp | His | Cys | Pro | Val | Val | Glu | Val | Asn | Gly | Val | |
| | | 415 | | | | 420 | | | | | | 425 | | | | |
| ACC | ATC | CAA | GTC | GGG | AGC | AGG | AGG | TAT | CCA | GAC | GCT | GTG | TAC | TTG | CAC | 1347 |
| Thr | Ile | Gln | Val | Gly | Ser | Arg | Arg | Tyr | Pro | Asp | Ala | Val | Tyr | Leu | His | |
| | | 430 | | | | 435 | | | | | | 440 | | | | |
| AGA | ATT | GAC | CTC | GGT | CCT | CCC | ATA | TCA | TTG | GAG | AGG | TTG | GAC | GTA | GGG | 1395 |
| Arg | Ile | Asp | Leu | Gly | Pro | Pro | Ile | Ser | Leu | Glu | Arg | Leu | Asp | Val | Gly | |
| 445 | | | | | 450 | | | | | 455 | | | | | 460 | |
| ACA | AAT | CTG | GGG | AAT | GCA | ATT | GCT | AAG | TTG | GAG | GAT | GCC | AAG | GAA | TTG | 1443 |
| Thr | Asn | Leu | Gly | Asn | Ala | Ile | Ala | Lys | Leu | Glu | Asp | Ala | Lys | Glu | Leu | |
| | | | | 465 | | | | | 470 | | | | | 475 | | |
| TTG | GAG | TCA | TCG | GAC | CAG | ATA | TTG | AGG | AGT | ATG | AAA | GGT | TTA | TCG | AGC | 1491 |
| Leu | Glu | Ser | Ser | Asp | Gln | Ile | Leu | Arg | Ser | Met | Lys | Gly | Leu | Ser | Ser | |
| | | | 480 | | | | | 485 | | | | | 490 | | | |
| ACT | AGC | ATA | GTC | TAC | ATC | CTG | ATT | GCA | GTG | TGT | CTT | GGA | GGG | TTG | ATA | 1539 |
| Thr | Ser | Ile | Val | Tyr | Ile | Leu | Ile | Ala | Val | Cys | Leu | Gly | Gly | Leu | Ile | |
| | | 495 | | | | 500 | | | | | | 505 | | | | |
| GGG | ATC | CCC | GCT | TTA | ATA | TGT | TGC | TGC | AGG | GGG | CGT | TGT | AAC | AAA | AAG | 1587 |
| Gly | Ile | Pro | Ala | Leu | Ile | Cys | Cys | Cys | Arg | Gly | Arg | Cys | Asn | Lys | Lys | |
| | | 510 | | | | 515 | | | | | | 520 | | | | |

FIGURE 10

```
GGA GAA CAA GTT GGT ATG TCA AGA CCA GGC CTA AAG CCT GAT CTT ACG         1635
Gly Glu Gln Val Gly Met Ser Arg Pro Gly Leu Lys Pro Asp Leu Thr
525             530             535             540

GGA ACA TCA AAA TCC TAT GTA AGG TCG CTC TGATCCTCTA CAACTCTTGA           1685
Gly Thr Ser Lys Ser Tyr Val Arg Ser Leu
                545             550

Wild-Type Isolate San Diego Fusion Nucleotide and Amino Acid Sequence

```
CATCCAGTGT CCATC ATG GGT CTC AAG GTG AAC GTC TTT GCC ATA TTC ATG        51
            Met Gly Leu Lys Val Asn Val Phe Ala Ile Phe Met
              1               5                       10

GCA GTA CTG TTA ACT CTC CAA ACA CCC ACC GGT CAA ATC CAT TGG GGC        99
Ala Val Leu Leu Thr Leu Gln Thr Pro Thr Gly Gln Ile His Trp Gly
         15              20                  25

AAT CTC TCT AAG ATA GGG GTG GTA GGG ATA GGA AGT GCA AGC TAC AAA       147
Asn Leu Ser Lys Ile Gly Val Val Gly Ile Gly Ser Ala Ser Tyr Lys
         30              35                  40

GTT ATG ACT CGT TCC AGC CAT CAA TCA TTG GTC ATA AAA TTA ATG CCC       195
Val Met Thr Arg Ser Ser His Gln Ser Leu Val Ile Lys Leu Met Pro
 45              50                  55                      60

AAT ATA ACT CTC CTC AAT AAC TGC ACG AGG GTA GAG ATT GCA GAA TAC       243
Asn Ile Thr Leu Leu Asn Asn Cys Thr Arg Val Glu Ile Ala Glu Tyr
                 65                  70                  75

AGG AGA CTA CTG AGA ACA GTT TTG GAA CCA ATT AGA GAT GCA CTT AAT       291
Arg Arg Leu Leu Arg Thr Val Leu Glu Pro Ile Arg Asp Ala Leu Asn
             80                  85                  90

GCA ATG ACC CAG AAT ATA AGA CCG GTT CAG AGT GTA GCT TCA AGT AGG       339
Ala Met Thr Gln Asn Ile Arg Pro Val Gln Ser Val Ala Ser Ser Arg
         95                  100                 105

AGA CAC AAG AGA TTT GCG GGA GTA GTC CTG GCA GGT GCG GCC CTA GGC       387
Arg His Lys Arg Phe Ala Gly Val Val Leu Ala Gly Ala Ala Leu Gly
 110                 115                     120

GTT GCC ACA GCT GCT CAG ATA ACA GCC GGC ATT GCA CTT CAC CAG TCC       435
Val Ala Thr Ala Ala Gln Ile Thr Ala Gly Ile Ala Leu His Gln Ser
125                 130                     135                 140

ATG CTG AAC TCT CAA GCC ATC GAC AAT CTG AGA GCA AGC CTG GAA ACT       483
Met Leu Asn Ser Gln Ala Ile Asp Asn Leu Arg Ala Ser Leu Glu Thr
                 145                 150                     155

ACT AAT CAG GCA ATT GAG GCA ATC AGA CAA GCA GGG CAG GAG ATG ATA       531
Thr Asn Gln Ala Ile Glu Ala Ile Arg Gln Ala Gly Gln Glu Met Ile
             160                 165                     170

TTG GCT GTT CAG GGT GTC CAA GAC TAC ATC AAT AAT GAG CTG ATA CCG       579
Leu Ala Val Gln Gly Val Gln Asp Tyr Ile Asn Asn Glu Leu Ile Pro
         175                 180                     185

TCT ATG AAC CAA CTA TCT TGT GAT TTA ATC GGC CAG AAG CTA GGG CTC       627
Ser Met Asn Gln Leu Ser Cys Asp Leu Ile Gly Gln Lys Leu Gly Leu
     190                 195                 200

AAA TTG CTC AGA TAC TAT ACA GAA ATC CTG TCA TTA TTT GGC CCC AGC       675
Lys Leu Leu Arg Tyr Tyr Thr Glu Ile Leu Ser Leu Phe Gly Pro Ser
205                 210                 215                     220

TTA CGG GAC CCC ATA TCT GCG GAG ATA TCC ATC CAG GCT TTG AGC TAT       723
Leu Arg Asp Pro Ile Ser Ala Glu Ile Ser Ile Gln Ala Leu Ser Tyr
                 225                 230                     235

GCG CTT GGG GGA GAT ATC AAT AAG GTA TTA GAA AAG CTC GGA TAC AGT       771
Ala Leu Gly Gly Asp Ile Asn Lys Val Leu Glu Lys Leu Gly Tyr Ser
             240                 245                     250
```

FIGURE 11

```
GGA GGT GAT TTA CTG GGC ATC TTA GAG AGC AGA GGA ATA AAG GCC CGG         819
Gly Gly Asp Leu Leu Gly Ile Leu Glu Ser Arg Gly Ile Lys Ala Arg
        255                 260                 265

ATA ACT CAC GTC GAC ACA GAG TCC TAC TTC ATT GTC CTC AGT ATA GCC         867
Ile Thr His Val Asp Thr Glu Ser Tyr Phe Ile Val Leu Ser Ile Ala
        270                 275                 280

TAT CCG ACG CTG TCC GAG ATT AAG GGG GTG ATT GTC CAC CGG CTA GAG         915
Tyr Pro Thr Leu Ser Glu Ile Lys Gly Val Ile Val His Arg Leu Glu
285                 290                 295                 300

GGG GTC TCG TAC AAT ATA GGC TCT CAA GAG TGG TAT ACC ACT GTG CCC         963
Gly Val Ser Tyr Asn Ile Gly Ser Gln Glu Trp Tyr Thr Thr Val Pro
                305                 310                 315

AAG TAT GTT GCA ACC CAA GGG TAC CTT ATC TCG AAT TTT GAT GAG TCA        1011
Lys Tyr Val Ala Thr Gln Gly Tyr Leu Ile Ser Asn Phe Asp Glu Ser
        320                 325                 330

TCG TGT ACT TTC ATG CCA GAG GGG ACT GTG TGC AGC CAA AAT GCC TTG        1059
Ser Cys Thr Phe Met Pro Glu Gly Thr Val Cys Ser Gln Asn Ala Leu
        335                 340                 345

TAC CCG ATG AGT CCT CTG CTC CAA GAA TGC CTC CGG GGG TCC ACC AAG        1107
Tyr Pro Met Ser Pro Leu Leu Gln Glu Cys Leu Arg Gly Ser Thr Lys
350                 355                 360

TCC TGT GCT CGT ACA CTC GTA TCC GGG TCT TTT GGG AAC CGG TTC ATT        1155
Ser Cys Ala Arg Thr Leu Val Ser Gly Ser Phe Gly Asn Arg Phe Ile
365                 370                 375                 380

TTA TCA CAA GGG AAC CTA ATA GCC AAT TGT GCA TCA ATC CTC TGC AAG        1203
Leu Ser Gln Gly Asn Leu Ile Ala Asn Cys Ala Ser Ile Leu Cys Lys
                385                 390                 395

TGT TAC ACA ACA GGA ACG ATC ATT AAT CAA GAC CCT GAC AAG ATC CTA        1251
Cys Tyr Thr Thr Gly Thr Ile Ile Asn Gln Asp Pro Asp Lys Ile Leu
        400                 405                 410

ACA TAC ATT GCT GCC GAT CAC TGC CCG GTA GTC GAG GTG AAC GGT GTG        1299
Thr Tyr Ile Ala Ala Asp His Cys Pro Val Val Glu Val Asn Gly Val
        415                 420                 425

ACC ATC CAA GTC GGG AGC AGG AGG TAT CCG GAC GCG GTG TAC CTG CAC        1347
Thr Ile Gln Val Gly Ser Arg Arg Tyr Pro Asp Ala Val Tyr Leu His
        430                 435                 440

AGA ATT GAC CTC GGT CCT CCC ATA TCA TTG GAG AAG TTG GAC GTA GGG        1395
Arg Ile Asp Leu Gly Pro Pro Ile Ser Leu Glu Lys Leu Asp Val Gly
445                 450                 455                 460

ACA AAT CTG GGG AAT GCA ATT GCT AAG CTG GAG GAT GCC AAG GAA TTG        1443
Thr Asn Leu Gly Asn Ala Ile Ala Lys Leu Glu Asp Ala Lys Glu Leu
                465                 470                 475

CTG GAG TCA TCG GAC CAG ATA TTG AGG AGT ATG AAA GGT TTA TCG AGC        1491
Leu Glu Ser Ser Asp Gln Ile Leu Arg Ser Met Lys Gly Leu Ser Ser
                480                 485                 490

ACT AGC ATA GTT TAC ATC CTG ATT GCA GTG TGT CTT GGA GGG TTG ATA        1539
Thr Ser Ile Val Tyr Ile Leu Ile Ala Val Cys Leu Gly Gly Leu Ile
        495                 500                 505

GGG ATC CCC GCT TTA ATA TGT TGC TGC AGG GGG CGC TGT AAC AAA AAG        1587
Gly Ile Pro Ala Leu Ile Cys Cys Cys Arg Gly Arg Cys Asn Lys Lys
510                 515                 520
```

FIGURE 11

```
GGA GAA CAA GTT GGT ATG TCA AGA CCA GGC CTA AAG CCT GAT CTT ACA        1635
Gly Glu Gln Val Gly Met Ser Arg Pro Gly Leu Lys Pro Asp Leu Thr
525             530             535             540

GGG ACA TCA AAA TCC TAT GTA AGG TCG CTC TGATCCCCTA CAACTCTTGA          1685
Gly Thr Ser Lys Ser Tyr Val Arg Ser Leu
                545             550

Wild-Type Isolate Chicago-1 Fusion Nucleotide and Amino Acid Sequence

```
CATCCAGTGT CCATC ATG GGT CTC AAG GTG AAC GTC TTT GCC ATA TTC ATG           51
            Met Gly Leu Lys Val Asn Val Phe Ala Ile Phe Met
             1           5                      10

GCA GTA CTG TTA ACT CTC CAA ACA CCC ACC GGT CAA ATC CAT TGG GGC            99
Ala Val Leu Leu Thr Leu Gln Thr Pro Thr Gly Gln Ile His Trp Gly
         15              20                  25

AAT CTC TCT AAG ATA GGG GTG GTA GGG ATA GGA AGT GCA AGC TAC AAA           147
Asn Leu Ser Lys Ile Gly Val Val Gly Ile Gly Ser Ala Ser Tyr Lys
         30              35              40

GTT ATG ACT CGT TCC AGC CAT CAA TCA TTG GTC ATA AAA TTA ATG CCC           195
Val Met Thr Arg Ser Ser His Gln Ser Leu Val Ile Lys Leu Met Pro
 45              50              55              60

AAT ATA ACT CTC CTC AAT AAC TGC ACG AGG GTA GAG ATT GCA GAA TAC           243
Asn Ile Thr Leu Leu Asn Asn Cys Thr Arg Val Glu Ile Ala Glu Tyr
             65              70              75

AGG AGA CTA CTG AGA ACA GTT TTG GAA CCA ATT AGA GAT GCA CTT AAT           291
Arg Arg Leu Leu Arg Thr Val Leu Glu Pro Ile Arg Asp Ala Leu Asn
             80              85              90

GCA ATG ACC CAG AAT ATA AGA CCG GTT CAG AGT GTA GCT TCA AGT AGG           339
Ala Met Thr Gln Asn Ile Arg Pro Val Gln Ser Val Ala Ser Ser Arg
         95              100             105

AGA CAC AAG AGA TTT GCG GGA GTA GTC CTG GCA GGT GCG GCC CTA GGC           387
Arg His Lys Arg Phe Ala Gly Val Val Leu Ala Gly Ala Ala Leu Gly
 110             115                 120

GTT GCC ACA GCT GCT CAG ATA ACA GCC GGC ATT GCA CTT CAC CAG TCC           435
Val Ala Thr Ala Ala Gln Ile Thr Ala Gly Ile Ala Leu His Gln Ser
125             130                 135                 140

ATG CTG AAC TCT CAA GCC ATC GAC AAT CTG AGA GCA AGC CTG GAA ACT           483
Met Leu Asn Ser Gln Ala Ile Asp Asn Leu Arg Ala Ser Leu Glu Thr
             145                 150                 155

ACT AAT CAG GCA ATT GAG GCA ATC AGA CAA GCA GGG CAG GAG ATG ATA           531
Thr Asn Gln Ala Ile Glu Ala Ile Arg Gln Ala Gly Gln Glu Met Ile
             160                 165                 170

TTG GCT GTT CAG GGT GTC CAA GAC TAC ATC AAT AAT GAG CTG ATA CCG           579
Leu Ala Val Gln Gly Val Gln Asp Tyr Ile Asn Asn Glu Leu Ile Pro
         175                 180                 185

TCT ATG AAC CAA CTA TCT TGT GAT TTA ATC GGC CAG AAG CTA GGG CTC           627
Ser Met Asn Gln Leu Ser Cys Asp Leu Ile Gly Gln Lys Leu Gly Leu
 190                 195                 200

AAA TTG CTC AGA TAC TAT ACA GAA ATC CTG TCA TTA TTT GGC CCC AGC           675
Lys Leu Leu Arg Tyr Tyr Thr Glu Ile Leu Ser Leu Phe Gly Pro Ser
205                 210                 215                 220

TTA CGG GAC CCC ATA TCT GCG GAG ATA TCC ATC CAG GCT TTG AGC TAT           723
Leu Arg Asp Pro Ile Ser Ala Glu Ile Ser Ile Gln Ala Leu Ser Tyr
                 225                 230                 235

GCG CTT GGG GGA GAT ATC AAT AAG GTA TTA GAA AAG CTC GGA TAC AGT           771
Ala Leu Gly Gly Asp Ile Asn Lys Val Leu Glu Lys Leu Gly Tyr Ser
                 240                 245                 250
```

FIGURE 12

| | |
|---|---|
| GGA GGT GAT TTA CTG GGC ATC TTA GAG AGC AGA GGA ATA AAG GCC CGG<br>Gly Gly Asp Leu Leu Gly Ile Leu Glu Ser Arg Gly Ile Lys Ala Arg<br>        255                   260                  265 | 819 |
| ATA ACT CAC GTC GAC ACA GAG TCC TAC TTC ATT GTC CTC AGT ATA GCC<br>Ile Thr His Val Asp Thr Glu Ser Tyr Phe Ile Val Leu Ser Ile Ala<br>270                   275                   280 | 867 |
| TAT CCG ACG CTG TCC GAG ATT AAG GGG GTG ATT GTC CAC CGG CTA GAG<br>Tyr Pro Thr Leu Ser Glu Ile Lys Gly Val Ile Val His Arg Leu Glu<br>285                   290                   295                 300 | 915 |
| GGG GTC TCG TAC AAT ATA GGC TCT CAA GAG TGG TAT ACC ACT GTG CCC<br>Gly Val Ser Tyr Asn Ile Gly Ser Gln Glu Trp Tyr Thr Thr Val Pro<br>               305                   310                   315 | 963 |
| AAG TAT GTT GCA ACC CAA GGG TAC CTT ATC TCG AAT TTT GAT GAG TCA<br>Lys Tyr Val Ala Thr Gln Gly Tyr Leu Ile Ser Asn Phe Asp Glu Ser<br>           320                   325                   330 | 1011 |
| TCG TGT ACT TTC ATG CCA GAG GGG ACT GTG TGC AGC CAA AAT GCC TTG<br>Ser Cys Thr Phe Met Pro Glu Gly Thr Val Cys Ser Gln Asn Ala Leu<br>               335                   340                   345 | 1059 |
| TAC CCG ATG AGT CCT CTC CTC CAA GAA TGC CTC CGG GGG TCC ACC AAG<br>Tyr Pro Met Ser Pro Leu Leu Gln Glu Cys Leu Arg Gly Ser Thr Lys<br>350                   355                   360 | 1107 |
| TCC TGT GCT CGT ACA CTC GTA TCC GGG TCT TTT GGG AAC CGG TTC ATT<br>Ser Cys Ala Arg Thr Leu Val Ser Gly Ser Phe Gly Asn Arg Phe Ile<br>365                   370                   375                   380 | 1155 |
| TTA TCA CAA GGG AAC CTA ATA GCC AAT TGT GCA TCA ATC CTC TGC AAG<br>Leu Ser Gln Gly Asn Leu Ile Ala Asn Cys Ala Ser Ile Leu Cys Lys<br>               385                   390                   395 | 1203 |
| TGT TAC ACA ACA GGA ACG ATC ATT AAT CAA GAC CCT GAC AAG ATC CTA<br>Cys Tyr Thr Thr Gly Thr Ile Ile Asn Gln Asp Pro Asp Lys Ile Leu<br>           400                   405                   410 | 1251 |
| ACA TAC ATT GCT GCC GAT CAC TGC CCG GTA GTC GAG GTG AAC GGT GTG<br>Thr Tyr Ile Ala Ala Asp His Cys Pro Val Val Glu Val Asn Gly Val<br>             415                   420                   425 | 1299 |
| ACC ATC CAA GTC GGG AGC AGG AGG TAT CCG GAC GCG GTG TAC CTG CAC<br>Thr Ile Gln Val Gly Ser Arg Arg Tyr Pro Asp Ala Val Tyr Leu His<br>430                   435                   440 | 1347 |
| AGA ATT GAC CTC GGT CCT CCC ATA TCA TTG GAG AAG TTG GAC GTA GGG<br>Arg Ile Asp Leu Gly Pro Pro Ile Ser Leu Glu Lys Leu Asp Val Gly<br>445                   450                   455                  460 | 1395 |
| ACA AAT CTG GGG AAT GCA ATT GCT AAG CTG GAG GAT GCC AAG GAA TTG<br>Thr Asn Leu Gly Asn Ala Ile Ala Lys Leu Glu Asp Ala Lys Glu Leu<br>               465                   470                   475 | 1443 |
| CTG GAG TCA TCG GAC CAG ATA TTG AGG AGT ATG AAA GGT TTA TCG AGC<br>Leu Glu Ser Ser Asp Gln Ile Leu Arg Ser Met Lys Gly Leu Ser Ser<br>             480                   485                   490 | 1491 |
| ACT AGC ATA GTT TAC ATC CTG ATT GCA GTG TGT CTT GGA GGG TTG ATA<br>Thr Ser Ile Val Tyr Ile Leu Ile Ala Val Cys Leu Gly Gly Leu Ile<br>           495                   500                   505 | 1539 |
| GGG ATC CCC GCT TTA ATA TGT TGC TGC AGG GGG CGT TGT AAC AAA AAG<br>Gly Ile Pro Ala Leu Ile Cys Cys Cys Arg Gly Arg Cys Asn Lys Lys<br>510                   515                   520 | 1587 |

FIGURE 12

```
GGA GAA CAA GTT GGT ATG TCA AGA CCA GGC CTA AAG CCT GAT CTT ACA         1635
Gly Glu Gln Val Gly Met Ser Arg Pro Gly Leu Lys Pro Asp Leu Thr
525             530             535             540

GGG ACA TCA AAA TCC TAT GTA AGG TCG CTC TGATCCCCTA CAACTCTTGA           1685
Gly Thr Ser Lys Ser Tyr Val Arg Ser Leu
            545             550

AA                                                                      1687
```

| BASE NO. | MORATEN | CHICAGO-1 | SAN DIEGO | PREDICTED AMINO ACID CHANGES IN THE WILD TYPES |
|---|---|---|---|---|
| 575 | A | G | G | Met→Val (RESIDUE NO. 1) |
| 606 | C | T | T | Ser→Phe (RESIDUE NO. 8) |
| 694 | A | G | G | |
| 745 | A | G | G | |
| 1039 | G | A | A | |
| 1070* | A | G | G | Thr→Ala (RESIDUE NO. 163) |
| 1189 | C | A | A | |
| 1243* | T | C | C | |
| 1273 | T | C | C | |
| 1300 | A | G | G | |
| 1306 | C | T | T | |
| 1318 | G | A | A | |
| 1370* | G | A | A | Gly→Arg (RESIDUE NO. 263) |
| 1498 | C | T | T | |
| 1668* | A | C | C | Tyr→Ser (RESIDUE NO. 362) |
| 1765 | T | C | C | |
| 1864 | C | T | T | |
| 1897 | A | G | G | |
| 2003 | T | G | G | |
| 2010 | T | C | C | |
| 1950 | G | A | A | Arg→Lys (RESIDUE NO. 456) |
| 1991 | T | C | C | |
| 2012 | T | C | C | |
| 2071 | C | T | T | |
| 2143 | T | T | C | |
| 2203 | G | A | A | |
| 2206 | A | G | G | |

*THE WILD-TYPE ISOLATES ARE IDENTICAL TO THE EDMONSTON STRAIN AT THESE NUCLEOTIDE POSITIONS.

FIG. 13

NUCLEIC ACIDS ENCODING WILD-TYPE MEASLES VIRUS CONSENSUS HEMAGGLUTININ AND FUSION POLYPEPTIDES AND METHODS OF DETECTION

This application is a continuation of application Ser. No. 07/866,033, filed Apr. 8, 1992, now abandoned.

BACKGROUND OF THE INVENTION

Measles virus was first isolated in cell culture in 1954 from David Edmonston. The Edmonston strain of measles virus became the progenitor for many live-attenuated measles vaccine strains which include Moraten, see Hilleman et al., JAMA 206: 587–90 (1968), currently the only licensed measles vaccine strain in the United States. Aggressive vaccination programs instituted in the mid-1960's resulted in a precipitous drop in reported measles cases from near 700,000 in 1965 to only 1500 in 1983.

Since 1989 dramatic increases in both the numbers and severity of measles cases were reported. In 1989, greater than 17,000 cases of measles and 43 associated deaths were reported in the United States. Nearly 100 fatalities from measles-associated illnesses and greater than 27,000 cases of measles were reported in 1990. Approximately half of the measles cases were in unvaccinated preschool populations, whereas the remaining 50% were in previously vaccinated populations. Outbreaks have continued to occur into 1991, at approximately the rate observed in 1989.

The resurgence of measles is not understood causally, but may be attributed to a failure to vaccinate key inner city populations and to a low but significant rate of primary vaccine failure to raise immunity (estimated at 3–5%). Secondary vaccine failure, which occurs when a person's post-vaccination titre of antibodies drops to a non-protective level after an period of time passes, also is a suspected cause.

The measles resurgence is reflected in a rising epidemic of measles infections among young, previously-immunized adults, in particular persons who are immunocompromised. To account for this development in measles epidemiology, it is postulated that transmission of virus is occurring from vaccinated individuals who harbor subclinical measles infections, or, alternatively, that infection arises from the live-attenuated vaccine itself.

The effort to curb the measles resurgence has focused on the role played by measles virus structural proteins in inducing immunity in a vaccinated mammal. The measles virus, like many members of the paramyxovirus family, contains six major structural proteins: the matrix protein, hemagglutinin, the fusion protein, large protein, phosphoprotein and nucleocapsid protein. Of these, the envelope glycoproteins, hemagglutinin and fusion, have been shown to be responsible for induction of measles virus-neutralizing antibodies. See Varsanyi et al., J. Gen. Virol. 65: 365 (1984), Giraudon et al., Virology 144: 46 (1985), and Drillien et al., Proc. Nat'l. Acad. Sci. USA 85: 1252–56 (1988).

The matrix gene has been the focus of much of the previous genetic research, due to evidence that this gene may play a role in the establishment of persistent infections. Recently, nucleotide sequences encoding matrix protein from the two wild-type measles virus isolates (JM and CM) were compared and found to be distinct from vaccine strain sequence. See Baczko et al., J. Gen. Virol. 72 (Pt 9): 2279–82 (1991). In comparing measles fusion protein with fusion proteins of other paramyxoviruses, the Halle strain of measles was found to contain no amino acid differences from that of the Edmonston vaccine strain fusion protein. See Buckland et al., J. Gen. Virol. 68 (6): 1695–1704 (1987).

Research efforts thus far have mostly been directed towards understanding measles genetics using the more readily available vaccine strains, as opposed to wild-type measles viruses, which are difficult to isolate from an infection. Additionally, because measles virus infections have only recently begun to resurge, no one has thus far attempted to study variations in measles glycoproteins of circulating wild-type virus populations, as compared to a vaccine strain.

Thus, to date, there has been no detection of variations from vaccine strain measles virus glycoproteins which are conserved amongst wild-type strains. Further, no effective vaccine has been proposed to offer protective resistance against recently-emerging wild-type strains.

There is also a notable absence of diagnostic technologies which specifically recognize wild-type viral strains from a vaccine strain. As a consequence, the causal agent of an infection is not readily distinguishable between wild-type or vaccine strains, which in turn makes etiological and epidemiological studies difficult. It is important to distinguish whether a vaccine or exposure to wild-type measles caused an infection, for example, where measles infection arises in an immunocompromised individual previously immunized with measles vaccine.

SUMMARY OF THE INVENTION

It is therefore an object of the present invention to identify amino acid sequences of wild-type measles virus hemagglutinin and fusion glycoproteins, and to provide such polypeptides for immunogenic use.

It is a further object of the invention to provide cDNA sequences reflective of the viral RNA which encode the wild-type measles virus hemagglutinin and fusion glycoproteins.

It is yet another object of the invention to provide a measles virus consensus hemagglutinin polypeptide in substantially pure form that possesses an amino acid sequence described by a consensus hemagglutinin formula herein.

It is a further another object of the invention to provide a measles virus consensus fusion polypeptide in substantially pure form which contains six amino acid substitutions, relative to the Moraten strain fusion protein, which are shared among at least two wild-types of measles virus.

It is a further object of the invention to provide consensus hemagglutinin polypeptide or consensus fusion polypeptide, or both, which can provide enhanced immunogenic properties when utilized in the context of a vaccine against recently-emerging measles strains. It is a further object of the invention to provide such consensus polypeptide(s) and a pharmaceutically acceptable carrier therefor.

It is a further object of the invention to provide a consensus hemagglutinin polypeptide or consensus fusion polypeptide or both, and an adjuvant for use as a vaccine.

It is yet another object of the invention to provide a recombinant vector comprising at least one sequence encoding a consensus hemagglutinin polypeptide or a consensus fusion polypeptide.

It is a further object of the invention to provide a recombinant vector comprising sequences encoding, respectively, a consensus hemagglutinin polypeptide or a consensus fusion polypeptide.

It is yet a further aspect of the invention to provide a live attenuated measles wild-type virus for stimulating an immune response against a measles infection in a mammal.

It is a further aspect of the invention to provide monoclonal antibodies specific to a particular wild-type strain of measles virus.

It is a further object of the invention to provide a method for detecting the etiologic origin of a measles infection, comprising the steps of (a) contacting a sample suspected of containing measles virus with monoclonal antibody that binds a measles wild-type strain epitope but not to a Moraten vaccine strain epitope, wherein said measles wild-type strain epitope is a measles hemagglutinin epitope or a measles fusion protein epitope, and (b) detecting the presence or absence of binding between said monoclonal antibody and said sample.

It is a further object of the invention to provide a method for detecting the etiological origin of a measles infection, comprising the steps of:

(a) preparing for PCR a biological sample suspected of containing a measles virus, (b) contacting said sample with PCR oligonucleotide primers that hybridize to RNA of said measles virus at two sites that flank a restriction endonuclease site, the site being present in a wild-type genome, but not present in a vaccine strain genome, or vice versa (c) performing the polymerase chain reaction to obtain products (d) digesting products of PCR reaction, and (e) determining the presence or absence of digested products, thereby identifying the presence or absence of wild-type measles virus in said sample.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those in the art from this detailed description.

BRIEF DESCRIPTION OF THE DRAWINGS

FIG. 1 (B) is a diagrammatic representation of the 10 conserved changes in the HA of wild-type isolates JM (1977); McI (1983); and the 1988–89 isolates, Ch1 (Chicago-1), Ch2 (Chicago-2), and SD (San Diego). The lollypop symbols indicate the location of potential N-linked glycosylation sites. Five sites previously described in the literature are denoted with open circles. A further glycosylation site is designated with a closed circle.

FIG. 2 compares total nucleotide differences and total predicted amino acid differences between the wild-type isolates and between the aforementioned wild-types and the Moraten vaccine strain.

FIG. 3 shows Moraten strain HA nucleotide and amino acid sequences (SEQ ID NOS:1 and 2).

FIG. 4 shows nucleotide and amino acid sequences (SEQ ID NOS:1 and 2) representing conserved changes between wild-type measles viruses designated Chicago-1, Chicago-2 and San Diego.

FIG. 5 shows wild-type isolate, San Diego, HA nucleotide and amino acid sequences (SEQ ID NOS:5 and 6).

FIG. 6 shows wild-type isolate, Chicago-1, HA nucleotide and amino acid sequences (SEQ ID NOS:7 and 8).

FIG. 7 shows wild-type isolate, Chicago-2, HA nucleotide and amino acid sequences (SEQ ID NOS:9 and 10).

FIG. 8 shows wild-type isolate, McI, HA nucleotide and amino acid sequences (SEQ ID NOS:11 and 12).

FIG. 9 shows wild-type isolate, JM, HA nucleotide and amino acid sequences (SEQ ID NOS:13 and 14).

FIG. 10 shows Moraten strain fusion nucleotide and amino acid sequences (SEQ ID NOS:15 and 16).

FIG. 11 shows wild-type isolate, San Diego, fusion, nucleotide and amino acid sequences (SEQ ID NOS:17 and 18).

FIG. 12 shows wild-type isolate, Chicago-1, fusion nucleotide and amino acid sequences (SEQ ID NOS:19 and 20).

FIG. 13 shows changes in the fusion gene of two wild-type measles isolates relative to the Moraten vaccine strain.

DETAILED DESCRIPTION OF THE PREFERRED EMBODIMENTS

Figure 1B:
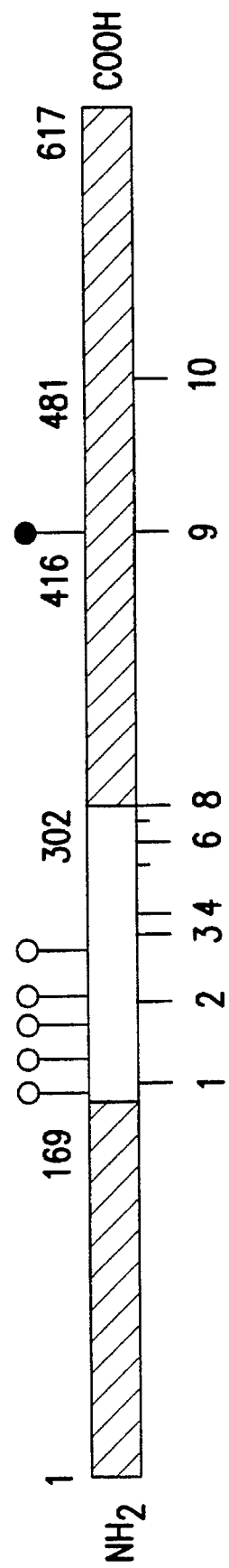
FIG. 1 (A) shows amino acid substitutions in the hemagglutinin (HA) proteins of the wild-type isolates relative to the Moraten vaccine strain (Mor). Asterisks represent amino acid identity with Moraten. The boxed residues represent the conserved changes in the more recent isolates (1983–1989).

The present invention significantly advances the effort to immunize against wild-strain measles infections by providing substantially purified, immunologically active measles polypeptides from wild-type measle virus. Consensus polypeptides within the present invention are suitable for use both to protect against and to identify recently-emerging strains of measles viruses.

Based on an elucidation of wild-type measles virus hemagglutinin and fusion glycoproteins, pursuant to the present invention, shared variations have been discovered among amino acid sequences of the hemagglutinin (HA) and fusion (F) glycoproteins of several wild-type measles virus strains, relative to the current vaccine strain, Moraten. Knowledge of shared variations makes possible the production of consensus polypeptides, in accordance with the present invention, which comprise the conserved regions and which are especially useful in diagnostics and vaccines. As used herein, the acronym PCR is synonymous with polymerase chain reaction and is used interchangeably therewith.

A "consensus polypeptide" according to the present invention includes any of a group having an amino acid sequence selected from:

(1) A polypeptide within a "consensus hemagglutinin formula" that comprises, relative to the hemagglutinin amino acid sequence of Moraten strain, 10 amino acid substitutions and 26 variable amino acid residues. The ten non-variable substitutions with respect to the Moraten strain hemagglutinin sequence are shared among more than one wild-type measles virus, and are found at residue positions specifically identified as follows: 174=Ala, 211=Ser, 243=Gly, 252=His, 276=Phe, 284=Phe, 296=Phe, 302=Arg, 416=Asn, and 481=Asn. See FIG. 1(A), within boxes. The consensus formula further specifies that twenty-six variable residues are found at positions specifically identified as follows:

| Position No. | | |
|---|---|---|
| 4 | denotes | Gln or His |
| 19 | denotes | Lys or Arg |
| 176 | denotes | Thr, Val, or Ala |
| 235 | denotes | Glu or Gly |
| 295 | denotes | Lys or Arg |
| 303 | denotes | Glu or Gly |
| 305 | denotes | Ser or Phe |
| 306 | denotes | Ile or Val |
| 308 | denotes | Ile or Val |
| 320 | denotes | Gln or Arg |
| 339 | denotes | Leu or Phe |
| 348 | denotes | Arg or Lys |
| 367 | denotes | Val or Ile |
| 389 | denotes | Lys or Arg |
| 390 | denotes | Ile or Asn |
| 446 | denotes | Ser or Thr |
| 451 | denotes | Val or Glu |
| 485 | denotes | Val or Ile |
| 501 | denotes | Pro or Ser |
| 544 | denotes | Ser or Asn |
| 546 | denotes | Ser or Gly |
| 559 | denotes | Ile or Val |
| 560 | denotes | Lys or Arg |
| 562 | denotes | Val, Ile or Phe |
| 593 | denotes | His or Tyr |
| 616 | denotes | Arg or Ser. |

A "consensus HA polypeptide" is one having an amino acid sequence (SEQ ID NO: 21) that conforms to the definition of the consensus formula. Accordingly, the category of consensus HA polypeptides includes, inter alia, wild-type hemagglutinin proteins depicted in FIGS. 5–9 and SEQ ID NOS:5–14, respectively.

(2) A fusion polypeptide, the amino acid sequence (SEQ ID NO: 22) of which contains six amino acid substitutions, relative to the Moraten strain fusion protein, which are shared among at least two wild-types and are localized at residue positions identified in FIG. 13. Such a polypeptide is denoted a "consensus fusion polypeptide," a category that includes, inter alia, the wild-type fusion proteins depicted in FIGS. 11 and 12 and SEQ ID NOS:17–20.

The term "polypeptide" in the present context has a conventional meaning, i.e., denoting a sequence of amino acids. An amino acid sequence can be modified in accordance with the present invention, for example, by chemical, enzymatic or other treatment which does not diminish the immunogenic activity of the polypeptide to any substantial extent.

The term "wild-type" denotes a measles strain other than the Moraten or Edmonston strains, including wild-type isolates JM (1977), McI (1983) and the 1988–89 isolates, Ch1 (Chicago-1), Ch2 (Chicago-2), and SD (San Diego). The aforementioned wild-type strains are identified by reference to their HA-encoding nucleotide sequences shown FIGS. 5 through 9 and SEQ ID NOS:5–14, respectively.

A polypeptide of the present invention may be in "substantially pure" form, which means that the polypeptide is substantially free from other proteins which would interfere with an immune response to the hemagglutinin or fusion consensus polypeptides when administered to a mammal.

In the context of the present description, an "immunogenically active polypeptide" is any of the above-described consensus polypeptides or a fragment thereof (see below) which elicits a protective immune response, for example, the production of neutralizing antibodies against at least one wild-type strain of measles, in a mammal to which it is administered. The resulting response imparts a humoral, secretory or cell-mediated immunity to a wild-type measles infection, which permits the individual either to overcome infection more easily than a non-immunized individual or to tolerate the infection without significant clinical effect. Thus, immunization according to the present invention is a process of increasing resistance to infection with wild-type measles virus.

A "fragment" of a polypeptide according to the invention is a subsequence of a consensus polypeptide, which subsequence is of sufficient size and conformation to remain immunogenically active, i.e., to comprise at least one epitope of a consensus polypeptide. Examples of fragments include the extracellular domain of either the fusion or hemagglutinin protein.

Consensus polypeptides according to the present invention can be administered in the form of live measles virus, or as attenuated live measles virus to actively immunize a mammal. Attenuation of a live measles virus is achieved by successively passing live virus in mammalian, avian or other foreign host cell culture, such as chick embryo fibroblasts, at an incubation temperature sufficient to diminish the reproductive capacity of the microbe, see Hilleman et al., JAMA 206: 587–90 (1968). Live-attenuated virus may be administered for example, by intramuscular injection into a mammal.

A preferred embodiment of the present invention comprises immunization by delivery of a consensus polypeptide in a more purified form by means of a recombinant vector that contains measles virus gene sequence(s) coding for at least one of the consensus polypeptides enumerated above. A suitable vector includes a recombinant virus, such as vaccinia virus, that can infect an animal host cell to bring about expression of the measles virus proteins on the cell surface of the infected cell, as in a natural measles virus infection. See Drillien et al., Proc. Nat'l Acad. Sci. USA 85: 1252–56 (1988), the contents of which are incorporated herein by reference. Other examples of recombinant viruses used to express measles virus include canary pox, see Taylor et al., Virology 187: 321–28 (1992), and baculovirus.

It is preferable to deliver both consensus fusion and consensus hemagglutinin polypeptides together to a mammal to induce an immune response in the mammal. This is accomplished by delivering separate recombinant vectors containing the consensus fusion or consensus hemagglutinin polypeptides together to a mammal. Most preferably, both the consensus hemagglutinin and consensus fusion genes are inserted into the same recombinant vector and co-expressed by the host cell for more effective immunoprotection.

Consensus polypeptides of the present invention may be coupled to a macromolecular carrier to increase the immunogenicity of a vaccine preparation. A vaccine composition comprising at least one consensus polypeptide, or a combination of two or more consensus polypeptides is provided in an immunologically effective amount, together with an immunologically acceptable carrier or vehicle according to the present invention.

A suitable carrier for a vaccine according to the invention is a polymer to which a polypeptide(s) is bound by hydrophobic non-covalent interaction. Examples include polystyrene, a polysaccharide, and a polypeptide like bovine serum albumin or ovalbumin. The carrier preferably should be non-toxic and non-allergenic.

A vaccine according to the present invention further comprises an adjuvant in order to increase the immunogenicity of the vaccine preparation. The adjuvant can be selected, for example, from Freund's complete or incomplete adjuvant, aluminum hydroxide, a saponin, a muramyl dipeptide, an iscom, a vegetable oil (like peanut oil) or a mineral oil, such as silicone oil.

A vaccine is prepared by mixing an immunogenically effective amount of consensus polypeptide or combination of consensus polypeptides with a carrier or vehicle resulting in the desired concentration of the immunogenically effective consensus polypeptide. The amount of consensus polypeptide in the vaccine will depend on the mammal to be immunized, e.g. the age and weight of the mammal, as well as the immunogenicity of the consensus polypeptide. For most purposes, the amount of polypeptide ranges between 1–500 µg. The vaccine is prepared, according to the invention, to ensure that the identity and immunological effectiveness of the consensus polypeptide are maintained, and that no unwanted microbial contaminants are introduced. The vaccine can be lyophilized, and is preferably packaged in a sealed, sterile container.

Polypeptides of the present invention can be produced by recombinant DNA techniques, such as those set forth generally by Maniatis et al., MOLECULAR CLONING—A LABORATORY MANUAL, Cold Spring Harbor Laboratory (1982). In addition, methods specifically suitable to cloning, sequencing and expressing genes which code for measles virus proteins also have been described. Thus, Alkhatib et al., Virology 150: 479–490 (1986) and Richardson et al., Virology 155: 508–523 (1986), report on the cloning and complete nucleotide sequencing of the hemagglutinin and fusion proteins, respectively, of the Edmonston strain of measles virus.

The hemagglutinin and fusion protein genes can be cloned into suitable expression vectors and expressed in prokaryotic or eukaryotic expression systems. For instance, Vialard et al., J. Virol. 64: 37–50 (1990), expressed measles fusion and hemagglutinin proteins in S. furgiperda by means of a baculovirus-derived vector. In addition, Drillien et al., Proc. Nat'l Acad. Sci. USA 85: 1252–56 (1988), cloned measles fusion and hemagglutinin genes into vaccinia virus-derived vectors and expressed the proteins in BHK-21 cells. The recombinantly-produced proteins were used successfully to vaccinate mice against measles infection, showing that the vaccinia/BHK-21 cell expressed proteins that retained their antigenic properties.

Maniatis et al., supra, also disclose techniques for site-specific mutagenesis which are suitable for introducing specific mutations into a cloned measles gene, including the fusion and hemagglutinin genes mentioned above. One widely used technique in this regard is described by Kunkel et al., Methods Enzymol. 154: 367 (1987), and can be carried out using a commercially available kit. Thus, Vialard et al., supra, employed the "MUTA-GEN" in vitro mutagenesis kit (product of Bio-Rad) to produce a baculovirus vector for expressing cloned measles virus genes, and Drillien et al., supra, used the site-directed mutagenesis techniques of Zollar et al., Methods Enzymol. 100: 468–500 (1983), to engineer restriction sites into a vaccinia virus vector for expressing measles virus genes.

With conventional techniques, therefore, a sequence encoding a measles virus fusion or hemagglutinin protein, can be cloned from viral genomic RNA or obtained as a cDNA from viral mRNA from an infected cell. The RNA can be converted to double-stranded DNA using cDNA cloning techniques well-known to the art, including PCR-based techniques. Linkers or tails may be placed on the ends of the double stranded DNA to provide convenient restriction sites. After restriction digestion, the DNA may be introduced to any site in a vector, such as a plasmid vector, which has been restricted with a restriction enzyme that generates compatible ends. Following ligation, by means of standard techniques, the DNA can then be introduced to a cell, where it can be expressed to produce the desired protein.

Such a coding sequence for a measles virus hemagglutinin or fusion protein gene can be subjected to site-specific mutagenesis to alter selected base pairs in accordance with the present invention. In this manner DNAs can be obtained that encode consensus polypeptides defined according to the present invention, such as a San Diego wild-type fusion or hemagglutinin protein. Thus, the sequence of a cloned gene, such as the Edmonston strain hemagglutinin and fusion protein genes, can be altered by site-specific mutagenesis to produce a DNA sequence encoding any of the consensus polypeptides, such as the consensus-HA proteins under the consensus formula set forth above (SEQ ID NO: 21), or any of the wild-types set forth in FIGS. 5–9, or 11–12 and SEQ ID NOS:5–14 and 17–20.

Measles hemagglutinin or fusion gene-containing vectors can be obtained from the laboratories of the above-mentioned authors. Alternatively, they can be reconstructed as described in the cited publications. Oligonucleotides containing a mutation to be introduced to the cloned gene can be synthesized by well-known DNA synthetic techniques, preferably by phosphoramidite chemistry and most preferably as implemented on an automated synthesizer, such as the synthesizer commercialized by Applied Biosystems.

With regard to designing oligonucleotides for introducing a mutation, it will be readily appreciated that any codon for a desired amino acid may be used to encode that amino acid in a hemagglutinin or fusion protein amino acid sequence. Codon usage preference can indicate that one or another of several redundant codons is preferred in a given application. As is well known to the art, the oligonucleotide can be designed for optimum hybridization to a target sequence by adjusting its length and GC content, as permitted by the complementary target sequence.

As set forth above, the oligonucleotide may be used in accordance with any of several techniques for oligonucleotide-directed site-specific mutagenesis to introduce a specific mutation to a starting sequence to provide a DNA encoding a consensus hemagglutinin or consensus fusion protein having an amino acid sequence described above. A gene encoding a consensus fusion and/or a hemagglutinin protein(s), respectively, can cloned by linking such a gene to a suitable promoter in a replicable vector. Consensus polypeptides are thus produced by propagating the vector in a suitable host under conditions conducive to protein expression.

In accordance with the present invention, wild-type measles hemagglutinin and fusion protein genes can be isolated de novo from the wild type strains described above. It will be appreciated that site-directed mutatagenesis techniques can be used in the same manner to convert any measles hemagglutinin- or fusion protein-encoding sequence to any such respective consensus sequence within the present invention.

Any of the immunologically active consensus polypeptides of the present invention, or antibodies raised against these polypeptides, are useful as diagnostic reagents for determining the presence of wild-type measles virus. Several assay techniques based upon immunological reactions between antigens and antibodies are useful in the invention, including enzyme-linked immunosorbent assay (ELISA), radioimmuno assays, immunoelectrophoresis and the like.

Also useful diagnostically are immunohistochemical techniques which employ monoclonal antibodies of known, specific reactivities. In accordance with this aspect of the present invention, a sample is obtained from a person to detect the type of measles infection by removing a body fluid or tissue suspected of harboring measles virus, such as alveolar or respiratory epithelial cells obtained from a bronchial wash, nasopharyngeal aspirates, throat swabs, urine or blood.

Immunohistochemical studies are performed on such cells using a monoclonal antibody (see below) specific for a vaccine strain and not cross-reactive with a wild-type, for example, to identify an infection as arising from a vaccine strain, see Harlow et al., Antibodies: A Laboratory Manual Cold Spring Harbor (1988).

Monoclonal antibodies which can distinguish a wild-type measles virus from a vaccine strain are made using the consensus polypeptides of the present invention. For example, monoclonal antibodies are made which distinguish the Chicago-1 wild-type virus from an Edmonston vaccine strain. Such antibodies are made, for example, by fusion of myeloma cells with spleen cells of Balb/c mice immunized with Chicago-1 type virus, using conventional techniques according to Kohler and Milstein. These techniques have been adapted for use in making measles monoclonals. See, for example, Bellini et al., J. Gen. Virol. 43: 633–39 (1979), and McFarlin et al., J. Gen. Viro. 48: 425–29 (1980), the respective contents of which are hereby incorporated by reference.

Monoclonal antibodies thus produced are identified for specific reactivity with consensus hemagglutinin or fusion polypeptides of the invention. This is accomplished by growing the wild-type and vaccine virus in the presence of radioactive methionine until about 70% of the cells exhibit cytopathology or fusion. The cells then are lysed in a detergent mixture (also containing proteolysis inhibitors) which compels the viral proteins to disassociate from one another. Monoclonal antibody is then added which precipitates proteins with which it binds specifically. Finally, precipitated viral proteins are electrophoresed on a polyacrylamide gel along with standard measles vaccine proteins, and identified after autoradiography.

Another method for detecting the etiological origin of a measles infection from a sample uses PCR to amplify a region of measles virus sample possessing specific nucleotide differences between a wild-type and vaccine strain. In this regard, a biological sample suspected of containing a measles virus is prepared for PCR and contacted with PCR oligonucleotide primers. Primers are selected that hybridize to RNA of measles virus at two sites which flank an identifying restriction endonuclease site. Such a site can be present in a viral genome encoding consensus polypeptide, but not present in a vaccine strain genome. Alternatively, a restriction site may be present in a vaccine strain genome, but not in viral genome encoding consensus polypeptide. The polymerase chain reaction then is performed, followed by digestion with restriction nuclease. Thus, in the case where a restriction site is present in a viral genome encoding consensus polypeptide, but not in vaccine strain genome, a sample identified as consensus sequence will be fragmented during digestion, whereas a vaccine strain would not. This difference is detected by performing gel electrophoresis to compare the size of the reaction products.

For example, to detect the HA of San Diego, Chicago-1 or Chicago-2 from the Moraten vaccine strain, PCR primers are constructed which flank nucleotide position 774, where these wild-types possess a T to C substitution relative to the Moraten strain. This substitution creates a Dra III enzyme cleavage site. By amplifying a region of the measles virus encompassing this site and comparing the sizes obtained from a Dra III digest of the PCR products, any of the three wild-types mentioned can be distinguished from the vaccine strain.

The present invention is further described with reference to the following, illustrative examples.

EXAMPLE 1

ORIGIN AND ISOLATION OF WILD-TYPE MEASLES VIRAL RNA

Three contemporary wild-type measles viruses, designated "Chicago-1," "Chicago-2" and "San Diego," were obtained as clinical isolates from unvaccinated patients who met the clinical case definition for measles (Centers for Disease Control, Measles prevention: recommendations of the Immunization Practices Advisory Committee (ACIP) MMWR 38 (no. S-9) 1–18 (1983). Two isolates from Chicago were supplied by Dr. Mary Smaron of the University of Chicago, Department of Pediatrics. Chicago-1 was isolated from a nasopharyngeal aspirate of an 8-month-old female in August of 1989, during the peak of a measles epidemic. Chicago-2 was isolated from the urine of a 7-month-old female in December, 1988, well before a major outbreak in Chicago, and proved to be a fatal case. The third wild-type, submitted by the San Diego County Health Department during an outbreak, was isolated from a nasopharyngeal aspirate of a 19-month-old male in February of 1989. The isolates were passaged 5–8 times in Vero cells to obtain sufficient stocks for RNA preparation.

A fourth wild-type measles virus, designated "McI," was isolated in March, 1983, by Dr. K. McIntosh's group in Boston. Strain McI and a measles wild-type from 1977, designated "JM," were supplied by Dr. P. Albrecht of the Food and Drug Administration in Bethesda, Md.

The virus reference vaccine strain Moraten was obtained in lyophilized form as the product "Attenuvax" (Merck, Sharp & Dohme, West Point, Pa.), see also, Hilleman et al., JAMA 206: 587–90 (1968). The Edmonston strain was obtained from the American Type Culture Collection (ATCC), it had been deposited by J. Enders after 24 passages in human kidney and 28 passages in human amnion. Both virus strains were passaged 2–3 times in Vero cell culture to provide stock for RNA production.

The above strains were cultivated in Vero (E-6) cells in Dulbecco's modified Eagle's medium and supplemented with 10% fetal calf serum, glutamine, and antibiotics for virus growth. Vero cells were infected at a multiplicity of infection (MOI) of 0.1–1.0, and were allowed to reach maximum virus growth before cell destruction occurred. Total RNA from measles virus-infected Vero cells was extracted using guanidinium thiocyanate, see Chirgwin et al., Biochem. 18: 5294–99 (1979), and purified by centrifugation through a cesium chloride cushion as described by Glisin et al., Biochem. 12: 2633–37 (1974). The RNA pellet was washed twice with 70% ethanol and resuspended in diethyl pyrocarbonate-treated water. The RNA concentrations were determined by UV spectroscopy.

EXAMPLE 2

SEQUENCING WILD-TYPE MEASLES VIRAL RNA

Viral messenger RNA (mRNA) was chosen as the template for sequencing to eliminate the need to sequence multiple cDNA clones of viral genes or gene transcripts. Since the template used in the sequencing reactions was RNA, a degree of heterogeneity was observed. Usually the instances of multiple bands occurred at the third position of a codon reflecting a mixed population of mRNA species. In these cases the strongest signal was considered to be the correct base.

Nucleotides were numbered as described in the study by Cattaneo et al., Virology 173: 415–25 (1989), which contained a correction to the previously published Edmonston fusion gene sequence. See Richardson et al., Virology 105: 205–22 (1986). The first in-frame AUG in the Edmonston fusion gene starts at nucleotide 575. Fusion (F) and hemagglutinin (HA) base changes identified between Moraten and the published Edmonston sequences were verified by sequencing those regions of mRNA from the Edmonston strain obtained from the ATCC. The primers for the fusion (F) and hemagglutinin (HA) genes were complementary to the mRNA transcripts of the Edmonston F gene sequence (Richardson et al. (1986), supra) and the Edmonston HA gene sequence (Alkhatib et al., Virology 150: 479–90 (1986)), respectively, and ranged in length from 18 to 25 nucleotides. The primers used to sequence the F gene corresponded to the following nucleotide positions: 793–813, 959–979, 1193–1217, 1408–1428, 1551–1568, 1738–1756, 1823–1843, 2077–2097, and 2272–2292. The HA gene primers corresponded to nucleotide positions 152–172, 268–287, 400–423, 555–575, 753–773, 946–966, 1059–1079, 1145–1166, 1230–1251, 1332–1352, 1537–1556, 1712–1735 and 1893–1911.

Direct sequencing of the mRNA was performed using the Sanger dideoxy chain-terminating method modified for RNA templates, see Air et al., Virology 97: 468–72 (1979). Approximately 50 μg of total cellular RNA was used as the template for the sequencing reactions of the vaccine strain and between 70–80 μg of RNA was required for sequencing the wild-type strains. Terminal transferase was added to the chase mixture to help eliminate stops when necessary.

Sequence data were analyzed using version 7.0 of the sequence analysis software package of the University of Wisconsin Genetics Computer Group, see Devereaux et al., Nucleic Acid Res. 12: 387–395 (1984), and the "Phylip" software package (Phylogeny Inference Package, version 3.4) See Felsenstein et al., Am. Rev. Genet. 22: 512–565 (1988). Both packages were run on a VAX computer (product of Digital Equipment Corporation).

EXAMPLE 3

RADIOLABELLING AND IMMUNOPRECIPITATION OF HEMAGGLUTININ ANTIGEN

Vero cells were inoculated with Moraten, Chicago-1, or San Diego virus at an MOI of 0.1. At 16–24 hr postinfection, cells were preincubated 1–2 hr in methionine-free medium supplemented with 1% bovine serum albumin (BSA) and then radiolabelled for 2 hr in medium containing $^{35}$S-methionine at a concentration of 50 μCi/ml (ICN Radiochemicals, Irvine, Calif.). Labelled monolayers were resuspended in RIPA buffer (0.15 M NaCl, 1.0% Na-DOC, 1.0% Triton X-100, 0.01 M Tris-Cl pH 7.4) supplemented with protease inhibitors.

Labelled antigen preparations were incubated with both horse polyvalent antiserum and monoclonal antibodies specific for the measles hemagglutinin protein, see McFarlin et al., J. Gen. Viro. 48: 425–29 (1980). Resulting immunologic complexes were precipitated with Staphylococcus protein A (ICN ImmunoBiologicals) as described by Lamb et al., Virology 91: 60–78 (1978).

EXAMPLE 4

EXAMINATION OF DIFFERENTIAL GLYCOSYLATION SITES OF VACCINE AND WILD-TYPE HEMAGGLUTININ ANTIGEN

Differential utilization of glycosylation sites can have an important effect on antigenic determinants. To identify glycosylation sites, the radiolabelled protein lysates were digested overnight with Endoglycosidase F/N-Glycosidase F (Boehringer Mannheim, Indianapolis, Ind.) at 37° C. as previously described by Vialard et al. (1990), supra. After digestion, proteins were precipitated by the addition of 1 ml cold absolute ethanol and electrophoresed through a 8% SDS-Polyacrylamide gel electrophoresis. Following electrophoresis, bands were visualized by autoradiography.

PAGE analysis of the HA proteins of the two 1989 wild-type viruses indicated that these proteins consistently migrated slower than the HA of Moraten (FIG. 3, lanes b-d) and two other vaccine viruses. The apparent molecular size difference could have resulted from the utilization of the new potential glycosylation site at amino acid 416 in the three recent wild-type isolates. Endoglycosidase F (Endo F) was used to treat immunoprecipitated HA protein from radiolabelled infected cell lysates. Although treatment with Endo F reduced the size of all HA proteins, the unglycosylated forms of the wild-type HA proteins maintained the relative size differential indicating that glycosylation differences were not solely responsible for the apparent increased molecular size of the wild-type HA proteins.

What is claimed is:

1. A method for detecting the presence of wild-type measles infection, comprising the steps of:
    (a) preparing for polymerase chain reaction a biological sample suspected of containing a measle virus;
    (b) reverse transcribing mRNA isolated from said sample to cDNA;
    (c) contacting said cDNA with polymerase chain reaction oligonucleotide primers that specifically hybridize to said cDNA at two sites in a nucleic acid encoding a measles hemagglutinin or fusion protein nucleic acid that flank a restriction nuclease site present in a wild-type nucleic acid encoding a polypeptide set forth in SEQ ID NOS:21 or 22, but not present in a vaccine strain nucleic acid, or vice versa;
    (d) performing the polymerase chain reaction to obtain products;
    (e) digesting said products of the polymerase chain reaction such that non-vaccine strain products are produced if a non-vaccine restriction site is present in said wild-type nucleic acid; and
    (f) determining the presence or absence of digested products, thereby identifying the presence or absence of wild-type measles virus in said sample thereby detecting the presence of the infection.

2. A method for detecting the presence or absence of wild-type measles infection, comprising the steps of:
    (a) preparing for polymerase chain reaction a biological sample suspected of containing a measles virus;
    (b) reverse transcribing mRNA isolated from said sample to cDNA;
    (c) contacting said cDNA with polymerase chain reaction oligonucleotide primers that hybridize to said cDNA and amplify at least one wild-type substitution present in a nucleic acid encoding a polypeptide having the amino acid sequence set forth in SEQ ID NOS:21 or 22, but not present in a vaccine strain nucleic acid, or vice versa;
    (d) performing the polymerase chain reaction to obtain products;
    (e) determining the presence or absence of amplification products containing said wild-type substitution, thereby identifying the presence or absence of wild-type measles virus in said sample thereby detecting the presence of the infection.

3. A nucleic acid primer or probe complementary to and containing at least one wild-type substitution in the nucleic acid encoding the consensus hemagglutinin polypeptide of measles virus having the amino acid sequence set forth in the SEQ ID NO:21.

4. A nucleic acid primer or probe complementary to and containing at least one wild-type substitution in the nucleic acid encoding the consensus fusion polypeptide of measles virus having the amino acid sequence set forth in the SEQ ID NO:22.

5. An isolated nucleic acid encoding the consensus hemagglutinin polypeptide of measles virus, wherein the polypeptide has the amino acid sequence set forth in SEQ ID NO:21.

6. An isolated nucleic acid complementary to the nucleic acid of claim 5.

7. A recombinant vector comprising the nucleic acid of claim 6.

8. A recombinant vector comprising the nucleic acid of claim 5.

9. An isolated nucleic acid encoding the consensus fusion polypeptide of measles virus, wherein the polypeptide has the amino acid sequence set forth in the Sequence Listing as SEQ ID NO:22.

10. An isolated nucleic acid complementary to the nucleic acid of claim 5.

11. A recombinant vector comprising the nucleic acid of claim 10.

12. A recombinant vector comprising the nucleic acid of claim 9.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1919 base pairs
        ( B ) TYPE: nucleic acid
        ( C ) STRANDEDNESS: double
        ( D ) TOPOLOGY: linear (ii) MOLECULE TYPE: DNA (genomic)

(vi) ORIGINAL SOURCE:
    (B) STRAIN: Moraten HA (ix) FEATURE:
    (A) NAME/KEY: CDS
    (B) LOCATION: 21..1874

(xi) SEQUENCE DESCRIPTION: SEQ ID NO:1:

```
AGGGTGCAAG ATCATCCACA ATG TCA CCA CAA CGA GAC CGG ATA AAT GCC              50
                     Met Ser Pro Gln Arg Asp Arg Ile Asn Ala
                      1               5                  10

TTC TAC AAA GAT AAC CCC CAT CCC AAG GGA AGT AGG ATA GTC ATT AAC           98
Phe Tyr Lys Asp Asn Pro His Pro Lys Gly Ser Arg Ile Val Ile Asn
             15                  20                  25

AGA GAA CAT CTT ATG ATT GAT AGA CCT TAT GTT TTG CTG GCT GTT CTG          146
Arg Glu His Leu Met Ile Asp Arg Pro Tyr Val Leu Leu Ala Val Leu
             30                  35                  40

TTT GTC ATG TTT CTG AGC TTG ATC GGG TTG CTA GCC ATT GCA GGC ATT          194
Phe Val Met Phe Leu Ser Leu Ile Gly Leu Leu Ala Ile Ala Gly Ile
         45                  50                  55

AGA CTT CAT CGG GCA GCC ATC TAC ACC GCA GAG ATC CAT AAA AGC CTC          242
Arg Leu His Arg Ala Ala Ile Tyr Thr Ala Glu Ile His Lys Ser Leu
     60                  65                  70

AGC ACC AAT CTA GAT GTA ACT AAC TCA ATC GAG CAT CAG GTC AAG GAC          290
Ser Thr Asn Leu Asp Val Thr Asn Ser Ile Glu His Gln Val Lys Asp
 75                  80                  85                  90

GTG CTG ACA CCA CTC TTC AAA ATC ATC GGT GAT GAA GTG GGC CTG AGG          338
Val Leu Thr Pro Leu Phe Lys Ile Ile Gly Asp Glu Val Gly Leu Arg
                 95                 100                 105

ACA CCT CAG AGA TTC ACT GAC CTA GTG AAA TTC ATC TCT GAC AAG ATT          386
Thr Pro Gln Arg Phe Thr Asp Leu Val Lys Phe Ile Ser Asp Lys Ile
             110                 115                 120

AAA TTC CTT AAT CCG GAT AGG GAG TAC GAC TTC AGA GAT CTC ACT TGG          434
Lys Phe Leu Asn Pro Asp Arg Glu Tyr Asp Phe Arg Asp Leu Thr Trp
         125                 130                 135

TGT ATC AAC CCG CCA GAG AGA ATC AAA TTG GAT TAT GAT CAA TAC TGT          482
Cys Ile Asn Pro Pro Glu Arg Ile Lys Leu Asp Tyr Asp Gln Tyr Cys
     140                 145                 150

GCA GAT GTG GCT GCT GAA GAG CTC ATG AAT GCA TTG GTG AAC TCA ACT          530
Ala Asp Val Ala Ala Glu Glu Leu Met Asn Ala Leu Val Asn Ser Thr
155                 160                 165                 170

CTA CTG GAG ACC AGA ACA ACC AAT CAG TTC CTA GCT GTC TCA AAG GGA          578
Leu Leu Glu Thr Arg Thr Thr Asn Gln Phe Leu Ala Val Ser Lys Gly
                 175                 180                 185

AAC TGC TCA GGG CCC ACT ACA ATC AGA GGT CAA TTC TCA AAC ATG TCG          626
Asn Cys Ser Gly Pro Thr Thr Ile Arg Gly Gln Phe Ser Asn Met Ser
             190                 195                 200

CTG TCC CTG TTA GAC TTG TAT TTA GGT CGA GGT TAC AAT GTG TCA TCT          674
Leu Ser Leu Leu Asp Leu Tyr Leu Gly Arg Gly Tyr Asn Val Ser Ser
         205                 210                 215

ATA GTC ACT ATG ACA TCC CAG GGA ATG TAT GGG GGA ACT TAC CTA GTG          722
Ile Val Thr Met Thr Ser Gln Gly Met Tyr Gly Gly Thr Tyr Leu Val
     220                 225                 230

GAA AAG CCT AAT CTG AGC AGC AAA AGG TCA GAG TTG TCA CAA CTG AGC          770
Glu Lys Pro Asn Leu Ser Ser Lys Arg Ser Glu Leu Ser Gln Leu Ser
235                 240                 245                 250

ATG TAC CGA GTG TTT GAA GTA GGT GTT ATC AGA AAT CCG GGT TTG GGG          818
Met Tyr Arg Val Phe Glu Val Gly Val Ile Arg Asn Pro Gly Leu Gly
                 255                 260                 265
```

```
GCT  CCG  GTG  TTC  CAT  ATG  ACA  AAC  TAT  CTT  GAG  CAA  CCA  GTC  AGT  AAT      866
Ala  Pro  Val  Phe  His  Met  Thr  Asn  Tyr  Leu  Glu  Gln  Pro  Val  Ser  Asn
               270                      275                      280

GAT  CTC  AGC  AAC  TGT  ATG  GTG  GCT  TTG  GGG  GAG  CTC  AAA  CTC  GCA  GCC      914
Asp  Leu  Ser  Asn  Cys  Met  Val  Ala  Leu  Gly  Glu  Leu  Lys  Leu  Ala  Ala
          285                      290                      295

CTT  TGT  CAC  GGG  GAA  GAT  TCT  ATC  ACA  ATT  CCC  TAT  CAG  GGA  TCA  GGG      962
Leu  Cys  His  Gly  Glu  Asp  Ser  Ile  Thr  Ile  Pro  Tyr  Gln  Gly  Ser  Gly
     300                      305                      310

AAA  GGT  GTC  AGC  TTC  CAG  CTC  GTC  AAG  CTA  GGT  GTC  TGG  AAA  TCC  CCA     1010
Lys  Gly  Val  Ser  Phe  Gln  Leu  Val  Lys  Leu  Gly  Val  Trp  Lys  Ser  Pro
315                 320                      325                      330

ACC  GAC  ATG  CAA  TCC  TGG  GTC  CCC  TTA  TCA  ACG  GAT  GAT  CCA  GTG  ATA     1058
Thr  Asp  Met  Gln  Ser  Trp  Val  Pro  Leu  Ser  Thr  Asp  Asp  Pro  Val  Ile
               335                      340                      345

GAC  AGG  CTT  TAC  CTC  TCA  TCT  CAC  AGA  GGT  GTT  ATC  GCT  GAC  AAT  CAA     1106
Asp  Arg  Leu  Tyr  Leu  Ser  Ser  His  Arg  Gly  Val  Ile  Ala  Asp  Asn  Gln
          350                      355                      360

GCA  AAA  TGG  GCT  GTC  CCG  ACA  ACA  CGA  ACA  GAT  GAC  AAG  TTG  CGA  ATG     1154
Ala  Lys  Trp  Ala  Val  Pro  Thr  Thr  Arg  Thr  Asp  Asp  Lys  Leu  Arg  Met
     365                      370                      375

GAG  ACA  TGC  TTC  CAA  CAG  GCG  TGT  AAG  GGT  AAA  ATC  CAA  GCA  CTC  TGC     1202
Glu  Thr  Cys  Phe  Gln  Gln  Ala  Cys  Lys  Gly  Lys  Ile  Gln  Ala  Leu  Cys
380                      385                      390

GAG  AAT  CCC  GAG  TGG  GCA  CCA  TTG  AAG  GAT  AAC  AGG  ATT  CCT  TCA  TAC     1250
Glu  Asn  Pro  Glu  Trp  Ala  Pro  Leu  Lys  Asp  Asn  Arg  Ile  Pro  Ser  Tyr
395                      400                      405                      410

GGG  GTC  TTG  TCT  GTT  GAT  CTG  AGT  CTG  ACA  GTT  GAG  CTT  AAA  ATC  AAA     1298
Gly  Val  Leu  Ser  Val  Asp  Leu  Ser  Leu  Thr  Val  Glu  Leu  Lys  Ile  Lys
               415                      420                      425

ATT  GCT  TCG  GGA  TTC  GGG  CCA  TTG  ATC  ACA  CAC  GGT  TCA  GGG  ATG  GAC     1346
Ile  Ala  Ser  Gly  Phe  Gly  Pro  Leu  Ile  Thr  His  Gly  Ser  Gly  Met  Asp
          430                      435                      440

CTA  TAC  AAA  TCC  AAC  CAC  AAC  AAT  GTG  TAT  TGG  CTG  ACT  ATC  CCG  CCA     1394
Leu  Tyr  Lys  Ser  Asn  His  Asn  Asn  Val  Tyr  Trp  Leu  Thr  Ile  Pro  Pro
     445                      450                      455

ATG  AAG  AAC  CTA  GCC  TTA  GGT  GTA  ATC  AAC  ACA  TTG  GAG  TGG  ATA  CCG     1442
Met  Lys  Asn  Leu  Ala  Leu  Gly  Val  Ile  Asn  Thr  Leu  Glu  Trp  Ile  Pro
460                      465                      470

AGA  TTC  AAG  GTT  AGT  CCC  TAC  CTC  TTC  ACT  GTC  CCA  ATT  AAG  GAA  GCA     1490
Arg  Phe  Lys  Val  Ser  Pro  Tyr  Leu  Phe  Thr  Val  Pro  Ile  Lys  Glu  Ala
475                      480                      485                      490

GGC  GAA  GAC  TGC  CAT  GCC  CCA  ACA  TAC  CTA  CCT  GCG  GAG  GTG  GAT  GGT     1538
Gly  Glu  Asp  Cys  His  Ala  Pro  Thr  Tyr  Leu  Pro  Ala  Glu  Val  Asp  Gly
               495                      500                      505

GAT  GTC  AAA  CTC  AGT  TCC  AAT  CTG  GTG  ATT  CTA  CCT  GGT  CAA  GAT  CTC     1586
Asp  Val  Lys  Leu  Ser  Ser  Asn  Leu  Val  Ile  Leu  Pro  Gly  Gln  Asp  Leu
          510                      515                      520

CAA  TAT  GTT  TTG  GCA  ACC  TAC  GAT  ACT  TCC  AGG  GTT  GAA  CAT  GCT  GTG     1634
Gln  Tyr  Val  Leu  Ala  Thr  Tyr  Asp  Thr  Ser  Arg  Val  Glu  His  Ala  Val
     525                      530                      535

GTT  TAT  TAC  GTT  TAC  AGC  CCA  AGC  CGC  TCA  TTT  TCT  TAC  TTT  TAT  CCT     1682
Val  Tyr  Tyr  Val  Tyr  Ser  Pro  Ser  Arg  Ser  Phe  Ser  Tyr  Phe  Tyr  Pro
540                      545                      550

TTT  AGG  TTG  CCT  ATA  AAG  GGG  GTC  CCC  ATC  GAA  TTA  CAA  GTG  GAA  TGC     1730
Phe  Arg  Leu  Pro  Ile  Lys  Gly  Val  Pro  Ile  Glu  Leu  Gln  Val  Glu  Cys
555                      560                      565                      570

TTC  ACA  TGG  GAC  CAA  AAA  CTC  TGG  TGC  CGT  CAC  TTC  TGT  GTG  CTT  GCG     1778
Phe  Thr  Trp  Asp  Gln  Lys  Leu  Trp  Cys  Arg  His  Phe  Cys  Val  Leu  Ala
               575                      580                      585
```

| GAC | TCA | GAA | TCT | GGT | GGA | CAT | ATC | ACT | CAC | TCT | GGG | ATG | GTG | GGC | ATG | 1826 |
| Asp | Ser | Glu | Ser | Gly | Gly | His | Ile | Thr | His | Ser | Gly | Met | Val | Gly | Met | |
| | | | 590 | | | | 595 | | | | | 600 | | | | |

| GGA | GTC | AGC | TGC | ACA | GTC | ACC | CGG | GAA | GAT | GGA | ACC | AAT | CGC | AGA | | 1871 |
| Gly | Val | Ser | Cys | Thr | Val | Thr | Arg | Glu | Asp | Gly | Thr | Asn | Arg | Arg | | |
| | | 605 | | | | | 610 | | | | | 615 | | | | |

TAGGGCTGCT 1881

AGTGAACCAA TCTCATGATG TCACCCAGAC ATCAGGCA 1919

( 2 ) INFORMATION FOR SEQ ID NO:2:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ser | Pro | Gln | Arg | Asp | Arg | Ile | Asn | Ala | Phe | Tyr | Lys | Asp | Asn | Pro |
| 1 | | | | 5 | | | | | 10 | | | | | 15 | |

| His | Pro | Lys | Gly | Ser | Arg | Ile | Val | Ile | Asn | Arg | Glu | His | Leu | Met | Ile |
| | | | 20 | | | | | 25 | | | | | 30 | | |

| Asp | Arg | Pro | Tyr | Val | Leu | Leu | Ala | Val | Leu | Phe | Val | Met | Phe | Leu | Ser |
| | | 35 | | | | | 40 | | | | | 45 | | | |

| Leu | Ile | Gly | Leu | Leu | Ala | Ile | Ala | Gly | Ile | Arg | Leu | His | Arg | Ala | Ala |
| | 50 | | | | | 55 | | | | | 60 | | | | |

| Ile | Tyr | Thr | Ala | Glu | Ile | His | Lys | Ser | Leu | Ser | Thr | Asn | Leu | Asp | Val |
| 65 | | | | | 70 | | | | | 75 | | | | | 80 |

| Thr | Asn | Ser | Ile | Glu | His | Gln | Val | Lys | Asp | Val | Leu | Thr | Pro | Leu | Phe |
| | | | | 85 | | | | | 90 | | | | | 95 | |

| Lys | Ile | Ile | Gly | Asp | Glu | Val | Gly | Leu | Arg | Thr | Pro | Gln | Arg | Phe | Thr |
| | | | 100 | | | | | 105 | | | | | 110 | | |

| Asp | Leu | Val | Lys | Phe | Ile | Ser | Asp | Lys | Ile | Lys | Phe | Leu | Asn | Pro | Asp |
| | | 115 | | | | | 120 | | | | | 125 | | | |

| Arg | Glu | Tyr | Asp | Phe | Arg | Asp | Leu | Thr | Trp | Cys | Ile | Asn | Pro | Pro | Glu |
| | 130 | | | | | 135 | | | | | 140 | | | | |

| Arg | Ile | Lys | Leu | Asp | Tyr | Asp | Gln | Tyr | Cys | Ala | Asp | Val | Ala | Ala | Glu |
| 145 | | | | | 150 | | | | | 155 | | | | | 160 |

| Glu | Leu | Met | Asn | Ala | Leu | Val | Asn | Ser | Thr | Leu | Leu | Glu | Thr | Arg | Thr |
| | | | | 165 | | | | | 170 | | | | | 175 | |

| Thr | Asn | Gln | Phe | Leu | Ala | Val | Ser | Lys | Gly | Asn | Cys | Ser | Gly | Pro | Thr |
| | | | 180 | | | | | 185 | | | | | 190 | | |

| Thr | Ile | Arg | Gly | Gln | Phe | Ser | Asn | Met | Ser | Leu | Ser | Leu | Leu | Asp | Leu |
| | | 195 | | | | | 200 | | | | | 205 | | | |

| Tyr | Leu | Gly | Arg | Gly | Tyr | Asn | Val | Ser | Ser | Ile | Val | Thr | Met | Thr | Ser |
| | 210 | | | | | 215 | | | | | 220 | | | | |

| Gln | Gly | Met | Tyr | Gly | Gly | Thr | Tyr | Leu | Val | Glu | Lys | Pro | Asn | Leu | Ser |
| 225 | | | | | 230 | | | | | 235 | | | | | 240 |

| Ser | Lys | Arg | Ser | Glu | Leu | Ser | Gln | Leu | Ser | Met | Tyr | Arg | Val | Phe | Glu |
| | | | | 245 | | | | | 250 | | | | | 255 | |

| Val | Gly | Val | Ile | Arg | Asn | Pro | Gly | Leu | Gly | Ala | Pro | Val | Phe | His | Met |
| | | | 260 | | | | | 265 | | | | | 270 | | |

| Thr | Asn | Tyr | Leu | Glu | Gln | Pro | Val | Ser | Asn | Asp | Leu | Ser | Asn | Cys | Met |
| | | 275 | | | | | 280 | | | | | 285 | | | |

| Val | Ala | Leu | Gly | Glu | Leu | Lys | Leu | Ala | Ala | Leu | Cys | His | Gly | Glu | Asp |
| | 290 | | | | | 295 | | | | | 300 | | | | |

| Ser | Ile | Thr | Ile | Pro | Tyr | Gln | Gly | Ser | Gly | Lys | Gly | Val | Ser | Phe | Gln |
| 305 | | | | | 310 | | | | 315 | | | | | | 320 |

| Leu | Val | Lys | Leu | Gly | Val | Trp | Lys | Ser | Pro | Thr | Asp | Met | Gln | Ser | Trp |
| | | | | 325 | | | | | 330 | | | | | 335 | |

| Val | Pro | Leu | Ser | Thr | Asp | Asp | Pro | Val | Ile | Asp | Arg | Leu | Tyr | Leu | Ser |
| | | | 340 | | | | | 345 | | | | | 350 | | |

| Ser | His | Arg | Gly | Val | Ile | Ala | Asp | Asn | Gln | Ala | Lys | Trp | Ala | Val | Pro |
| | | 355 | | | | | 360 | | | | | 365 | | | |

| Thr | Thr | Arg | Thr | Asp | Asp | Lys | Leu | Arg | Met | Glu | Thr | Cys | Phe | Gln | Gln |
| | 370 | | | | | 375 | | | | | 380 | | | | |

| Ala | Cys | Lys | Gly | Lys | Ile | Gln | Ala | Leu | Cys | Glu | Asn | Pro | Glu | Trp | Ala |
| 385 | | | | | 390 | | | | | 395 | | | | | 400 |

| Pro | Leu | Lys | Asp | Asn | Arg | Ile | Pro | Ser | Tyr | Gly | Val | Leu | Ser | Val | Asp |
| | | | | 405 | | | | | 410 | | | | | 415 | |

| Leu | Ser | Leu | Thr | Val | Glu | Leu | Lys | Ile | Lys | Ile | Ala | Ser | Gly | Phe | Gly |
| | | | 420 | | | | | 425 | | | | | 430 | | |

| Pro | Leu | Ile | Thr | His | Gly | Ser | Gly | Met | Asp | Leu | Tyr | Lys | Ser | Asn | His |
| | | | 435 | | | | 440 | | | | | 445 | | | |

| Asn | Asn | Val | Tyr | Trp | Leu | Thr | Ile | Pro | Pro | Met | Lys | Asn | Leu | Ala | Leu |
| | 450 | | | | | 455 | | | | | 460 | | | | |

| Gly | Val | Ile | Asn | Thr | Leu | Glu | Trp | Ile | Pro | Arg | Phe | Lys | Val | Ser | Pro |
| 465 | | | | | 470 | | | | | 475 | | | | | 480 |

| Tyr | Leu | Phe | Thr | Val | Pro | Ile | Lys | Glu | Ala | Gly | Glu | Asp | Cys | His | Ala |
| | | | | 485 | | | | | 490 | | | | | 495 | |

| Pro | Thr | Tyr | Leu | Pro | Ala | Glu | Val | Asp | Gly | Asp | Val | Lys | Leu | Ser | Ser |
| | | | 500 | | | | | 505 | | | | | 510 | | |

| Asn | Leu | Val | Ile | Leu | Pro | Gly | Gln | Asp | Leu | Gln | Tyr | Val | Leu | Ala | Thr |
| | | 515 | | | | | 520 | | | | | 525 | | | |

| Tyr | Asp | Thr | Ser | Arg | Val | Glu | His | Ala | Val | Val | Tyr | Tyr | Val | Tyr | Ser |
| | | 530 | | | | 535 | | | | | 540 | | | | |

| Pro | Ser | Arg | Ser | Phe | Ser | Tyr | Phe | Tyr | Pro | Phe | Arg | Leu | Pro | Ile | Lys |
| 545 | | | | | 550 | | | | | 555 | | | | | 560 |

| Gly | Val | Pro | Ile | Glu | Leu | Gln | Val | Glu | Cys | Phe | Thr | Trp | Asp | Gln | Lys |
| | | | | 565 | | | | | 570 | | | | | 575 | |

| Leu | Trp | Cys | Arg | His | Phe | Cys | Val | Leu | Ala | Asp | Ser | Glu | Ser | Gly | Gly |
| | | | 580 | | | | | 585 | | | | | 590 | | |

| His | Ile | Thr | His | Ser | Gly | Met | Val | Gly | Met | Gly | Val | Ser | Cys | Thr | Val |
| | | | 595 | | | | 600 | | | | | 605 | | | |

| Thr | Arg | Glu | Asp | Gly | Thr | Asn | Arg | Arg |
| | 610 | | | | | 615 | | |

( 2 ) INFORMATION FOR SEQ ID NO:3:

( i ) SEQUENCE CHARACTERISTICS:
        ( A ) LENGTH: 1874 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 21..1874

( x i ) SEQUENCE DESCRIPTION: SEQ ID NO:3:

```
AGGGTGCAAG ATCATCCACA ATG TCA CCA CAC CGA GAC CGA ATA AAT GCC        50
                      Met Ser Pro His Arg Asp Arg Ile Asn Ala
```

| | | | | | | | | | | | | | | | | |
|---|---|---|---|---|---|---|---|---|---|---|---|---|---|---|---|---|
| | | | | 1 | | | | 5 | | | | | | 10 | | |
| TTC | TAC | AAA | GAC | AAC | CCC | CAT | CCT | AAG | GGA | AGT | AGG | ATA | GTT | ATT | AAC | 98 |
| Phe | Tyr | Lys | Asp | Asn | Pro | His | Pro | Lys | Gly | Ser | Arg | Ile | Val | Ile | Asn | |
| | | | | 15 | | | | 20 | | | | | | 25 | | |
| AGA | GAA | CAT | CTT | ATG | ATT | GAT | AGA | CCT | TAT | GTT | TTG | CTG | GCT | GTT | CTA | 146 |
| Arg | Glu | His | Leu | Met | Ile | Asp | Arg | Pro | Tyr | Val | Leu | Leu | Ala | Val | Leu | |
| | | | 30 | | | | 35 | | | | | 40 | | | | |
| TTC | GTC | ATG | TTT | CTG | AGC | TTG | ATC | GGG | TTG | CTA | GCC | ATT | GCA | GGC | ATT | 194 |
| Phe | Val | Met | Phe | Leu | Ser | Leu | Ile | Gly | Leu | Leu | Ala | Ile | Ala | Gly | Ile | |
| | | 45 | | | | 50 | | | | | 55 | | | | | |
| AGA | CTC | CAT | CGG | GCA | GCC | ATC | TAC | ACC | GCA | GAG | ATC | CAT | AAG | AGC | CTC | 242 |
| Arg | Leu | His | Arg | Ala | Ala | Ile | Tyr | Thr | Ala | Glu | Ile | His | Lys | Ser | Leu | |
| 60 | | | | | 65 | | | | | 70 | | | | | | |
| AGC | ACC | AAT | CTA | GAT | GTA | ACT | AAC | TCA | ATC | GAG | CAT | CAG | GTC | AAG | GAC | 290 |
| Ser | Thr | Asn | Leu | Asp | Val | Thr | Asn | Ser | Ile | Glu | His | Gln | Val | Lys | Asp | |
| 75 | | | | | 80 | | | | | 85 | | | | | 90 | |
| GTG | CTG | ACA | CCA | CTC | TTC | AAG | ATC | ATC | GGT | GAT | GAA | GTG | GGC | CTG | AGG | 338 |
| Val | Leu | Thr | Pro | Leu | Phe | Lys | Ile | Ile | Gly | Asp | Glu | Val | Gly | Leu | Arg | |
| | | | | 95 | | | | 100 | | | | | | 105 | | |
| ACA | CCT | CAG | AGA | TTC | ACT | GAC | CTA | GTG | AAA | TTC | ATC | TCT | GAC | AAA | ATT | 386 |
| Thr | Pro | Gln | Arg | Phe | Thr | Asp | Leu | Val | Lys | Phe | Ile | Ser | Asp | Lys | Ile | |
| | | | 110 | | | | | 115 | | | | | 120 | | | |
| AAA | TTC | CTT | AAT | CCG | GAT | AGG | GAG | TAC | GAC | TTC | AGA | GAT | CTC | ACT | TGG | 434 |
| Lys | Phe | Leu | Asn | Pro | Asp | Arg | Glu | Tyr | Asp | Phe | Arg | Asp | Leu | Thr | Trp | |
| | | 125 | | | | | 130 | | | | | | 135 | | | |
| TGT | ATC | AAC | CCG | CCA | GAG | AGA | ATC | AAA | TTG | GAT | TAT | GAT | CAA | TAC | TGT | 482 |
| Cys | Ile | Asn | Pro | Pro | Glu | Arg | Ile | Lys | Leu | Asp | Tyr | Asp | Gln | Tyr | Cys | |
| | 140 | | | | | 145 | | | | | 150 | | | | | |
| GCA | GAT | GTG | GCT | GCT | GAA | GAA | CTC | ATG | AAT | GCA | TTG | GTG | AAC | TCA | ACT | 530 |
| Ala | Asp | Val | Ala | Ala | Glu | Glu | Leu | Met | Asn | Ala | Leu | Val | Asn | Ser | Thr | |
| 155 | | | | | 160 | | | | | 165 | | | | | 170 | |
| CTA | CTG | GAG | GCC | AGG | GCA | ACC | AAT | CAG | TTC | CTA | GCT | GTC | TCA | AAG | GGA | 578 |
| Leu | Leu | Glu | Ala | Arg | Ala | Thr | Asn | Gln | Phe | Leu | Ala | Val | Ser | Lys | Gly | |
| | | | | 175 | | | | | 180 | | | | | 185 | | |
| AAC | TGC | TCA | GGG | CCC | ACT | ACA | ATC | AGA | GGT | CAA | TTC | TCA | AAC | ATG | TCG | 626 |
| Asn | Cys | Ser | Gly | Pro | Thr | Thr | Ile | Arg | Gly | Gln | Phe | Ser | Asn | Met | Ser | |
| | | | 190 | | | | | 195 | | | | | 200 | | | |
| CTG | TCC | CTG | TTG | GAC | TTG | TAT | TTA | AGT | CGA | GGT | TAC | AAT | GTG | TCA | TCT | 674 |
| Leu | Ser | Leu | Leu | Asp | Leu | Tyr | Leu | Ser | Arg | Gly | Tyr | Asn | Val | Ser | Ser | |
| | | 205 | | | | | 210 | | | | | 215 | | | | |
| ATA | GTC | ACC | ATG | ACA | TCC | CAG | GGA | ATG | TAC | GGG | GGA | ACT | TAC | CTA | GTG | 722 |
| Ile | Val | Thr | Met | Thr | Ser | Gln | Gly | Met | Tyr | Gly | Gly | Thr | Tyr | Leu | Val | |
| | 220 | | | | | 225 | | | | | 230 | | | | | |
| GGA | AAG | CCT | AAT | CTG | AGC | AGT | AAA | GGG | TCA | GAG | TTG | TCA | CAA | CTG | AGC | 770 |
| Gly | Lys | Pro | Asn | Leu | Ser | Ser | Lys | Gly | Ser | Glu | Leu | Ser | Gln | Leu | Ser | |
| 235 | | | | | 240 | | | | | 245 | | | | | 250 | |
| ATG | CAC | CGA | GTG | TTT | GAA | GTA | GGG | GTT | ATC | AGA | AAT | CCG | GGT | TTG | GGG | 818 |
| Met | His | Arg | Val | Phe | Glu | Val | Gly | Val | Ile | Arg | Asn | Pro | Gly | Leu | Gly | |
| | | | | 255 | | | | | 260 | | | | | 265 | | |
| GCT | CCG | GTG | TTC | CAT | ATG | ACA | AAC | TAT | TTT | GAG | CAA | CCA | GTC | AGT | AAT | 866 |
| Ala | Pro | Val | Phe | His | Met | Thr | Asn | Tyr | Phe | Glu | Gln | Pro | Val | Ser | Asn | |
| | | | | 270 | | | | 275 | | | | | 280 | | | |
| GAT | TTC | AGC | AAC | TGC | ATG | GTG | GCT | TTG | GGG | GAG | CTC | AGG | TTC | GCA | GCC | 914 |
| Asp | Phe | Ser | Asn | Cys | Met | Val | Ala | Leu | Gly | Glu | Leu | Arg | Phe | Ala | Ala | |
| | | | 285 | | | | | 290 | | | | | 295 | | | |
| CTC | TGT | CAC | AGG | GAA | GAT | TCT | GTC | ACG | GTT | CCC | TAT | CAG | GGG | TCA | GGG | 962 |
| Leu | Cys | His | Arg | Glu | Asp | Ser | Val | Thr | Val | Pro | Tyr | Gln | Gly | Ser | Gly | |
| | | 300 | | | | | 305 | | | | | 310 | | | | |
| AAA | GGT | GTC | AGC | TTC | CAG | CTC | GTC | AAG | CTA | GGT | GTC | TGG | AAA | TCC | CCA | 1010 |
| Lys | Gly | Val | Ser | Phe | Gln | Leu | Val | Lys | Leu | Gly | Val | Trp | Lys | Ser | Pro | |

```
      315                           320                           325                           330
ACC  GAC  ATG  CAA  TCC  TGG  GTC  CCC  CTA  TCA  ACG  GAT  GAT  CCA  GTG  ATA        1058
Thr  Asp  Met  Gln  Ser  Trp  Val  Pro  Leu  Ser  Thr  Asp  Asp  Pro  Val  Ile
                         335                      340                      345

GAT  AGG  CTT  TAC  CTC  TCA  TCT  CAC  AGA  GGT  GTT  ATC  GCT  GAC  AAT  CAA        1106
Asp  Arg  Leu  Tyr  Leu  Ser  Ser  His  Arg  Gly  Val  Ile  Ala  Asp  Asn  Gln
               350                      355                      360

GCA  AAA  TGG  GCT  GTC  CCG  ACA  ACA  CGG  ACA  GAT  GAC  AAG  TTG  CGA  ATG        1154
Ala  Lys  Trp  Ala  Val  Pro  Thr  Thr  Arg  Thr  Asp  Asp  Lys  Leu  Arg  Met
          365                      370                      375

GAG  ACA  TGC  TTC  CAG  CAG  GCG  TGT  AAG  GGT  AAA  AAC  CAA  GCA  CTC  TGC        1202
Glu  Thr  Cys  Phe  Gln  Gln  Ala  Cys  Lys  Gly  Lys  Asn  Gln  Ala  Leu  Cys
     380                      385                      390

GAG  AAT  CCC  GAG  TGG  GCA  CCA  TTG  AAG  GAT  AAC  AGG  ATT  CCT  TCA  TAC        1250
Glu  Asn  Pro  Glu  Trp  Ala  Pro  Leu  Lys  Asp  Asn  Arg  Ile  Pro  Ser  Tyr
395                      400                      405                      410

GGG  GTC  TTG  TCT  GTT  AAT  CTG  AGT  CTG  ACA  GTT  GAG  CTT  AAA  ATC  AAA        1298
Gly  Val  Leu  Ser  Val  Asn  Leu  Ser  Leu  Thr  Val  Glu  Leu  Lys  Ile  Lys
               415                      420                      425

ATT  GCT  TCA  GGA  TTC  GGG  CCA  TTG  ATC  ACA  CAC  GGT  TCA  GGG  ATG  GAC        1346
Ile  Ala  Ser  Gly  Phe  Gly  Pro  Leu  Ile  Thr  His  Gly  Ser  Gly  Met  Asp
               430                      435                      440

CTA  TAC  AAA  ACC  AAC  CAC  AAC  AAT  GTG  TAT  TGG  CTG  ACT  ATC  CCG  CCA        1394
Leu  Tyr  Lys  Thr  Asn  His  Asn  Asn  Val  Tyr  Trp  Leu  Thr  Ile  Pro  Pro
               445                      450                      455

ATG  AAG  AAC  CTA  GCC  TTA  GGT  GTA  ATC  AAC  ACA  TTG  GAG  TGG  ATA  CCG        1442
Met  Lys  Asn  Leu  Ala  Leu  Gly  Val  Ile  Asn  Thr  Leu  Glu  Trp  Ile  Pro
     460                      465                      470

AGA  TTC  AAG  GTT  AGT  CCC  AAC  CTC  TTC  ACT  GTT  CCA  ATC  AAG  GAA  GCA        1490
Arg  Phe  Lys  Val  Ser  Pro  Asn  Leu  Phe  Thr  Val  Pro  Ile  Lys  Glu  Ala
475                      480                      485                      490

GGC  GAG  GAC  TGC  CAT  GCC  CCA  ACA  TAC  CTA  CCT  GCG  GAG  GTG  GAT  GGT        1538
Gly  Glu  Asp  Cys  His  Ala  Pro  Thr  Tyr  Leu  Pro  Ala  Glu  Val  Asp  Gly
               495                      500                      505

GAT  GTC  AAA  CTC  AGT  TCC  AAT  CTG  GTA  ATT  CTA  CCT  GGT  CAG  GAT  CTC        1586
Asp  Val  Lys  Leu  Ser  Ser  Asn  Leu  Val  Ile  Leu  Pro  Gly  Gln  Asp  Leu
          510                      515                      520

CAA  TAT  GTT  TTG  GCA  ACC  TAC  GAT  ACT  TCC  AGG  GTT  GAA  CAT  GCT  GTG        1634
Gln  Tyr  Val  Leu  Ala  Thr  Tyr  Asp  Thr  Ser  Arg  Val  Glu  His  Ala  Val
          525                      530                      535

GTT  TAT  TAT  GTT  TAC  AGC  CCA  AGC  CGC  TCA  TTT  TCT  TAC  TTT  TAT  CCT        1682
Val  Tyr  Tyr  Val  Tyr  Ser  Pro  Ser  Arg  Ser  Phe  Ser  Tyr  Phe  Tyr  Pro
     540                      545                      550

TTT  AGG  TTG  CCT  ATA  AAG  GGG  GTC  CCA  ATC  GAA  TTA  CAA  GTG  GAA  TGC        1730
Phe  Arg  Leu  Pro  Ile  Lys  Gly  Val  Pro  Ile  Glu  Leu  Gln  Val  Glu  Cys
555                      560                      565                      570

TTC  ACA  TGG  GAC  CAA  AAA  CTC  TGG  TGC  CGT  CAC  TTC  TGT  GTG  CTT  GCG        1778
Phe  Thr  Trp  Asp  Gln  Lys  Leu  Trp  Cys  Arg  His  Phe  Cys  Val  Leu  Ala
               575                      580                      585

GAT  TCA  GAA  TCT  GGT  GGA  CAT  ATC  ACT  CAC  TCT  GGG  ATG  GTG  GGC  ATG        1826
Asp  Ser  Glu  Ser  Gly  Gly  His  Ile  Thr  His  Ser  Gly  Met  Val  Gly  Met
               590                      595                      600

GGA  GTC  AGC  TGC  ACA  GTC  ACT  CGG  GAA  GAT  GGA  ACC  AAT  CGC  AGA  TAG        1874
Gly  Val  Ser  Cys  Thr  Val  Thr  Arg  Glu  Asp  Gly  Thr  Asn  Arg  Arg
          605                      610                      615
```

( 2 ) INFORMATION FOR SEQ ID NO:4:

( i ) SEQUENCE CHARACTERISTICS:
       ( A ) LENGTH: 617 amino acids
       ( B ) TYPE: amino acid (D) TOPOLOGY: linear (ii) MOLECULE TYPE: protein (xi) SEQUENCE DESCRIPTION: SEQ ID NO:4:

```
Met Ser Pro His Arg Asp Arg Ile Asn Ala Phe Tyr Lys Asp Asn Pro
 1               5                  10                      15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
            35                  40                  45

Leu Ile Gly Leu Leu Ala Ile Ala Gly Ile Arg Leu His Arg Ala Ala
        50                  55                  60

Ile Tyr Thr Ala Glu Ile His Lys Ser Leu Ser Thr Asn Leu Asp Val
65                  70                  75                      80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
            115                 120                 125

Arg Glu Tyr Asp Phe Arg Asp Leu Thr Trp Cys Ile Asn Pro Pro Glu
130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Ala Arg Ala
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
            195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Gly Lys Pro Asn Leu Ser
225                 230                 235                 240

Ser Lys Gly Ser Glu Leu Ser Gln Leu Ser Met His Arg Val Phe Glu
            245                 250                 255

Val Gly Val Ile Arg Asn Pro Gly Leu Gly Ala Pro Val Phe His Met
            260                 265                 270

Thr Asn Tyr Phe Glu Gln Pro Val Ser Asn Asp Phe Ser Asn Cys Met
    275                 280                 285

Val Ala Leu Gly Glu Leu Arg Phe Ala Ala Leu Cys His Arg Glu Asp
290                 295                 300

Ser Val Thr Val Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
            325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365

Thr Thr Arg Thr Asp Asp Lys Leu Arg Met Glu Thr Cys Phe Gln Gln
    370                 375                 380

Ala Cys Lys Gly Lys Asn Gln Ala Leu Cys Glu Asn Pro Glu Trp Ala
385                 390                 395                 400
```

| | | | | | | | | | | | | | | |
|---|---|---|---|---|---|---|---|---|---|---|---|---|---|---|
| Pro | Leu | Lys | Asp | Asn | Arg | Ile | Pro | Ser | Tyr | Gly | Val | Leu | Ser | Val | Asn |
| | | | | 405 | | | | | 410 | | | | | 415 | |
| Leu | Ser | Leu | Thr | Val | Glu | Leu | Lys | Ile | Lys | Ile | Ala | Ser | Gly | Phe | Gly |
| | | | 420 | | | | | 425 | | | | | 430 | | |
| Pro | Leu | Ile | Thr | His | Gly | Ser | Gly | Met | Asp | Leu | Tyr | Lys | Thr | Asn | His |
| | | 435 | | | | | 440 | | | | | 445 | | | |
| Asn | Asn | Val | Tyr | Trp | Leu | Thr | Ile | Pro | Pro | Met | Lys | Asn | Leu | Ala | Leu |
| | 450 | | | | | 455 | | | | 460 | | | | | |
| Gly | Val | Ile | Asn | Thr | Leu | Glu | Trp | Ile | Pro | Arg | Phe | Lys | Val | Ser | Pro |
| 465 | | | | | 470 | | | | | 475 | | | | | 480 |
| Asn | Leu | Phe | Thr | Val | Pro | Ile | Lys | Glu | Ala | Gly | Glu | Asp | Cys | His | Ala |
| | | | | 485 | | | | | 490 | | | | | 495 | |
| Pro | Thr | Tyr | Leu | Pro | Ala | Glu | Val | Asp | Gly | Asp | Val | Lys | Leu | Ser | Ser |
| | | | 500 | | | | | 505 | | | | | 510 | | |
| Asn | Leu | Val | Ile | Leu | Pro | Gly | Gln | Asp | Leu | Gln | Tyr | Val | Leu | Ala | Thr |
| | | 515 | | | | | 520 | | | | | 525 | | | |
| Tyr | Asp | Thr | Ser | Arg | Val | Glu | His | Ala | Val | Val | Tyr | Tyr | Val | Tyr | Ser |
| | 530 | | | | | 535 | | | | | 540 | | | | |
| Pro | Ser | Arg | Ser | Phe | Ser | Tyr | Phe | Tyr | Pro | Phe | Arg | Leu | Pro | Ile | Lys |
| 545 | | | | | 550 | | | | | 555 | | | | | 560 |
| Gly | Val | Pro | Ile | Glu | Leu | Gln | Val | Glu | Cys | Phe | Thr | Trp | Asp | Gln | Lys |
| | | | | 565 | | | | | 570 | | | | | 575 | |
| Leu | Trp | Cys | Arg | His | Phe | Cys | Val | Leu | Ala | Asp | Ser | Glu | Ser | Gly | Gly |
| | | | 580 | | | | | 585 | | | | | 590 | | |
| His | Ile | Thr | His | Ser | Gly | Met | Val | Gly | Met | Gly | Val | Ser | Cys | Thr | Val |
| | | 595 | | | | | 600 | | | | | 605 | | | |
| Thr | Arg | Glu | Asp | Gly | Thr | Asn | Arg | Arg | | | | | | | |
| | 610 | | | | | 615 | | | | | | | | | |

( 2 ) INFORMATION FOR SEQ ID NO:5:

( i ) SEQUENCE CHARACTERISTICS:
        ( A ) LENGTH: 1919 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: San Diego HA ( i x ) FEATURE:
        ( A ) NAME/KEY: CDS
        ( B ) LOCATION: 21..1874

( x i ) SEQUENCE DESCRIPTION: SEQ ID NO:5:

```
AGGGTGCAAG ATCATCCACA ATG TCA CCA CAC CGA GAC CGA ATA AAT GCC           50
                    Met Ser Pro His Arg Asp Arg Ile Asn Ala
                      1               5                  10

TTC TAC AAA GAC AAC CCC CAT CCT AAG GGA AGT AGG ATA GTT ATT AAC          98
Phe Tyr Lys Asp Asn Pro His Pro Lys Gly Ser Arg Ile Val Ile Asn
                  15                  20                  25

AGA GAA CAT CTT ATG ATT GAT CGA CCT TAT GTT TTG CTG GCT GTT CTA         146
Arg Glu His Leu Met Ile Asp Arg Pro Tyr Val Leu Leu Ala Val Leu
              30                  35                  40

TTC GTC ATG TTT CTG AGC TTG ATC GGG TTG CTA GCC ATT GCA GGC ATT         194
Phe Val Met Phe Leu Ser Leu Ile Gly Leu Leu Ala Ile Ala Gly Ile
          45                  50                  55

AGA CTC CAT CGG GCA GCC ATC TAC ACC GCA GAG ATC CAT AAG AGC CTC         242
```

| | | | | | | | | | | | | | | | | |
|---|---|---|---|---|---|---|---|---|---|---|---|---|---|---|---|---|
| Arg | Leu | His | Arg | Ala | Ala | Ile | Tyr | Thr | Ala | Glu | Ile | His | Lys | Ser | Leu | |
| | 60 | | | | 65 | | | | | 70 | | | | | | |
| AGC | ACC | AAT | CTA | GAT | GTA | ACT | AAC | TCA | ATC | GAG | CAT | CAG | GTC | AAG | GAC | 290 |
| Ser | Thr | Asn | Leu | Asp | Val | Thr | Asn | Ser | Ile | Glu | His | Gln | Val | Lys | Asp | |
| 75 | | | | 80 | | | | | 85 | | | | | 90 | | |
| GTG | CTG | ACA | CCA | CTC | TTC | AAG | ATC | ATC | GGT | GAT | GAA | GTG | GGC | CTG | AGG | 338 |
| Val | Leu | Thr | Pro | Leu | Phe | Lys | Ile | Ile | Gly | Asp | Glu | Val | Gly | Leu | Arg | |
| | | | | 95 | | | | | 100 | | | | | 105 | | |
| ACA | CCT | CAG | AGA | TTC | ACT | GAC | CTA | GTG | AAA | TTC | ATC | TCT | GAC | AAA | ATT | 386 |
| Thr | Pro | Gln | Arg | Phe | Thr | Asp | Leu | Val | Lys | Phe | Ile | Ser | Asp | Lys | Ile | |
| | | | 110 | | | | | 115 | | | | | 120 | | | |
| AAA | TTC | CTT | AAT | CCG | GAT | AGG | GAG | TAC | GAC | TTC | AGA | GAT | CTC | ACT | TGG | 434 |
| Lys | Phe | Leu | Asn | Pro | Asp | Arg | Glu | Tyr | Asp | Phe | Arg | Asp | Leu | Thr | Trp | |
| | | 125 | | | | | 130 | | | | | 135 | | | | |
| TGT | ATC | AAC | CCG | CCA | GAG | AGA | ATC | AAA | TTG | GAT | TAT | GAT | CAA | TAC | TGT | 482 |
| Cys | Ile | Asn | Pro | Pro | Glu | Arg | Ile | Lys | Leu | Asp | Tyr | Asp | Gln | Tyr | Cys | |
| | 140 | | | | | 145 | | | | | 150 | | | | | |
| GCA | GAT | GTG | GCT | GCT | GAA | GAA | CTC | ATG | AAT | GCA | TTG | GTG | AAC | TCA | ACT | 530 |
| Ala | Asp | Val | Ala | Ala | Glu | Glu | Leu | Met | Asn | Ala | Leu | Val | Asn | Ser | Thr | |
| 155 | | | | | 160 | | | | | 165 | | | | | 170 | |
| CTA | CTG | GAG | GCC | AGG | GCA | ACC | AAT | CAG | TTC | CTA | GCT | GTC | TCA | AAG | GGA | 578 |
| Leu | Leu | Glu | Ala | Arg | Ala | Thr | Asn | Gln | Phe | Leu | Ala | Val | Ser | Lys | Gly | |
| | | | | 175 | | | | | 180 | | | | | 185 | | |
| AAC | TGC | TCA | GGG | CCC | ACT | ACA | ATC | AGA | GGT | CAA | TTC | TCA | AAC | ATG | TCG | 626 |
| Asn | Cys | Ser | Gly | Pro | Thr | Thr | Ile | Arg | Gly | Gln | Phe | Ser | Asn | Met | Ser | |
| | | | 190 | | | | | 195 | | | | | 200 | | | |
| CTG | TCC | CTG | TTG | GAC | TTG | TAT | TTA | AGT | CGA | GGT | TAC | AAT | GTG | TCA | TCT | 674 |
| Leu | Ser | Leu | Leu | Asp | Leu | Tyr | Leu | Ser | Arg | Gly | Tyr | Asn | Val | Ser | Ser | |
| | | 205 | | | | | 210 | | | | | 215 | | | | |
| ATA | GTC | ACC | ATG | ACA | TCC | CAG | GGA | ATG | TAC | GGG | GGA | ACT | TAC | CTA | GTG | 722 |
| Ile | Val | Thr | Met | Thr | Ser | Gln | Gly | Met | Tyr | Gly | Gly | Thr | Tyr | Leu | Val | |
| | 220 | | | | | 225 | | | | | 230 | | | | | |
| GGA | AAG | CCT | AAT | CTG | AGC | AGT | AAA | GGG | TCA | GAG | TTG | TCA | CAA | CTG | AGC | 770 |
| Gly | Lys | Pro | Asn | Leu | Ser | Ser | Lys | Gly | Ser | Glu | Leu | Ser | Gln | Leu | Ser | |
| 235 | | | | | 240 | | | | | 245 | | | | | 250 | |
| ATG | CAC | CGA | GTG | TTT | GAA | GTA | GGG | GTT | ATC | AGA | AAT | CCG | GGT | TTG | GGG | 818 |
| Met | His | Arg | Val | Phe | Glu | Val | Gly | Val | Ile | Arg | Asn | Pro | Gly | Leu | Gly | |
| | | | | 255 | | | | | 260 | | | | | 265 | | |
| GCT | CCG | GTG | TTC | CAT | ATG | ACA | AAC | TAT | TTT | GAG | CAA | CCA | GTC | AGT | AAT | 866 |
| Ala | Pro | Val | Phe | His | Met | Thr | Asn | Tyr | Phe | Glu | Gln | Pro | Val | Ser | Asn | |
| | | | 270 | | | | | 275 | | | | | 280 | | | |
| GAT | TTC | AGC | AAC | TGC | ATG | GTG | GCT | TTG | GGG | GAG | CTC | AGG | TTC | GCA | GCC | 914 |
| Asp | Phe | Ser | Asn | Cys | Met | Val | Ala | Leu | Gly | Glu | Leu | Arg | Phe | Ala | Ala | |
| | | 285 | | | | | 290 | | | | | 295 | | | | |
| CTC | TGT | CAC | AGG | GAA | GAT | TCT | GTC | ACG | GTT | CCC | TAT | CAG | GGG | TCA | GGG | 962 |
| Leu | Cys | His | Arg | Glu | Asp | Ser | Val | Thr | Val | Pro | Tyr | Gln | Gly | Ser | Gly | |
| | 300 | | | | | 305 | | | | | 310 | | | | | |
| AAA | GGT | GTC | AGC | TTC | CAG | CTC | GTC | AAG | CTA | GGT | GTC | TGG | AAA | TCC | CCA | 1010 |
| Lys | Gly | Val | Ser | Phe | Gln | Leu | Val | Lys | Leu | Gly | Val | Trp | Lys | Ser | Pro | |
| 315 | | | | | 320 | | | | | 325 | | | | | 330 | |
| ACC | GAC | ATG | CAA | TCC | TGG | GTC | CCC | CTA | TCA | ACG | GAT | GAT | CCA | GTG | ATA | 1058 |
| Thr | Asp | Met | Gln | Ser | Trp | Val | Pro | Leu | Ser | Thr | Asp | Asp | Pro | Val | Ile | |
| | | | | 335 | | | | | 340 | | | | | 345 | | |
| GAT | AGG | CTT | TAC | CTC | TCA | TCT | CAC | AGA | GGT | GTT | ATC | GCT | GAC | AAT | CAA | 1106 |
| Asp | Arg | Leu | Tyr | Leu | Ser | Ser | His | Arg | Gly | Val | Ile | Ala | Asp | Asn | Gln | |
| | | | 350 | | | | | 355 | | | | | 360 | | | |
| GCA | AAA | TGG | GCT | GTC | CCG | ACA | ACA | CGG | ACA | GAT | GAC | AAG | TTG | CGA | ATG | 1154 |
| Ala | Lys | Trp | Ala | Val | Pro | Thr | Thr | Arg | Thr | Asp | Asp | Lys | Leu | Arg | Met | |
| | | 365 | | | | | 370 | | | | | 375 | | | | |
| GAG | ACA | TGC | TTC | CAG | CAG | GCG | TGT | AAG | GGT | AAA | AAC | CAA | GCA | CTC | TGC | 1202 |

```
Glu  Thr  Cys  Phe  Gln  Gln  Ala  Cys  Lys  Gly  Lys  Asn  Gln  Ala  Leu  Cys
     380                      385                      390

GAG  AAT  CCC  GAG  TGG  GCA  CCA  TTG  AAG  GAT  AAC  AGG  ATT  CCT  TCA  TAC   1250
Glu  Asn  Pro  Glu  Trp  Ala  Pro  Leu  Lys  Asp  Asn  Arg  Ile  Pro  Ser  Tyr
395                      400                      405                      410

GGG  GTC  TTG  TCT  GTT  AAT  CTG  AGT  CTG  ACA  GTT  GAG  CTT  AAA  ATC  AAA   1298
Gly  Val  Leu  Ser  Val  Asn  Leu  Ser  Leu  Thr  Val  Glu  Leu  Lys  Ile  Lys
                    415                      420                      425

ATT  GCT  TCA  GGA  TTC  GGG  CCA  TTG  ATC  ACA  CAC  GGT  TCA  GGG  ATG  GAC   1346
Ile  Ala  Ser  Gly  Phe  Gly  Pro  Leu  Ile  Thr  His  Gly  Ser  Gly  Met  Asp
               430                      435                      440

CTA  TAC  AAA  ACC  AAC  CAC  AAC  AAT  GTG  TAT  TGG  CTG  ACT  ATC  CCG  CCA   1394
Leu  Tyr  Lys  Thr  Asn  His  Asn  Asn  Val  Tyr  Trp  Leu  Thr  Ile  Pro  Pro
          445                      450                      455

ATG  AAG  AAC  CTA  GCC  TTA  GGT  GTA  ATC  AAC  ACA  TTG  GAG  TGG  ATA  CCG   1442
Met  Lys  Asn  Leu  Ala  Leu  Gly  Val  Ile  Asn  Thr  Leu  Glu  Trp  Ile  Pro
     460                      465                      470

AGA  TTC  AAG  GTT  AGT  CCC  AAC  CTC  TTC  ACT  GTT  CCA  ATC  AAG  GAA  GCA   1490
Arg  Phe  Lys  Val  Ser  Pro  Asn  Leu  Phe  Thr  Val  Pro  Ile  Lys  Glu  Ala
475                      480                      485                      490

GGC  GAG  GAC  TGC  CAT  GCC  CCA  ACA  TAC  CTA  CCT  GCG  GAG  GTG  GAT  GGT   1538
Gly  Glu  Asp  Cys  His  Ala  Pro  Thr  Tyr  Leu  Pro  Ala  Glu  Val  Asp  Gly
                    495                      500                      505

GAT  GTC  AAA  CTC  AGT  TCC  AAT  CTG  GTA  ATT  CTA  CCT  GGT  CAG  GAT  CTC   1586
Asp  Val  Lys  Leu  Ser  Ser  Asn  Leu  Val  Ile  Leu  Pro  Gly  Gln  Asp  Leu
               510                      515                      520

CAA  TAT  GTT  TTG  GCA  ACC  TAC  GAT  ACT  TCC  AGG  GTT  GAA  CAT  GCT  GTG   1634
Gln  Tyr  Val  Leu  Ala  Thr  Tyr  Asp  Thr  Ser  Arg  Val  Glu  His  Ala  Val
          525                      530                      535

GTT  TAT  TAT  GTT  TAC  AGC  CCA  AGC  CGC  TCA  TTT  TCT  TAC  TTT  TAT  CCT   1682
Val  Tyr  Tyr  Val  Tyr  Ser  Pro  Ser  Arg  Ser  Phe  Ser  Tyr  Phe  Tyr  Pro
     540                      545                      550

TTT  AGG  TTG  CCT  ATA  AAG  GGG  GTC  CCA  ATC  GAA  TTA  CAA  GTG  GAA  TGC   1730
Phe  Arg  Leu  Pro  Ile  Lys  Gly  Val  Pro  Ile  Glu  Leu  Gln  Val  Glu  Cys
555                      560                      565                      570

TTC  ACA  TGG  GAC  CAA  AAA  CTC  TGG  TGC  CGT  CAC  TTC  TGT  GTG  CTT  GCG   1778
Phe  Thr  Trp  Asp  Gln  Lys  Leu  Trp  Cys  Arg  His  Phe  Cys  Val  Leu  Ala
                    575                      580                      585

GAT  TCA  GAA  TCT  GGT  GGA  CAT  ATC  ACT  CAC  TCT  GGG  ATG  GTG  GGC  ATG   1826
Asp  Ser  Glu  Ser  Gly  Gly  His  Ile  Thr  His  Ser  Gly  Met  Val  Gly  Met
               590                      595                      600

GGA  GTC  AGC  TGC  ACA  GTC  ACC  CGG  GAA  GAT  GGA  ACC  AAT  CGC  AGA         1871
Gly  Val  Ser  Cys  Thr  Val  Thr  Arg  Glu  Asp  Gly  Thr  Asn  Arg  Arg
               605                      610                      615

TAGGGCTGCT                                                                        1881

AGTGAACCAA  TCTCATGATG  TCACCCAGAC  ATCAGGCA                                      1919
```

( 2 ) INFORMATION FOR SEQ ID NO:6:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Ser  Pro  His  Arg  Asp  Arg  Ile  Asn  Ala  Phe  Tyr  Lys  Asp  Asn  Pro
1              5                        10                       15

His  Pro  Lys  Gly  Ser  Arg  Ile  Val  Ile  Asn  Arg  Glu  His  Leu  Met  Ile
               20                       25                       30
```

```
Asp Arg Pro Tyr Val Leu Leu Ala Val Leu Phe Val Met Phe Leu Ser
         35              40                  45
Leu Ile Gly Leu Leu Ala Ile Ala Gly Ile Arg Leu His Arg Ala Ala
         50                  55                  60
Ile Tyr Thr Ala Glu Ile His Lys Ser Leu Ser Thr Asn Leu Asp Val
 65              70                  75                      80
Thr Asn Ser Ile Glu His Gln Val Lys Asp Val Leu Thr Pro Leu Phe
                 85                  90                      95
Lys Ile Ile Gly Asp Glu Val Gly Leu Arg Thr Pro Gln Arg Phe Thr
             100             105                 110
Asp Leu Val Lys Phe Ile Ser Asp Lys Ile Lys Phe Leu Asn Pro Asp
         115             120                 125
Arg Glu Tyr Asp Phe Arg Asp Leu Thr Trp Cys Ile Asn Pro Pro Glu
     130             135                 140
Arg Ile Lys Leu Asp Tyr Asp Gln Tyr Cys Ala Asp Val Ala Ala Glu
145             150                 155                     160
Glu Leu Met Asn Ala Leu Val Asn Ser Thr Leu Leu Glu Ala Arg Ala
             165                 170                 175
Thr Asn Gln Phe Leu Ala Val Ser Lys Gly Asn Cys Ser Gly Pro Thr
             180                 185                 190
Thr Ile Arg Gly Gln Phe Ser Asn Met Ser Leu Ser Leu Leu Asp Leu
         195                 200                 205
Tyr Leu Ser Arg Gly Tyr Asn Val Ser Ser Ile Val Thr Met Thr Ser
     210                 215                 220
Gln Gly Met Tyr Gly Gly Thr Tyr Leu Val Gly Lys Pro Asn Leu Ser
225             230                 235                     240
Ser Lys Gly Ser Glu Leu Ser Gln Leu Ser Met His Arg Val Phe Glu
             245                 250                 255
Val Gly Val Ile Arg Asn Pro Gly Leu Gly Ala Pro Val Phe His Met
             260                 265                 270
Thr Asn Tyr Phe Glu Gln Pro Val Ser Asn Asp Phe Ser Asn Cys Met
         275                 280                 285
Val Ala Leu Gly Glu Leu Arg Phe Ala Ala Leu Cys His Arg Glu Asp
     290                 295                 300
Ser Val Thr Val Pro Tyr Gln Gly Ser Gly Lys Gly Val Ser Phe Gln
305                 310                 315                 320
Leu Val Lys Leu Gly Val Trp Lys Ser Pro Thr Asp Met Gln Ser Trp
             325                 330                 335
Val Pro Leu Ser Thr Asp Asp Pro Val Ile Asp Arg Leu Tyr Leu Ser
             340                 345                 350
Ser His Arg Gly Val Ile Ala Asp Asn Gln Ala Lys Trp Ala Val Pro
         355                 360                 365
Thr Thr Arg Thr Asp Asp Lys Leu Arg Met Glu Thr Cys Phe Gln Gln
         370                 375                 380
Ala Cys Lys Gly Lys Asn Gln Ala Leu Cys Glu Asn Pro Glu Trp Ala
385                 390                 395                 400
Pro Leu Lys Asp Asn Arg Ile Pro Ser Tyr Gly Val Leu Ser Val Asn
             405                 410                 415
Leu Ser Leu Thr Val Glu Leu Lys Ile Lys Ile Ala Ser Gly Phe Gly
         420                 425                 430
Pro Leu Ile Thr His Gly Ser Gly Met Asp Leu Tyr Lys Thr Asn His
         435                 440                 445
Asn Asn Val Tyr Trp Leu Thr Ile Pro Pro Met Lys Asn Leu Ala Leu
```

-continued 450 455 460

Gly Val Ile Asn Thr Leu Glu Trp Ile Pro Arg Phe Lys Val Ser Pro
465 470 475 480

Asn Leu Phe Thr Val Pro Ile Lys Glu Ala Gly Glu Asp Cys His Ala
485 490 495

Pro Thr Tyr Leu Pro Ala Glu Val Asp Gly Asp Val Lys Leu Ser Ser
500 505 510

Asn Leu Val Ile Leu Pro Gly Gln Asp Leu Gln Tyr Val Leu Ala Thr
515 520 525

Tyr Asp Thr Ser Arg Val Glu His Ala Val Val Tyr Tyr Val Tyr Ser
530 535 540

Pro Ser Arg Ser Phe Ser Tyr Phe Tyr Pro Phe Arg Leu Pro Ile Lys
545 550 555 560

Gly Val Pro Ile Glu Leu Gln Val Glu Cys Phe Thr Trp Asp Gln Lys
565 570 575

Leu Trp Cys Arg His Phe Cys Val Leu Ala Asp Ser Glu Ser Gly Gly
580 585 590

His Ile Thr His Ser Gly Met Val Gly Met Gly Val Ser Cys Thr Val
595 600 605

Thr Arg Glu Asp Gly Thr Asn Arg Arg
610 615

( 2 ) INFORMATION FOR SEQ ID NO:7:

( i ) SEQUENCE CHARACTERISTICS:
( A ) LENGTH: 1919 base pairs
( B ) TYPE: nucleic acid
( C ) STRANDEDNESS: double
( D ) TOPOLOGY: linear ( i i ) MOLECULE TYPE: DNA (genomic)

( v i ) ORIGINAL SOURCE:
( B ) STRAIN: Chicago 1 HA ( i x ) FEATURE:
( A ) NAME/KEY: CDS
( B ) LOCATION: 21..1874

( x i ) SEQUENCE DESCRIPTION: SEQ ID NO:7:

AGGGTGCAAG ATCATCCACA ATG TCA CCA CAC CGA GAC CGA ATA AAT GCC 50
Met Ser Pro His Arg Asp Arg Ile Asn Ala
1 5 10

TTC TAC AAA GAC AAC CCC CAT CCT AAG GGA AGT AGG ATA GTT ATT AAC 98
Phe Tyr Lys Asp Asn Pro His Pro Lys Gly Ser Arg Ile Val Ile Asn
15 20 25

AGA GAA CAT CTT ATG ATT GAT AGA CCT TAT GTT TTG CTG GCT GTT CTA 146
Arg Glu His Leu Met Ile Asp Arg Pro Tyr Val Leu Leu Ala Val Leu
30 35 40

TTC GTC ATG TTT CTG AGC TTG ATC GGG TTG CTA GCC ATT GCA GGC ATT 194
Phe Val Met Phe Leu Ser Leu Ile Gly Leu Leu Ala Ile Ala Gly Ile
45 50 55

AGA CTC CAT CGG GCA GCC ATC TAC ACC GCA GAG ATC CAT AAG AGC CTC 242
Arg Leu His Arg Ala Ala Ile Tyr Thr Ala Glu Ile His Lys Ser Leu
60 65 70

AGC ACC AAT CTA GAT GTA ACT AAC TCA ATC GAG CAT CAG GTC AAG GAC 290
Ser Thr Asn Leu Asp Val Thr Asn Ser Ile Glu His Gln Val Lys Asp
75 80 85 90

GTG CTG ACA CCA CTC TTC AAG ATC ATC GGT GAT GAA GTG GGC CTG AGG 338
Val Leu Thr Pro Leu Phe Lys Ile Ile Gly Asp Glu Val Gly Leu Arg
95 100 105

| | | | | | | | | | | | | | | | | |
|---|---|---|---|---|---|---|---|---|---|---|---|---|---|---|---|---|
| ACA | CCT | CAG | AGA | TTC | ACT | GAC | CTA | GTG | AAA | TTC | ATC | TCT | GAC | AAA | ATT | 386 |
| Thr | Pro | Gln | Arg | Phe | Thr | Asp | Leu | Val | Lys | Phe | Ile | Ser | Asp | Lys | Ile | |
| | | 110 | | | | | 115 | | | | | 120 | | | | |
| AAA | TTC | CTT | AAT | CCG | GAT | AGG | GAG | TAC | GAC | TTC | AGA | GAT | CTC | ACT | TGG | 434 |
| Lys | Phe | Leu | Asn | Pro | Asp | Arg | Glu | Tyr | Asp | Phe | Arg | Asp | Leu | Thr | Trp | |
| | | 125 | | | | 130 | | | | | 135 | | | | | |
| TGT | ATC | AAC | CCG | CCA | GAG | AGA | ATC | AAA | TTG | GAT | TAT | GAT | CAA | TAC | TGT | 482 |
| Cys | Ile | Asn | Pro | Pro | Glu | Arg | Ile | Lys | Leu | Asp | Tyr | Asp | Gln | Tyr | Cys | |
| | 140 | | | | | 145 | | | | 150 | | | | | | |
| GCA | GAT | GTG | GCT | GCT | GAA | GAA | CTC | ATG | AAT | GCA | TTG | GTG | AAC | TCA | ACT | 530 |
| Ala | Asp | Val | Ala | Ala | Glu | Glu | Leu | Met | Asn | Ala | Leu | Val | Asn | Ser | Thr | |
| 155 | | | | | 160 | | | | | 165 | | | | | 170 | |
| CTA | CTG | GAG | GCC | AGG | GCA | ACC | AAT | CAG | TTC | CTA | GCT | GTC | TCA | AAG | GGA | 578 |
| Leu | Leu | Glu | Ala | Arg | Ala | Thr | Asn | Gln | Phe | Leu | Ala | Val | Ser | Lys | Gly | |
| | | | | 175 | | | | | 180 | | | | | 185 | | |
| AAC | TGC | TCA | GGG | CCC | ACT | ACA | ATC | AGA | GGT | CAA | TTC | TCA | AAC | ATG | TCG | 626 |
| Asn | Cys | Ser | Gly | Pro | Thr | Thr | Ile | Arg | Gly | Gln | Phe | Ser | Asn | Met | Ser | |
| | | | 190 | | | | | 195 | | | | | 200 | | | |
| CTG | TCC | CTG | TTG | GAC | TTG | TAT | TTA | AGT | CGA | GGT | TAC | AAT | GTG | TCA | TCT | 674 |
| Leu | Ser | Leu | Leu | Asp | Leu | Tyr | Leu | Ser | Arg | Gly | Tyr | Asn | Val | Ser | Ser | |
| | | 205 | | | | | 210 | | | | | 215 | | | | |
| ATA | GTC | ACC | ATG | ACA | TCC | CAG | GGA | ATG | TAC | GGG | GGA | ACT | TAC | CTA | GTG | 722 |
| Ile | Val | Thr | Met | Thr | Ser | Gln | Gly | Met | Tyr | Gly | Gly | Thr | Tyr | Leu | Val | |
| | 220 | | | | | 225 | | | | | 230 | | | | | |
| GGA | AAG | CCT | AAT | CTG | AGC | AGT | AAA | GGG | TCA | GAG | TTG | TCA | CAA | CTG | AGC | 770 |
| Gly | Lys | Pro | Asn | Leu | Ser | Ser | Lys | Gly | Ser | Glu | Leu | Ser | Gln | Leu | Ser | |
| 235 | | | | | 240 | | | | | 245 | | | | | 250 | |
| ATG | CAC | CGA | GTG | TTT | GAA | GTA | GGG | GTT | ATC | AGA | AAT | CCG | GGT | TTG | GGG | 818 |
| Met | His | Arg | Val | Phe | Glu | Val | Gly | Val | Ile | Arg | Asn | Pro | Gly | Leu | Gly | |
| | | | | 255 | | | | | 260 | | | | | 265 | | |
| GCT | CCG | GTG | TTC | CAT | ATG | ACA | AAC | TAT | TTT | GAG | CAA | CCA | GTC | AGT | AAT | 866 |
| Ala | Pro | Val | Phe | His | Met | Thr | Asn | Tyr | Phe | Glu | Gln | Pro | Val | Ser | Asn | |
| | | | | 270 | | | | | 275 | | | | | 280 | | |
| GAT | TTC | AGC | AAC | TGC | ATG | GTG | GCT | TTG | GGG | GAG | CTC | AGG | TTC | GCA | GCC | 914 |
| Asp | Phe | Ser | Asn | Cys | Met | Val | Ala | Leu | Gly | Glu | Leu | Arg | Phe | Ala | Ala | |
| | | 285 | | | | | 290 | | | | | 295 | | | | |
| CTC | TGT | CAC | AGA | GAA | GAT | TCT | GTC | ACG | GTT | CCC | TAT | CAG | GGG | TCA | GGG | 962 |
| Leu | Cys | His | Arg | Glu | Asp | Ser | Val | Thr | Val | Pro | Tyr | Gln | Gly | Ser | Gly | |
| | | 300 | | | | | 305 | | | | | 310 | | | | |
| AAA | GGT | GTC | AGC | TTC | CAG | CTC | GTC | AAG | CTA | GGT | GTC | TGG | AAA | TCC | CCA | 1010 |
| Lys | Gly | Val | Ser | Phe | Gln | Leu | Val | Lys | Leu | Gly | Val | Trp | Lys | Ser | Pro | |
| 315 | | | | | 320 | | | | | 325 | | | | | 330 | |
| ACC | GAC | ATG | CAA | TCC | TGG | GTC | CCC | CTA | TCA | ACG | GAT | GAT | CCA | GTG | ATA | 1058 |
| Thr | Asp | Met | Gln | Ser | Trp | Val | Pro | Leu | Ser | Thr | Asp | Asp | Pro | Val | Ile | |
| | | | | 335 | | | | | 340 | | | | | 345 | | |
| GAT | AGG | CTT | TAC | CTC | TCA | TCT | CAC | AGA | GGT | GTT | ATC | GCT | GAC | AAT | CAA | 1106 |
| Asp | Arg | Leu | Tyr | Leu | Ser | Ser | His | Arg | Gly | Val | Ile | Ala | Asp | Asn | Gln | |
| | | | 350 | | | | | 355 | | | | | 360 | | | |
| GCA | AAA | TGG | GCT | GTC | CCG | ACA | ACA | CGG | ACA | GAT | GAC | AAG | TTG | CGA | ATG | 1154 |
| Ala | Lys | Trp | Ala | Val | Pro | Thr | Thr | Arg | Thr | Asp | Asp | Lys | Leu | Arg | Met | |
| | | 365 | | | | | 370 | | | | | 375 | | | | |
| GAG | ACA | TGC | TTC | CAG | CAG | GCG | TGT | AAG | GGT | AAA | AAC | CAA | GCA | CTC | TGC | 1202 |
| Glu | Thr | Cys | Phe | Gln | Gln | Ala | Cys | Lys | Gly | Lys | Asn | Gln | Ala | Leu | Cys | |
| | 380 | | | | | 385 | | | | | 390 | | | | | |
| GAG | AAT | CCC | GAG | TGG | GCA | CCA | TTG | AAG | GAT | AAC | AGG | ATT | CCT | TCA | TAC | 1250 |
| Glu | Asn | Pro | Glu | Trp | Ala | Pro | Leu | Lys | Asp | Asn | Arg | Ile | Pro | Ser | Tyr | |
| 395 | | | | 400 | | | | | 405 | | | | | 410 | | |
| GGG | GTC | TTG | TCT | GTT | AAT | CTG | AGT | CTG | ACA | GTT | GAG | CTT | AAA | ATC | AAA | 1298 |
| Gly | Val | Leu | Ser | Val | Asn | Leu | Ser | Leu | Thr | Val | Glu | Leu | Lys | Ile | Lys | |
| | | | | 415 | | | | | 420 | | | | | 425 | | |

| | | | | | | | | | | | | | | | | |
|---|---|---|---|---|---|---|---|---|---|---|---|---|---|---|---|---|
| ATT | GCT | TCA | GGA | TTC | GGG | CCA | TTG | ATC | ACA | CAC | GGT | TCA | GGG | ATG | GAC | 1346 |
| Ile | Ala | Ser | Gly | Phe | Gly | Pro | Leu | Ile | Thr | His | Gly | Ser | Gly | Met | Asp | |
| | | 430 | | | | | 435 | | | | | 440 | | | | |
| CTA | TAC | AAA | ACC | AAC | CAC | AAC | AAT | GTG | TAT | TGG | CTG | ACT | ATC | CCG | CCA | 1394 |
| Leu | Tyr | Lys | Thr | Asn | His | Asn | Asn | Val | Tyr | Trp | Leu | Thr | Ile | Pro | Pro | |
| | | 445 | | | | | 450 | | | | | 455 | | | | |
| ATG | AAG | AAC | CTA | GCC | TTA | GGT | GTA | ATC | AAC | ACA | TTG | GAG | TGG | ATA | CCG | 1442 |
| Met | Lys | Asn | Leu | Ala | Leu | Gly | Val | Ile | Asn | Thr | Leu | Glu | Trp | Ile | Pro | |
| | 460 | | | | | 465 | | | | | 470 | | | | | |
| AGA | TTC | AAG | GTT | AGT | CCC | AAC | CTC | TTC | ACT | GTT | CCA | ATC | AAG | GAA | GCA | 1490 |
| Arg | Phe | Lys | Val | Ser | Pro | Asn | Leu | Phe | Thr | Val | Pro | Ile | Lys | Glu | Ala | |
| 475 | | | | | 480 | | | | | 485 | | | | | 490 | |
| GGC | GAG | GAC | TGC | CAT | GCC | CCA | ACA | TAC | CTA | CCT | GCG | GAG | GTG | GAT | GGT | 1538 |
| Gly | Glu | Asp | Cys | His | Ala | Pro | Thr | Tyr | Leu | Pro | Ala | Glu | Val | Asp | Gly | |
| | | | | 495 | | | | | 500 | | | | | 505 | | |
| GAT | GTC | AAA | CTC | AGT | TCC | AAT | CTG | GTA | ATT | CTA | CCT | GGT | CAG | GAT | CTC | 1586 |
| Asp | Val | Lys | Leu | Ser | Ser | Asn | Leu | Val | Ile | Leu | Pro | Gly | Gln | Asp | Leu | |
| | | | 510 | | | | | 515 | | | | | 520 | | | |
| CAA | TAT | GTT | TTG | GCA | ACC | TAC | GAT | ACT | TCC | AGG | GTT | GAA | CAT | GCT | GTG | 1634 |
| Gln | Tyr | Val | Leu | Ala | Thr | Tyr | Asp | Thr | Ser | Arg | Val | Glu | His | Ala | Val | |
| | | 525 | | | | | 530 | | | | | 535 | | | | |
| GTT | TAT | TAT | GTT | TAC | AGC | CCA | GGC | CGC | TCA | TTT | TCT | TAC | TTT | TAT | CCT | 1682 |
| Val | Tyr | Tyr | Val | Tyr | Ser | Pro | Gly | Arg | Ser | Phe | Ser | Tyr | Phe | Tyr | Pro | |
| | 540 | | | | | 545 | | | | | 550 | | | | | |
| TTT | AGG | TTG | CCT | ATA | AAG | GGG | GTC | CCA | ATC | GAA | TTA | CAA | GTG | GAA | TGC | 1730 |
| Phe | Arg | Leu | Pro | Ile | Lys | Gly | Val | Pro | Ile | Glu | Leu | Gln | Val | Glu | Cys | |
| 555 | | | | | 560 | | | | | 565 | | | | | 570 | |
| TTC | ACA | TGG | GAC | CAA | AAA | CTC | TGG | TGC | CGT | CAC | TTC | TGT | GTG | CTT | GCG | 1778 |
| Phe | Thr | Trp | Asp | Gln | Lys | Leu | Trp | Cys | Arg | His | Phe | Cys | Val | Leu | Ala | |
| | | | | 575 | | | | | 580 | | | | | 585 | | |
| GAT | TCA | GAA | TCT | GGT | GGA | CAT | ATC | ACT | CAC | TCT | GGG | ATG | GTG | GGC | ATG | 1826 |
| Asp | Ser | Glu | Ser | Gly | Gly | His | Ile | Thr | His | Ser | Gly | Met | Val | Gly | Met | |
| | | | 590 | | | | | 595 | | | | | 600 | | | |
| GGA | GTC | AGC | TGC | ACA | GTC | ACC | CGG | GAA | GAT | GGA | ACC | AAT | CGC | AGA | | 1871 |
| Gly | Val | Ser | Cys | Thr | Val | Thr | Arg | Glu | Asp | Gly | Thr | Asn | Arg | Arg | | |
| | | 605 | | | | | 610 | | | | | 615 | | | | |

TAGGGCTGCT                                                                 1881

AGTGAACCAA TCTCATGATG TCACCCAGAC ATCAGGCA                                  1919

( 2 ) INFORMATION FOR SEQ ID NO:8:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Ser | Pro | His | Arg | Asp | Arg | Ile | Asn | Ala | Phe | Tyr | Lys | Asp | Asn | Pro |
| 1 | | | | 5 | | | | | 10 | | | | | 15 | |
| His | Pro | Lys | Gly | Ser | Arg | Ile | Val | Ile | Asn | Arg | Glu | His | Leu | Met | Ile |
| | | | 20 | | | | | 25 | | | | | 30 | | |
| Asp | Arg | Pro | Tyr | Val | Leu | Leu | Ala | Val | Leu | Phe | Val | Met | Phe | Leu | Ser |
| | | 35 | | | | | 40 | | | | | 45 | | | |
| Leu | Ile | Gly | Leu | Leu | Ala | Ile | Ala | Gly | Ile | Arg | Leu | His | Arg | Ala | Ala |
| | 50 | | | | | 55 | | | | | 60 | | | | |
| Ile | Tyr | Thr | Ala | Glu | Ile | His | Lys | Ser | Leu | Ser | Thr | Asn | Leu | Asp | Val |
| 65 | | | | | 70 | | | | | 75 | | | | | 80 |
| Thr | Asn | Ser | Ile | Glu | His | Gln | Val | Lys | Asp | Val | Leu | Thr | Pro | Leu | Phe |

-continued

|     |     |     |     |     | 85  |     |     |     | 90  |     |     |     | 95  |     |
| --- | --- | --- | --- | --- | --- | --- | --- | --- | --- | --- | --- | --- | --- | --- |

Lys Ile Ile Gly Asp Glu Val Gly Leu Arg Thr Pro Gln Arg Phe Thr
                100                     105                     110

Asp Leu Val Lys Phe Ile Ser Asp Lys Ile Lys Phe Leu Asn Pro Asp
            115                     120                     125

Arg Glu Tyr Asp Phe Arg Asp Leu Thr Trp Cys Ile Asn Pro Pro Glu
    130                     135                     140

Arg Ile Lys Leu Asp Tyr Asp Gln Tyr Cys Ala Asp Val Ala Ala Glu
145                     150                     155                 160

Glu Leu Met Asn Ala Leu Val Asn Ser Thr Leu Leu Glu Ala Arg Ala
                165                     170                     175

Thr Asn Gln Phe Leu Ala Val Ser Lys Gly Asn Cys Ser Gly Pro Thr
            180                     185                     190

Thr Ile Arg Gly Gln Phe Ser Asn Met Ser Leu Ser Leu Leu Asp Leu
        195                     200                     205

Tyr Leu Ser Arg Gly Tyr Asn Val Ser Ser Ile Val Thr Met Thr Ser
    210                     215                     220

Gln Gly Met Tyr Gly Gly Thr Tyr Leu Val Gly Lys Pro Asn Leu Ser
225                     230                     235                 240

Ser Lys Gly Ser Glu Leu Ser Gln Leu Ser Met His Arg Val Phe Glu
                245                     250                     255

Val Gly Val Ile Arg Asn Pro Gly Leu Gly Ala Pro Val Phe His Met
            260                     265                     270

Thr Asn Tyr Phe Glu Gln Pro Val Ser Asn Asp Phe Ser Asn Cys Met
        275                     280                     285

Val Ala Leu Gly Glu Leu Arg Phe Ala Ala Leu Cys His Arg Glu Asp
    290                     295                     300

Ser Val Thr Val Pro Tyr Gln Gly Ser Gly Lys Gly Val Ser Phe Gln
305                     310                     315                 320

Leu Val Lys Leu Gly Val Trp Lys Ser Pro Thr Asp Met Gln Ser Trp
                325                     330                     335

Val Pro Leu Ser Thr Asp Asp Pro Val Ile Asp Arg Leu Tyr Leu Ser
            340                     345                     350

Ser His Arg Gly Val Ile Ala Asp Asn Gln Ala Lys Trp Ala Val Pro
        355                     360                     365

Thr Thr Arg Thr Asp Asp Lys Leu Arg Met Glu Thr Cys Phe Gln Gln
    370                     375                     380

Ala Cys Lys Gly Lys Asn Gln Ala Leu Cys Glu Asn Pro Glu Trp Ala
385                     390                     395                 400

Pro Leu Lys Asp Asn Arg Ile Pro Ser Tyr Gly Val Leu Ser Val Asn
                405                     410                     415

Leu Ser Leu Thr Val Glu Leu Lys Ile Lys Ile Ala Ser Gly Phe Gly
            420                     425                     430

Pro Leu Ile Thr His Gly Ser Gly Met Asp Leu Tyr Lys Thr Asn His
        435                     440                     445

Asn Asn Val Tyr Trp Leu Thr Ile Pro Pro Met Lys Asn Leu Ala Leu
    450                     455                     460

Gly Val Ile Asn Thr Leu Glu Trp Ile Pro Arg Phe Lys Val Ser Pro
465                     470                     475                 480

Asn Leu Phe Thr Val Pro Ile Lys Glu Ala Gly Glu Asp Cys His Ala
                485                     490                     495

Pro Thr Tyr Leu Pro Ala Glu Val Asp Gly Asp Val Lys Leu Ser Ser
            500                     505                     510

| | | | | | | | | | | | | | |
|---|---|---|---|---|---|---|---|---|---|---|---|---|---|
| Asn | Leu | Val 515 | Ile | Leu | Pro | Gly | Gln 520 | Asp | Leu | Gln | Tyr | Val 525 | Leu | Ala | Thr |
| Tyr | Asp 530 | Thr | Ser | Arg | Val | Glu 535 | His | Ala | Val | Val | Tyr 540 | Val | Tyr | Ser |
| Pro 545 | Gly | Arg | Ser | Phe | Ser 550 | Tyr | Phe | Tyr | Pro | Phe 555 | Arg | Leu | Pro | Ile | Lys 560 |
| Gly | Val | Pro | Ile | Glu 565 | Leu | Gln | Val | Glu | Cys 570 | Phe | Thr | Trp | Asp | Gln 575 | Lys |
| Leu | Trp | Cys | Arg 580 | His | Phe | Cys | Val | Leu 585 | Ala | Asp | Ser | Glu | Ser 590 | Gly | Gly |
| His | Ile | Thr 595 | His | Ser | Gly | Met | Val 600 | Gly | Met | Gly | Val | Ser 605 | Cys | Thr | Val |
| Thr | Arg | Glu 610 | Asp | Gly | Thr | Asn 615 | Arg | Arg |

( 2 ) INFORMATION FOR SEQ ID NO:9:

( i ) SEQUENCE CHARACTERISTICS:
        ( A ) LENGTH: 1919 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: Chicago 2 HA ( i x ) FEATURE:
        ( A ) NAME/KEY: CDS
        ( B ) LOCATION: 21..1874

( x i ) SEQUENCE DESCRIPTION: SEQ ID NO:9:

```
AGGGTGCAAG ATCATCCACA ATG TCA CCA CAA CGA GAC CGA ATA AAT GCC           50
                      Met Ser Pro Gln Arg Asp Arg Ile Asn Ala
                        1               5                  10

TTC TAC AAA GAC AAC CCC CAT CCT AAG GGA AGT AGG ATA GTT ATT AAC          98
Phe Tyr Lys Asp Asn Pro His Pro Lys Gly Ser Arg Ile Val Ile Asn
                15                  20                  25

AGA GAA CAT CTT ATG ATT GAT AGA CCT TAT GTT TTG CTG GCT GTT CTA         146
Arg Glu His Leu Met Ile Asp Arg Pro Tyr Val Leu Leu Ala Val Leu
         30                  35                  40

TTC GTC ATG TTT CTG AGC TTG ATC GGG TTG CTA GCC ATT GCA GGC ATT         194
Phe Val Met Phe Leu Ser Leu Ile Gly Leu Leu Ala Ile Ala Gly Ile
             45                  50                  55

AGA CTT CAT CGG GCA GCC ATC TAC ACC GCA GAG ATC CAT AAA AGC CTC         242
Arg Leu His Arg Ala Ala Ile Tyr Thr Ala Glu Ile His Lys Ser Leu
         60                  65                  70

AGC ACC AAT CTA GAT GTA ACT AAC TCA ATC GAG CAT CAG GTC AAG GAC         290
Ser Thr Asn Leu Asp Val Thr Asn Ser Ile Glu His Gln Val Lys Asp
 75                  80                  85                  90

GTG CTG ACA CCA CTC TTC AAG ATC ATC GGT GAT GAA GTG GGC CTG AGG         338
Val Leu Thr Pro Leu Phe Lys Ile Ile Gly Asp Glu Val Gly Leu Arg
                 95                  100                 105

ACA CCT CAG AGA TTC ACT GAC CTA GTG AAA TTC ATC TCT GAC AAG ATT         386
Thr Pro Gln Arg Phe Thr Asp Leu Val Lys Phe Ile Ser Asp Lys Ile
             110                 115                 120

AAA TTC CTT AAT CCG GAT AGG GAG TAC GAC TTC AGA GAC CTC ACT TGG         434
Lys Phe Leu Asn Pro Asp Arg Glu Tyr Asp Phe Arg Asp Leu Thr Trp
         125                 130                 135

TGC ATC AAC CCG CCA GAG AGA ATC AAA TTG GAT TAT GAT CAA TAC TGT         482
Cys Ile Asn Pro Pro Glu Arg Ile Lys Leu Asp Tyr Asp Gln Tyr Cys
 140                 145                 150
```

| | | | | | | | | | | | | | | | |
|---|---|---|---|---|---|---|---|---|---|---|---|---|---|---|---|
| GCA | GAT | GTG | GCT | GCT | GAA | GAA | CTC | ATG | AAT | GCA | TTG | GTG | AAC | TCA | ACT | 530
| Ala | Asp | Val | Ala | Ala | Glu | Glu | Leu | Met | Asn | Ala | Leu | Val | Asn | Ser | Thr |
| 155 | | | | 160 | | | | | 165 | | | | | 170 | |
| CTA | CTG | GAG | GCC | AGG | ACA | ACC | AAT | CAG | TTC | CTA | GCT | GTC | TCA | AAG | GGA | 578
| Leu | Leu | Glu | Ala | Arg | Thr | Thr | Asn | Gln | Phe | Leu | Ala | Val | Ser | Lys | Gly |
| | | | | 175 | | | | | 180 | | | | | 185 | |
| AAC | TGC | TCA | GGG | CCC | ACT | ACA | ATC | AGA | GGT | CAA | TTC | TCA | AAC | ATG | TCG | 626
| Asn | Cys | Ser | Gly | Pro | Thr | Thr | Ile | Arg | Gly | Gln | Phe | Ser | Asn | Met | Ser |
| | | | 190 | | | | | 195 | | | | | 200 | | |
| CTG | TCC | CTG | TTG | GAC | TTG | TAT | TTA | AGT | CGA | GGT | TAC | AAT | GTA | TCA | TCT | 674
| Leu | Ser | Leu | Leu | Asp | Leu | Tyr | Leu | Ser | Arg | Gly | Tyr | Asn | Val | Ser | Ser |
| | | | 205 | | | | 210 | | | | | 215 | | | |
| ATA | GTC | ACT | ATG | ACA | TCC | CAG | GGA | ATG | TAC | GGG | GGA | ACT | TAC | CTA | GTG | 722
| Ile | Val | Thr | Met | Thr | Ser | Gln | Gly | Met | Tyr | Gly | Gly | Thr | Tyr | Leu | Val |
| | | 220 | | | | 225 | | | | | 230 | | | | |
| GAA | AAA | CCT | AAT | CTG | AGC | AGT | AAA | GGG | TCA | GAG | TTG | TCA | CAA | CTG | AGC | 770
| Glu | Lys | Pro | Asn | Leu | Ser | Ser | Lys | Gly | Ser | Glu | Leu | Ser | Gln | Leu | Ser |
| 235 | | | | | 240 | | | | | 245 | | | | | 250 |
| ATG | CAT | CGA | GTG | TTT | GAA | GTA | GGT | GTT | ATC | AGA | AAT | CCG | GGT | TTG | GGG | 818
| Met | His | Arg | Val | Phe | Glu | Val | Gly | Val | Ile | Arg | Asn | Pro | Gly | Leu | Gly |
| | | | | 255 | | | | | 260 | | | | | 265 | |
| GCT | CCG | GTG | TTC | CAT | ATG | ACA | AAC | TAT | TTT | GAG | CAA | CCA | GTC | AGT | AAT | 866
| Ala | Pro | Val | Phe | His | Met | Thr | Asn | Tyr | Phe | Glu | Gln | Pro | Val | Ser | Asn |
| | | | 270 | | | | | 275 | | | | | 280 | | |
| GAT | TTC | AGC | AAC | TGC | ATG | GTG | GCT | TTG | GGG | GAG | CTC | AAA | TTC | GCA | GCC | 914
| Asp | Phe | Ser | Asn | Cys | Met | Val | Ala | Leu | Gly | Glu | Leu | Lys | Phe | Ala | Ala |
| | | 285 | | | | | 290 | | | | | 295 | | | |
| CTC | TGT | CAC | AGG | GAA | GAT | TTT | ATC | ACA | ATT | CCC | TAT | CAG | GGG | TCA | GGG | 962
| Leu | Cys | His | Arg | Glu | Asp | Phe | Ile | Thr | Ile | Pro | Tyr | Gln | Gly | Ser | Gly |
| | 300 | | | | | 305 | | | | | 310 | | | | |
| AAA | GGT | GTC | AGC | TTC | CGG | CTC | GTC | AAG | CTA | GGT | GTC | TGG | AAA | TCT | CCA | 1010
| Lys | Gly | Val | Ser | Phe | Arg | Leu | Val | Lys | Leu | Gly | Val | Trp | Lys | Ser | Pro |
| 315 | | | | | 320 | | | | | 325 | | | | | 330 |
| ACC | GAC | ATG | CAA | TCC | TGG | GTC | CCC | CTA | TCA | ACG | GAT | GAT | CCA | GTG | ATA | 1058
| Thr | Asp | Met | Gln | Ser | Trp | Val | Pro | Leu | Ser | Thr | Asp | Asp | Pro | Val | Ile |
| | | | | 335 | | | | | 340 | | | | | 345 | |
| GAT | AAG | CTT | TAC | CTC | TCA | TCT | CAC | AGG | GGT | GTT | ATC | GCT | GAC | AAT | CAA | 1106
| Asp | Lys | Leu | Tyr | Leu | Ser | Ser | His | Arg | Gly | Val | Ile | Ala | Asp | Asn | Gln |
| | | | 350 | | | | | 355 | | | | | 360 | | |
| GCA | AAA | TGG | GCT | GTC | CCG | ACA | ACA | CGG | ACA | GAT | GAC | AAG | TTG | CGA | ATG | 1154
| Ala | Lys | Trp | Ala | Val | Pro | Thr | Thr | Arg | Thr | Asp | Asp | Lys | Leu | Arg | Met |
| | | 365 | | | | | 370 | | | | | 375 | | | |
| GAG | ACA | TGC | TTC | CAG | CAG | GCG | TGT | AAG | GGT | AGA | ATC | CAA | GCA | CTC | TGC | 1202
| Glu | Thr | Cys | Phe | Gln | Gln | Ala | Cys | Lys | Gly | Arg | Ile | Gln | Ala | Leu | Cys |
| | 380 | | | | | 385 | | | | | 390 | | | | |
| GAG | AAT | CCC | GAG | TGG | GCA | CCA | TTG | AAG | GAT | AAC | AGG | ATT | CCT | TCA | TAC | 1250
| Glu | Asn | Pro | Glu | Trp | Ala | Pro | Leu | Lys | Asp | Asn | Arg | Ile | Pro | Ser | Tyr |
| 395 | | | | 400 | | | | | 405 | | | | | 410 | |
| GGG | GTC | TTG | TCT | GTT | AAT | CTG | AGT | CTG | ACA | GTT | GAG | CTT | AAA | ATC | AAA | 1298
| Gly | Val | Leu | Ser | Val | Asn | Leu | Ser | Leu | Thr | Val | Glu | Leu | Lys | Ile | Lys |
| | | | | 415 | | | | | 420 | | | | | 425 | |
| ATT | GCT | TCA | GGA | TTC | GGG | CCA | TTG | ATC | ACA | CAC | GGT | TCA | GGG | ATG | GAC | 1346
| Ile | Ala | Ser | Gly | Phe | Gly | Pro | Leu | Ile | Thr | His | Gly | Ser | Gly | Met | Asp |
| | | | 430 | | | | | 435 | | | | | 440 | | |
| CTA | TAC | AAA | TCC | AAC | CAC | AAC | AAT | GTG | TAT | TGG | CTG | ACT | ATC | CCG | CCA | 1394
| Leu | Tyr | Lys | Ser | Asn | His | Asn | Asn | Val | Tyr | Trp | Leu | Thr | Ile | Pro | Pro |
| | | | 445 | | | | | 450 | | | | | 455 | | |
| ATG | AAG | AAC | CTA | GCC | TTA | GGT | GTA | ATC | AAC | ACA | TTG | GAG | TGG | ATA | CCG | 1442
| Met | Lys | Asn | Leu | Ala | Leu | Gly | Val | Ile | Asn | Thr | Leu | Glu | Trp | Ile | Pro |
| 460 | | | | | 465 | | | | | 470 | | | | | |

| | | | | | | | | | | | | | | | | |
|---|---|---|---|---|---|---|---|---|---|---|---|---|---|---|---|---|
| AGA | TTC | AAG | GTT | AGT | CCC | AAC | CTC | TTC | ACT | ATT | CCA | ATC | AAG | GAA | GCA | 1490 |
| Arg 475 | Phe | Lys | Val | Ser | Pro 480 | Asn | Leu | Phe | Thr | Ile 485 | Pro | Ile | Lys | Glu | Ala 490 | |
| GGC | GAG | GAC | TGC | CAT | GCC | CCA | ACA | TAC | CTC | TCT | GCG | GAG | GTG | GAT | GGT | 1538 |
| Gly | Glu | Asp | Cys | His 495 | Ala | Pro | Thr | Tyr | Leu 500 | Ser | Ala | Glu | Val | Asp 505 | Gly | |
| GAT | GTC | AAA | CTC | AGT | TCC | AAT | CTG | GTA | ATT | CTA | CCT | GGC | CAA | GAT | CTC | 1586 |
| Asp | Val | Lys | Leu 510 | Ser | Ser | Asn | Leu | Val 515 | Ile | Leu | Pro | Gly | Gln 520 | Asp | Leu | |
| CAA | TAT | GTT | TTG | GCA | ACC | TAC | GAT | ACT | TCC | AGG | GTT | GAA | CAT | GCT | GTG | 1634 |
| Gln | Tyr | Val 525 | Leu | Ala | Thr | Tyr | Asp 530 | Thr | Ser | Arg | Val | Glu 535 | His | Ala | Val | |
| GTT | TAT | TAT | GTT | TAC | AAC | CCA | AGC | CGC | TCA | TTT | TCT | TAC | TTT | TAT | CCT | 1682 |
| Val | Tyr 540 | Tyr | Val | Tyr | Asn | Pro 545 | Ser | Arg | Ser | Phe | Ser 550 | Tyr | Phe | Tyr | Pro | |
| TTT | AGG | TTG | CCT | GTA | AAG | GGG | TTC | CCC | ATC | GAA | TTA | CAA | GTG | GAA | TGC | 1730 |
| Phe 555 | Arg | Leu | Pro | Val | Lys 560 | Gly | Phe | Pro | Ile | Glu 565 | Leu | Gln | Val | Glu | Cys 570 | |
| TTC | ACA | TGG | GAC | CAA | AAA | CTC | TGG | TGC | CGT | CAC | TTC | TGT | GTG | CTT | GCG | 1778 |
| Phe | Thr | Trp | Asp | Gln 575 | Lys | Leu | Trp | Cys | Arg 580 | His | Phe | Cys | Val | Leu 585 | Ala | |
| GAC | TCA | GAA | TCT | GGT | GGA | CAT | ATC | ACT | CAC | TCT | GGG | ATG | GTG | GGC | ATG | 1826 |
| Asp | Ser | Glu | Ser 590 | Gly | Gly | His | Ile | Thr 595 | His | Ser | Gly | Met | Val 600 | Gly | Met | |
| GGA | GTC | AGC | TGC | ACA | GTC | ACC | CGG | GAA | GAT | GGA | ACC | AAT | CGC | AGA | | 1871 |
| Gly | Val | Ser 605 | Cys | Thr | Val | Thr | Arg 610 | Glu | Asp | Gly | Thr | Asn 615 | Arg | Arg | | |
| TAGGGCTGCT | | | | | | | | | | | | | | | | 1881 |
| AGTGAACCAA | TCTCATGATG | TCACCCAGAC | ATCAGGCA | | | | | | | | | | | | | 1919 |

(2) INFORMATION FOR SEQ ID NO:10:

(i) SEQUENCE CHARACTERISTICS:
        (A) LENGTH: 617 amino acids
        (B) TYPE: amino acid
        (D) TOPOLOGY: linear (ii) MOLECULE TYPE: protein (xi) SEQUENCE DESCRIPTION: SEQ ID NO:10:

| | | | | | | | | | | | | | | |
|---|---|---|---|---|---|---|---|---|---|---|---|---|---|---|
| Met 1 | Ser | Pro | Gln | Arg 5 | Asp | Arg | Ile | Asn | Ala 10 | Phe | Tyr | Lys | Asp | Asn Pro 15 |
| His | Pro | Lys | Gly 20 | Ser | Arg | Ile | Val | Ile 25 | Asn | Arg | Glu | His | Leu 30 | Met Ile |
| Asp | Arg | Pro 35 | Tyr | Val | Leu | Leu | Ala 40 | Val | Leu | Phe | Val | Met 45 | Phe | Leu Ser |
| Leu | Ile 50 | Gly | Leu | Leu | Ala | Ile 55 | Ala | Gly | Ile | Arg | Leu 60 | His | Arg | Ala Ala |
| Ile 65 | Tyr | Thr | Ala | Glu | Ile 70 | His | Lys | Ser | Leu | Ser 75 | Thr | Asn | Leu | Asp Val 80 |
| Thr | Asn | Ser | Ile | Glu 85 | His | Gln | Val | Lys | Asp 90 | Val | Leu | Thr | Pro | Leu Phe 95 |
| Lys | Ile | Ile | Gly 100 | Asp | Glu | Val | Gly | Leu 105 | Arg | Thr | Pro | Gln | Arg 110 | Phe Thr |
| Asp | Leu | Val 115 | Lys | Phe | Ile | Ser | Asp 120 | Lys | Ile | Lys | Phe | Leu 125 | Asn | Pro Asp |
| Arg | Glu 130 | Tyr | Asp | Phe | Arg | Asp 135 | Leu | Thr | Trp | Cys | Ile 140 | Asn | Pro | Pro Glu |

```
Arg  Ile  Lys  Leu  Asp  Tyr  Asp  Gln  Tyr  Cys  Ala  Asp  Val  Ala  Ala  Glu
145                 150                      155                      160

Glu  Leu  Met  Asn  Ala  Leu  Val  Asn  Ser  Thr  Leu  Leu  Glu  Ala  Arg  Thr
                165                 170                      175

Thr  Asn  Gln  Phe  Leu  Ala  Val  Ser  Lys  Gly  Asn  Cys  Ser  Gly  Pro  Thr
               180                 185                      190

Thr  Ile  Arg  Gly  Gln  Phe  Ser  Asn  Met  Ser  Leu  Ser  Leu  Leu  Asp  Leu
          195                      200                      205

Tyr  Leu  Ser  Arg  Gly  Tyr  Asn  Val  Ser  Ser  Ile  Val  Thr  Met  Thr  Ser
     210                      215                 220

Gln  Gly  Met  Tyr  Gly  Gly  Thr  Tyr  Leu  Val  Glu  Lys  Pro  Asn  Leu  Ser
225                      230                 235                           240

Ser  Lys  Gly  Ser  Glu  Leu  Ser  Gln  Leu  Ser  Met  His  Arg  Val  Phe  Glu
               245                      250                      255

Val  Gly  Val  Ile  Arg  Asn  Pro  Gly  Leu  Gly  Ala  Pro  Val  Phe  His  Met
               260                 265                      270

Thr  Asn  Tyr  Phe  Glu  Gln  Pro  Val  Ser  Asn  Asp  Phe  Ser  Asn  Cys  Met
          275                      280                      285

Val  Ala  Leu  Gly  Glu  Leu  Lys  Phe  Ala  Ala  Leu  Cys  His  Arg  Glu  Asp
290                      295                      300

Phe  Ile  Thr  Ile  Pro  Tyr  Gln  Gly  Ser  Gly  Lys  Gly  Val  Ser  Phe  Arg
305                      310                 315                           320

Leu  Val  Lys  Leu  Gly  Val  Trp  Lys  Ser  Pro  Thr  Asp  Met  Gln  Ser  Trp
               325                      330                      335

Val  Pro  Leu  Ser  Thr  Asp  Asp  Pro  Val  Ile  Asp  Lys  Leu  Tyr  Leu  Ser
               340                      345                      350

Ser  His  Arg  Gly  Val  Ile  Ala  Asp  Asn  Gln  Ala  Lys  Trp  Ala  Val  Pro
          355                      360                      365

Thr  Thr  Arg  Thr  Asp  Asp  Lys  Leu  Arg  Met  Glu  Thr  Cys  Phe  Gln  Gln
          370                      375                 380

Ala  Cys  Lys  Gly  Arg  Ile  Gln  Ala  Leu  Cys  Glu  Asn  Pro  Glu  Trp  Ala
385                      390                      395                      400

Pro  Leu  Lys  Asp  Asn  Arg  Ile  Pro  Ser  Tyr  Gly  Val  Leu  Ser  Val  Asn
                    405                      410                      415

Leu  Ser  Leu  Thr  Val  Glu  Leu  Lys  Ile  Lys  Ile  Ala  Ser  Gly  Phe  Gly
               420                      425                      430

Pro  Leu  Ile  Thr  His  Gly  Ser  Gly  Met  Asp  Leu  Tyr  Lys  Ser  Asn  His
          435                      440                      445

Asn  Asn  Val  Tyr  Trp  Leu  Thr  Ile  Pro  Pro  Met  Lys  Asn  Leu  Ala  Leu
450                            455                      460

Gly  Val  Ile  Asn  Thr  Leu  Glu  Trp  Ile  Pro  Arg  Phe  Lys  Val  Ser  Pro
465                      470                      475                      480

Asn  Leu  Phe  Thr  Ile  Pro  Ile  Lys  Glu  Ala  Gly  Glu  Asp  Cys  His  Ala
               485                      490                      495

Pro  Thr  Tyr  Leu  Ser  Ala  Glu  Val  Asp  Gly  Asp  Val  Lys  Leu  Ser  Ser
               500                      505                      510

Asn  Leu  Val  Ile  Leu  Pro  Gly  Gln  Asp  Leu  Gln  Tyr  Val  Leu  Ala  Thr
               515                      520                      525

Tyr  Asp  Thr  Ser  Arg  Val  Glu  His  Ala  Val  Val  Tyr  Tyr  Val  Tyr  Asn
     530                      535                      540

Pro  Ser  Arg  Ser  Phe  Ser  Tyr  Phe  Tyr  Pro  Phe  Arg  Leu  Pro  Val  Lys
545                      550                      555                      560

Gly  Phe  Pro  Ile  Glu  Leu  Gln  Val  Glu  Cys  Phe  Thr  Trp  Asp  Gln  Lys
               565                      570                      575
```

-continued

```
Leu Trp Cys Arg His Phe Cys Val Leu Ala Asp Ser Glu Ser Gly Gly
            580                 585                 590
His Ile Thr His Ser Gly Met Val Gly Met Gly Val Ser Cys Thr Val
        595                 600                 605
Thr Arg Glu Asp Gly Thr Asn Arg Arg
    610                 615
```

(2) INFORMATION FOR SEQ ID NO:11:

(i) SEQUENCE CHARACTERISTICS:
        (A) LENGTH: 1919 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: McI HA (ix) FEATURE:
        (A) NAME/KEY: CDS
        (B) LOCATION: 21..1874

(xi) SEQUENCE DESCRIPTION: SEQ ID NO:11:

```
AGGGTGCAAG ATCATCCACA ATG TCA CCA CAA CGA GAC CGG ATA AAT GCC        50
                      Met Ser Pro Gln Arg Asp Arg Ile Asn Ala
                        1               5                  10

TTC TAC AAA GAC AAC CCC CAT CCT AGG GGA AGT AGG ATA GTT ATT AAC      98
Phe Tyr Lys Asp Asn Pro His Pro Arg Gly Ser Arg Ile Val Ile Asn
                15                  20                  25

AGA GAA CAT CTT ATG ATT GAT AGA CCT TAT GTT TTG CTG GCT GTT CTA     146
Arg Glu His Leu Met Ile Asp Arg Pro Tyr Val Leu Leu Ala Val Leu
            30                  35                  40

TTC GTC ATG TTT CTG AGC TTG ATC GGG TTG CTA GCC ATT GCA GGC ATA     194
Phe Val Met Phe Leu Ser Leu Ile Gly Leu Leu Ala Ile Ala Gly Ile
        45                  50                  55

AGA CTT CAT CGG GCA GCC ATC TAC ACC GCA GAG ATC CAT AAA AGC CTC     242
Arg Leu His Arg Ala Ala Ile Tyr Thr Ala Glu Ile His Lys Ser Leu
    60                  65                  70

AGC ACC AAT CTA GAT GTA ACT AAC TCA ATC GAG CAT CAG GTC AAG GAC     290
Ser Thr Asn Leu Asp Val Thr Asn Ser Ile Glu His Gln Val Lys Asp
75                  80                  85                  90

GTG CTG ACA CCA CTC TTC AAG ATC ATC GGT GAT GAA GTG GGC CTG AGG     338
Val Leu Thr Pro Leu Phe Lys Ile Ile Gly Asp Glu Val Gly Leu Arg
                95                 100                 105

ACA CCT CAG AGA TTC ACC GAC CTA GTG AAA TTC ATC TCT GAC AAG ATT     386
Thr Pro Gln Arg Phe Thr Asp Leu Val Lys Phe Ile Ser Asp Lys Ile
            110                 115                 120

AAA TTC CTT AAT CCG GAT AGG GAG TAC GAC TTC AGA GAT CTC ACT TGG     434
Lys Phe Leu Asn Pro Asp Arg Glu Tyr Asp Phe Arg Asp Leu Thr Trp
        125                 130                 135

TGT ATC AAC CCG CCA GAG AGA ATC AAA TTG GAT TAT GAT CAA TAC TGT     482
Cys Ile Asn Pro Pro Glu Arg Ile Lys Leu Asp Tyr Asp Gln Tyr Cys
    140                 145                 150

GCA GAT GTG GCT GCT GAA GAA CTC ATG AAT GCA TTG GTG AAC TCA ACT     530
Ala Asp Val Ala Ala Glu Glu Leu Met Asn Ala Leu Val Asn Ser Thr
155                 160                 165                 170

CTA CTG GAG GCC AGG GTA ACC AAT CAG TTC CTA GCT GTC TCA AAG GGA     578
Leu Leu Glu Ala Arg Val Thr Asn Gln Phe Leu Ala Val Ser Lys Gly
                175                 180                 185

AAC TGC TCA GGG CCC ACT ACA ATC AGA GGT CAA TTC TCA AAC ATG TCG     626
Asn Cys Ser Gly Pro Thr Thr Ile Arg Gly Gln Phe Ser Asn Met Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     |     |     | 190 |     |     |     |     | 195 |     |     |     | 200 |      |
| CTG | TCC | CTG | TTG | GAC | TTG | TAT | TTA | AAT | CGA | GGT | TAC | AAT | GTG | TCA | TCT | 674  |
| Leu | Ser | Leu | Leu | Asp | Leu | Tyr | Leu | Asn | Arg | Gly | Tyr | Asn | Val | Ser | Ser |      |
|     |     | 205 |     |     |     | 210 |     |     |     |     |     | 215 |     |     |     |      |
| ATA | GTC | ACT | ATG | ACA | TCC | CAG | GGA | ATG | TAC | GGG | GGA | ACT | TAC | CTA | GTG | 722  |
| Ile | Val | Thr | Met | Thr | Ser | Gln | Gly | Met | Tyr | Gly | Gly | Thr | Tyr | Leu | Val |      |
|     |     | 220 |     |     |     | 225 |     |     |     |     | 230 |     |     |     |     |      |
| GAA | AAG | CCT | AAT | CTG | AGC | AGT | AAA | GGG | TCA | GAG | TTG | TCA | CAA | CTG | AGC | 770  |
| Glu | Lys | Pro | Asn | Leu | Ser | Ser | Lys | Gly | Ser | Glu | Leu | Ser | Gln | Leu | Ser |      |
| 235 |     |     |     |     | 240 |     |     |     |     | 245 |     |     |     |     | 250 |      |
| ATG | CAC | CGA | GTG | TTT | GAA | GTA | GGT | GTT | ATC | AGA | AAT | CCG | GGT | TTG | GGG | 818  |
| Met | His | Arg | Val | Phe | Glu | Val | Gly | Val | Ile | Arg | Asn | Pro | Gly | Leu | Gly |      |
|     |     |     |     | 255 |     |     |     |     | 260 |     |     |     |     | 265 |     |      |
| GCT | CCG | GTG | TTC | CAT | ATG | ACA | AAC | TAT | TTT | GAG | CAA | CCA | GTC | AGT | AAT | 866  |
| Ala | Pro | Val | Phe | His | Met | Thr | Asn | Tyr | Phe | Glu | Gln | Pro | Val | Ser | Asn |      |
|     |     | 270 |     |     |     |     | 275 |     |     |     |     | 280 |     |     |     |      |
| GAT | TTC | AGC | AAC | TGC | ATG | GTG | GCT | TTG | GGG | GAG | CTC | AAA | TTC | GCA | GCC | 914  |
| Asp | Phe | Ser | Asn | Cys | Met | Val | Ala | Leu | Gly | Glu | Leu | Lys | Phe | Ala | Ala |      |
|     |     | 285 |     |     |     | 290 |     |     |     |     | 295 |     |     |     |     |      |
| CTT | TGT | CAC | AGG | GAA | GAT | TCT | ATC | ACA | ATT | CCC | TAT | CAG | GGA | TCA | GGG | 962  |
| Leu | Cys | His | Arg | Glu | Asp | Ser | Ile | Thr | Ile | Pro | Tyr | Gln | Gly | Ser | Gly |      |
|     | 300 |     |     |     |     | 305 |     |     |     |     | 310 |     |     |     |     |      |
| AAA | GGT | GTC | AGC | TTC | CAG | CTC | GTC | AAG | CTA | GGT | GTC | TGG | AAA | TCC | CCA | 1010 |
| Lys | Gly | Val | Ser | Phe | Gln | Leu | Val | Lys | Leu | Gly | Val | Trp | Lys | Ser | Pro |      |
| 315 |     |     |     |     | 320 |     |     |     |     | 325 |     |     |     |     | 330 |      |
| ACC | GAC | ATG | CAA | TCC | TGG | GTC | CCC | CTA | TCA | ACG | GAT | GAT | CCA | GTG | ATA | 1058 |
| Thr | Asp | Met | Gln | Ser | Trp | Val | Pro | Leu | Ser | Thr | Asp | Asp | Pro | Val | Ile |      |
|     |     |     |     | 335 |     |     |     |     | 340 |     |     |     |     | 345 |     |      |
| GAC | AGG | CTC | TAC | CTC | TCA | TCT | CAC | AGA | GGC | GTT | ATC | GCT | GAC | AAT | CAA | 1106 |
| Asp | Arg | Leu | Tyr | Leu | Ser | Ser | His | Arg | Gly | Val | Ile | Ala | Asp | Asn | Gln |      |
|     |     |     | 350 |     |     |     |     | 355 |     |     |     |     | 360 |     |     |      |
| GCA | AAA | TGG | GCT | GTC | CCG | ACA | ACA | CGG | ACA | GAT | GAC | AAG | TTG | CGA | ATG | 1154 |
| Ala | Lys | Trp | Ala | Val | Pro | Thr | Thr | Arg | Thr | Asp | Asp | Lys | Leu | Arg | Met |      |
|     |     | 365 |     |     |     |     | 370 |     |     |     |     | 375 |     |     |     |      |
| GAG | ACA | TGC | TTC | CAG | CAG | GCG | TGT | AAG | GGT | AAA | ATC | CAA | GCA | CTC | TGC | 1202 |
| Glu | Thr | Cys | Phe | Gln | Gln | Ala | Cys | Lys | Gly | Lys | Ile | Gln | Ala | Leu | Cys |      |
|     | 380 |     |     |     |     | 385 |     |     |     |     | 390 |     |     |     |     |      |
| GAG | AAT | CCC | GAG | TGG | GCA | CCA | TTG | AAG | GAT | AAC | AGG | ATT | CCT | TCA | TAC | 1250 |
| Glu | Asn | Pro | Glu | Trp | Ala | Pro | Leu | Lys | Asp | Asn | Arg | Ile | Pro | Ser | Tyr |      |
| 395 |     |     |     |     | 400 |     |     |     |     | 405 |     |     |     |     | 410 |      |
| GGG | GTC | TTG | TCT | GTT | AAT | CTG | AGT | CTG | ACA | GTT | GAG | CTT | AAA | ATC | AAA | 1298 |
| Gly | Val | Leu | Ser | Val | Asn | Leu | Ser | Leu | Thr | Val | Glu | Leu | Lys | Ile | Lys |      |
|     |     |     |     | 415 |     |     |     |     | 420 |     |     |     |     | 425 |     |      |
| ATT | GCT | TCA | GGA | TTC | GGG | CCA | TTG | ATC | ACA | CAC | GGT | TCA | GGG | ATG | GAC | 1346 |
| Ile | Ala | Ser | Gly | Phe | Gly | Pro | Leu | Ile | Thr | His | Gly | Ser | Gly | Met | Asp |      |
|     |     |     | 430 |     |     |     |     | 435 |     |     |     |     | 440 |     |     |      |
| CTA | TAC | AAA | TCC | AAC | CAC | AAC | AAT | GTG | TAT | TGG | CTG | ACT | ATC | CCG | CCA | 1394 |
| Leu | Tyr | Lys | Ser | Asn | His | Asn | Asn | Val | Tyr | Trp | Leu | Thr | Ile | Pro | Pro |      |
|     |     | 445 |     |     |     |     | 450 |     |     |     |     | 455 |     |     |     |      |
| ATG | AAG | AAC | CTA | GCC | TTA | GGT | GTA | ATC | AAC | ACA | TTG | GAG | TGG | ATA | CCG | 1442 |
| Met | Lys | Asn | Leu | Ala | Leu | Gly | Val | Ile | Asn | Thr | Leu | Glu | Trp | Ile | Pro |      |
|     | 460 |     |     |     |     | 465 |     |     |     |     | 470 |     |     |     |     |      |
| AGA | TTC | AAG | GTT | AGT | CCC | AAC | CTC | TTC | ACT | GTT | CCA | ATT | AAG | GAA | GCA | 1490 |
| Arg | Phe | Lys | Val | Ser | Pro | Asn | Leu | Phe | Thr | Val | Pro | Ile | Lys | Glu | Ala |      |
| 475 |     |     |     |     | 480 |     |     |     |     | 485 |     |     |     |     | 490 |      |
| GGC | GAG | GAC | TGC | CAT | GCC | CCA | ACA | TAC | CTA | CCT | GCG | GAG | GTG | GAT | GGT | 1538 |
| Gly | Glu | Asp | Cys | His | Ala | Pro | Thr | Tyr | Leu | Pro | Ala | Glu | Val | Asp | Gly |      |
|     |     |     |     | 495 |     |     |     |     | 500 |     |     |     |     | 505 |     |      |
| GAT | GTC | AAA | CTC | AGT | TCC | AAT | CTG | GTG | ATT | CTA | CCT | GGT | CAA | GAT | CTC | 1586 |
| Asp | Val | Lys | Leu | Ser | Ser | Asn | Leu | Val | Ile | Leu | Pro | Gly | Gln | Asp | Leu |      |

|  |  |  |  |  |  | 510 |  |  |  |  | 515 |  |  |  |  | 520 |  |  |
|---|---|---|---|---|---|---|---|---|---|---|---|---|---|---|---|---|---|---|
| CAA | TAT | GTT | TTG | GCA | ACC | TAT | GAT | ACT | TCC | AGA | GTT | GAA | CAT | GCT | GTG |  |  | 1634 |
| Gln | Tyr | Val | Leu | Ala | Thr | Tyr | Asp | Thr | Ser | Arg | Val | Glu | His | Ala | Val |  |  |  |
|  |  | 525 |  |  |  | 530 |  |  |  |  | 535 |  |  |  |  |  |  |  |
| GTT | TAT | TAC | GTT | TAC | AGC | CCA | AGC | CGC | TCA | TTT | TCT | TAC | TTT | TAT | CCT |  |  | 1682 |
| Val | Tyr | Tyr | Val | Tyr | Ser | Pro | Ser | Arg | Ser | Phe | Ser | Tyr | Phe | Tyr | Pro |  |  |  |
|  |  | 540 |  |  |  | 545 |  |  |  |  | 550 |  |  |  |  |  |  |  |
| TTT | AGG | TTG | CCT | ATA | AGG | GGG | GTC | CCC | ATC | GAA | TTA | CAA | GTG | GAA | TGC |  |  | 1730 |
| Phe | Arg | Leu | Pro | Ile | Arg | Gly | Val | Pro | Ile | Glu | Leu | Gln | Val | Glu | Cys |  |  |  |
| 555 |  |  |  |  | 560 |  |  |  |  | 565 |  |  |  |  | 570 |  |  |  |
| TTC | ACA | TGG | GAC | CAA | AAA | CTC | TGG | TGC | CGT | CAC | TTC | TGT | GTG | CTT | GCG |  |  | 1778 |
| Phe | Thr | Trp | Asp | Gln | Lys | Leu | Trp | Cys | Arg | His | Phe | Cys | Val | Leu | Ala |  |  |  |
|  |  |  |  | 575 |  |  |  |  | 580 |  |  |  |  | 585 |  |  |  |  |
| GAC | TCA | GAA | TCT | GGT | GGA | TAT | ATC | ACT | CAC | TCT | GGG | ATG | GTG | GGC | ATG |  |  | 1826 |
| Asp | Ser | Glu | Ser | Gly | Gly | Tyr | Ile | Thr | His | Ser | Gly | Met | Val | Gly | Met |  |  |  |
|  |  | 590 |  |  |  |  |  | 595 |  |  |  | 600 |  |  |  |  |  |  |
| GGA | GTC | AGC | TGC | ACA | GTC | ACC | CGG | GAA | GAT | GGA | ACC | AAC | CGC | AGA |  |  |  | 1871 |
| Gly | Val | Ser | Cys | Thr | Val | Thr | Arg | Glu | Asp | Gly | Thr | Asn | Arg | Arg |  |  |  |  |
|  |  | 605 |  |  |  | 610 |  |  |  |  | 615 |  |  |  |  |  |  |  |

TAGGGCTGCT                                                                                              1881

AGTGAACCAA TCTCATGATG TCACCCAGAC ATCAGGCA                                                               1919

( 2 ) INFORMATION FOR SEQ ID NO:12:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| Met | Ser | Pro | Gln | Arg | Asp | Arg | Ile | Asn | Ala | Phe | Tyr | Lys | Asp | Asn | Pro |
|---|---|---|---|---|---|---|---|---|---|---|---|---|---|---|---|
| 1 |  |  |  | 5 |  |  |  |  | 10 |  |  |  |  | 15 |  |
| His | Pro | Arg | Gly | Ser | Arg | Ile | Val | Ile | Asn | Arg | Glu | His | Leu | Met | Ile |
|  |  |  | 20 |  |  |  |  | 25 |  |  |  |  | 30 |  |  |
| Asp | Arg | Pro | Tyr | Val | Leu | Leu | Ala | Val | Leu | Phe | Val | Met | Phe | Leu | Ser |
|  |  | 35 |  |  |  |  | 40 |  |  |  |  | 45 |  |  |  |
| Leu | Ile | Gly | Leu | Leu | Ala | Ile | Ala | Gly | Ile | Arg | Leu | His | Arg | Ala | Ala |
|  | 50 |  |  |  |  | 55 |  |  |  |  | 60 |  |  |  |  |
| Ile | Tyr | Thr | Ala | Glu | Ile | His | Lys | Ser | Leu | Ser | Thr | Asn | Leu | Asp | Val |
| 65 |  |  |  |  | 70 |  |  |  |  | 75 |  |  |  |  | 80 |
| Thr | Asn | Ser | Ile | Glu | His | Gln | Val | Lys | Asp | Val | Leu | Thr | Pro | Leu | Phe |
|  |  |  |  | 85 |  |  |  |  | 90 |  |  |  |  | 95 |  |
| Lys | Ile | Ile | Gly | Asp | Glu | Val | Gly | Leu | Arg | Thr | Pro | Gln | Arg | Phe | Thr |
|  |  |  | 100 |  |  |  |  | 105 |  |  |  |  | 110 |  |  |
| Asp | Leu | Val | Lys | Phe | Ile | Ser | Asp | Lys | Ile | Lys | Phe | Leu | Asn | Pro | Asp |
|  |  | 115 |  |  |  |  | 120 |  |  |  |  | 125 |  |  |  |
| Arg | Glu | Tyr | Asp | Phe | Arg | Asp | Leu | Thr | Trp | Cys | Ile | Asn | Pro | Pro | Glu |
|  | 130 |  |  |  |  | 135 |  |  |  |  | 140 |  |  |  |  |
| Arg | Ile | Lys | Leu | Asp | Tyr | Asp | Gln | Tyr | Cys | Ala | Asp | Val | Ala | Ala | Glu |
| 145 |  |  |  |  | 150 |  |  |  |  | 155 |  |  |  |  | 160 |
| Glu | Leu | Met | Asn | Ala | Leu | Val | Asn | Ser | Thr | Leu | Leu | Glu | Ala | Arg | Val |
|  |  |  |  | 165 |  |  |  |  | 170 |  |  |  |  | 175 |  |
| Thr | Asn | Gln | Phe | Leu | Ala | Val | Ser | Lys | Gly | Asn | Cys | Ser | Gly | Pro | Thr |
|  |  |  | 180 |  |  |  |  | 185 |  |  |  |  | 190 |  |  |
| Thr | Ile | Arg | Gly | Gln | Phe | Ser | Asn | Met | Ser | Leu | Ser | Leu | Leu | Asp | Leu |
|  |  | 195 |  |  |  |  | 200 |  |  |  |  | 205 |  |  |  |

```
Tyr Leu Asn Arg Gly Tyr Asn Val Ser Ser Ile Val Thr Met Thr Ser
    210             215             220
Gln Gly Met Tyr Gly Gly Thr Tyr Leu Val Glu Lys Pro Asn Leu Ser
225             230             235                     240
Ser Lys Gly Ser Glu Leu Ser Gln Leu Ser Met His Arg Val Phe Glu
                245             250                 255
Val Gly Val Ile Arg Asn Pro Gly Leu Gly Ala Pro Val Phe His Met
                260             265             270
Thr Asn Tyr Phe Glu Gln Pro Val Ser Asn Asp Phe Ser Asn Cys Met
            275             280             285
Val Ala Leu Gly Glu Leu Lys Phe Ala Ala Leu Cys His Arg Glu Asp
    290             295             300
Ser Ile Thr Ile Pro Tyr Gln Gly Ser Gly Lys Gly Val Ser Phe Gln
305             310             315                     320
Leu Val Lys Leu Gly Val Trp Lys Ser Pro Thr Asp Met Gln Ser Trp
                325             330             335
Val Pro Leu Ser Thr Asp Asp Pro Val Ile Asp Arg Leu Tyr Leu Ser
            340             345             350
Ser His Arg Gly Val Ile Ala Asp Asn Gln Ala Lys Trp Ala Val Pro
        355             360             365
Thr Thr Arg Thr Asp Asp Lys Leu Arg Met Glu Thr Cys Phe Gln Gln
370             375             380
Ala Cys Lys Gly Lys Ile Gln Ala Leu Cys Glu Asn Pro Glu Trp Ala
385             390             395             400
Pro Leu Lys Asp Asn Arg Ile Pro Ser Tyr Gly Val Leu Ser Val Asn
                405             410             415
Leu Ser Leu Thr Val Glu Leu Lys Ile Lys Ile Ala Ser Gly Phe Gly
            420             425             430
Pro Leu Ile Thr His Gly Ser Gly Met Asp Leu Tyr Lys Ser Asn His
        435             440             445
Asn Asn Val Tyr Trp Leu Thr Ile Pro Pro Met Lys Asn Leu Ala Leu
    450             455             460
Gly Val Ile Asn Thr Leu Glu Trp Ile Pro Arg Phe Lys Val Ser Pro
465             470             475             480
Asn Leu Phe Thr Val Pro Ile Lys Glu Ala Gly Glu Asp Cys His Ala
                485             490             495
Pro Thr Tyr Leu Pro Ala Glu Val Asp Gly Asp Val Lys Leu Ser Ser
            500             505             510
Asn Leu Val Ile Leu Pro Gly Gln Asp Leu Gln Tyr Val Leu Ala Thr
        515             520             525
Tyr Asp Thr Ser Arg Val Glu His Ala Val Val Tyr Tyr Val Tyr Ser
    530             535             540
Pro Ser Arg Ser Phe Ser Tyr Phe Tyr Pro Phe Arg Leu Pro Ile Arg
545             550             555             560
Gly Val Pro Ile Glu Leu Gln Val Glu Cys Phe Thr Trp Asp Gln Lys
                565             570             575
Leu Trp Cys Arg His Phe Cys Val Leu Ala Asp Ser Glu Ser Gly Gly
            580             585             590
Tyr Ile Thr His Ser Gly Met Val Gly Met Gly Val Ser Cys Thr Val
        595             600             605
Thr Arg Glu Asp Gly Thr Asn Arg Arg
610             615
```

( 2 ) INFORMATION FOR SEQ ID NO:13:

( i ) SEQUENCE CHARACTERISTICS:
        ( A ) LENGTH: 1919 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: JM HA ( i x ) FEATURE:
        ( A ) NAME/KEY: CDS
        ( B ) LOCATION: 21..1874

( x i ) SEQUENCE DESCRIPTION: SEQ ID NO:13:

```
AGGGTGCAAG ATCATCCACA ATG TCA CCA CAA CGA GAC CGG ATA AAT GCC            50
                     Met Ser Pro Gln Arg Asp Arg Ile Asn Ala
                      1               5                  10

TTC TAC AAA GAT AAC CCC CAT CCC AAG GGA AGT AGG ATA GTT ATC AAC         98
Phe Tyr Lys Asp Asn Pro His Pro Lys Gly Ser Arg Ile Val Ile Asn
            15                  20                  25

AGA GAA CAC CTT ATG ATT GAT AGA CCT TAT GTT TTG CTG GCT GTT CTG        146
Arg Glu His Leu Met Ile Asp Arg Pro Tyr Val Leu Leu Ala Val Leu
                30                  35                  40

TTC GTC ATG TTT CTG AGC TTG ATC GGG TTG CTA GCC ATT GCA GGC ATT        194
Phe Val Met Phe Leu Ser Leu Ile Gly Leu Leu Ala Ile Ala Gly Ile
            45                  50                  55

AGA CTT CAT CGG GCA GCC ATC TAC ACC GCA GAG ATC CAT AAA AGC CTC        242
Arg Leu His Arg Ala Ala Ile Tyr Thr Ala Glu Ile His Lys Ser Leu
        60                  65                  70

AGC ACC AAT CTA GAT GTA ACT AAC TCA ATT GAG CAT CAG GTC AAG GAC        290
Ser Thr Asn Leu Asp Val Thr Asn Ser Ile Glu His Gln Val Lys Asp
75                  80                  85                  90

GTG CTG ACA CCA CTC TTC AAA ATC ATC GGT GAT GAA GTG GGC CTG AGG        338
Val Leu Thr Pro Leu Phe Lys Ile Ile Gly Asp Glu Val Gly Leu Arg
                95                 100                 105

ACA CCT CAG AGA TTC ACT GAC CTA GTG AAA TTC ATC TCT GAC AAG ATT        386
Thr Pro Gln Arg Phe Thr Asp Leu Val Lys Phe Ile Ser Asp Lys Ile
            110                 115                 120

AAA TTC CTT AAC CCG GAT AGG GAG TAC GAC TTC AGA GAT CTC ACT TGG        434
Lys Phe Leu Asn Pro Asp Arg Glu Tyr Asp Phe Arg Asp Leu Thr Trp
        125                 130                 135

TGT ATC AAC CCG CCA GAG AGA ATC AAA TTG GAT TAT GAT CAA TAC TGT        482
Cys Ile Asn Pro Pro Glu Arg Ile Lys Leu Asp Tyr Asp Gln Tyr Cys
140                 145                 150

GCA GAT GTG GCT GCT GAA GAG CTC ATG AAT GCA TTG GTG AAC TCA ACT        530
Ala Asp Val Ala Ala Glu Glu Leu Met Asn Ala Leu Val Asn Ser Thr
155                 160                 165                 170

CTA CTG GAG ACC AGA ACA ACC AAT CAG TTC CTA GCT GTC TCA AAG GGA        578
Leu Leu Glu Thr Arg Thr Thr Asn Gln Phe Leu Ala Val Ser Lys Gly
                175                 180                 185

AAC TGC TCA GGG CCC ACT ACA ATC AGA GGT CAA TTC TCA AAC ATG TCG        626
Asn Cys Ser Gly Pro Thr Thr Ile Arg Gly Gln Phe Ser Asn Met Ser
            190                 195                 200

CTG TCC CTG TTG GAC TTG TAT TTA AGT CGA GGT TAC AAT GTG TCA TCT        674
Leu Ser Leu Leu Asp Leu Tyr Leu Ser Arg Gly Tyr Asn Val Ser Ser
        205                 210                 215

ATA GTC ACT ATG ACA TCC CAG GGA ATG TAC GGG GGA ACT TAC CTA GTG        722
Ile Val Thr Met Thr Ser Gln Gly Met Tyr Gly Gly Thr Tyr Leu Val
220                 225                 230

GAA AAG CCT AAT CTG AGC AGC AAA GGG TCA GAG TTG TCA CAA CTG AGC        770
```

| | | | | | | | | | | | | | | | |
|---|---|---|---|---|---|---|---|---|---|---|---|---|---|---|---|
| Glu | Lys | Pro | Asn | Leu | Ser | Ser | Lys | Gly | Ser | Glu | Leu | Ser | Gln | Leu | Ser |
| 235 | | | | 240 | | | | | 245 | | | | | 250 | |

| ATG | TAC | CGA | GTG | TTT | GAA | GTA | GGT | GTT | ATC | AGA | AAT | CCG | GGT | TTG | GGG | 818 |
|---|---|---|---|---|---|---|---|---|---|---|---|---|---|---|---|---|
| Met | Tyr | Arg | Val | Phe | Glu | Val | Gly | Val | Ile | Arg | Asn | Pro | Gly | Leu | Gly | |
| | | | | 255 | | | | | 260 | | | | | 265 | | |

| GCT | CCG | GTG | TTC | CAT | ATG | ACA | AAC | TAT | TTT | GAG | CAA | CCA | GTC | AGT | AAT | 866 |
|---|---|---|---|---|---|---|---|---|---|---|---|---|---|---|---|---|
| Ala | Pro | Val | Phe | His | Met | Thr | Asn | Tyr | Phe | Glu | Gln | Pro | Val | Ser | Asn | |
| | | | | 270 | | | | | 275 | | | | | 280 | | |

| GAT | CTC | AGC | AAC | TGT | ATG | GTG | GCT | TTG | GGG | GAG | CTC | AAA | CTC | GCA | GCC | 914 |
|---|---|---|---|---|---|---|---|---|---|---|---|---|---|---|---|---|
| Asp | Leu | Ser | Asn | Cys | Met | Val | Ala | Leu | Gly | Glu | Leu | Lys | Leu | Ala | Ala | |
| | | | | 285 | | | | | 290 | | | | | 295 | | |

| CTT | TGT | CAC | GGG | GGA | GAT | TCT | ATC | ACA | ATT | CCC | TAT | CAG | GGA | TCA | GGG | 962 |
|---|---|---|---|---|---|---|---|---|---|---|---|---|---|---|---|---|
| Leu | Cys | His | Gly | Gly | Asp | Ser | Ile | Thr | Ile | Pro | Tyr | Gln | Gly | Ser | Gly | |
| | | | | 300 | | | | | 305 | | | | | 310 | | |

| AAA | GGT | GTC | AGC | TTT | CAG | CTC | GTC | AAG | CTA | GGT | GTC | TGG | AAA | TCC | CCA | 1010 |
|---|---|---|---|---|---|---|---|---|---|---|---|---|---|---|---|---|
| Lys | Gly | Val | Ser | Phe | Gln | Leu | Val | Lys | Leu | Gly | Val | Trp | Lys | Ser | Pro | |
| 315 | | | | | 320 | | | | | 325 | | | | | 330 | |

| ACC | GAC | ATG | CAA | TCC | TGG | GTC | CCC | TTC | TCA | ACG | GAT | GAC | CCA | GTG | ATA | 1058 |
|---|---|---|---|---|---|---|---|---|---|---|---|---|---|---|---|---|
| Thr | Asp | Met | Gln | Ser | Trp | Val | Pro | Phe | Ser | Thr | Asp | Asp | Pro | Val | Ile | |
| | | | | 335 | | | | | 340 | | | | | 345 | | |

| GAC | AGG | CTT | TAC | CTC | TCA | TCT | CAC | AGA | GGT | GTT | ATC | GCT | GAC | AAT | CAA | 1106 |
|---|---|---|---|---|---|---|---|---|---|---|---|---|---|---|---|---|
| Asp | Arg | Leu | Tyr | Leu | Ser | Ser | His | Arg | Gly | Val | Ile | Ala | Asp | Asn | Gln | |
| | | | | 350 | | | | | 355 | | | | | 360 | | |

| GCA | AAA | TGG | GCT | ATC | CCG | ACA | ACA | AGA | ACA | GAT | GAC | AAG | TTG | CGA | ATG | 1154 |
|---|---|---|---|---|---|---|---|---|---|---|---|---|---|---|---|---|
| Ala | Lys | Trp | Ala | Ile | Pro | Thr | Thr | Arg | Thr | Asp | Asp | Lys | Leu | Arg | Met | |
| | | | 365 | | | | | 370 | | | | | 375 | | | |

| GAG | ACA | TGC | TTC | CAG | CAG | GCG | TGT | AAG | GGT | AAA | ATC | CAA | GCA | CTC | TGC | 1202 |
|---|---|---|---|---|---|---|---|---|---|---|---|---|---|---|---|---|
| Glu | Thr | Cys | Phe | Gln | Gln | Ala | Cys | Lys | Gly | Lys | Ile | Gln | Ala | Leu | Cys | |
| | 380 | | | | | 385 | | | | | 390 | | | | | |

| GAG | AAT | CCC | GAG | TGG | GCA | CCA | TTG | AAG | GAT | AAC | AGG | ATT | CCT | TCA | TAC | 1250 |
|---|---|---|---|---|---|---|---|---|---|---|---|---|---|---|---|---|
| Glu | Asn | Pro | Glu | Trp | Ala | Pro | Leu | Lys | Asp | Asn | Arg | Ile | Pro | Ser | Tyr | |
| 395 | | | | | 400 | | | | | 405 | | | | | 410 | |

| GGA | GTC | TTG | TCT | GTT | GAT | CTG | AGT | CTA | ACA | GTT | GAG | CTT | AAA | ATC | AAA | 1298 |
|---|---|---|---|---|---|---|---|---|---|---|---|---|---|---|---|---|
| Gly | Val | Leu | Ser | Val | Asp | Leu | Ser | Leu | Thr | Val | Glu | Leu | Lys | Ile | Lys | |
| | | | | 415 | | | | | 420 | | | | | 425 | | |

| ATT | GCT | TCG | GGA | TTC | GGG | CCA | TTG | ATC | ACA | CAC | GGT | TCA | GGG | ATG | GAC | 1346 |
|---|---|---|---|---|---|---|---|---|---|---|---|---|---|---|---|---|
| Ile | Ala | Ser | Gly | Phe | Gly | Pro | Leu | Ile | Thr | His | Gly | Ser | Gly | Met | Asp | |
| | | | 430 | | | | | 435 | | | | | 440 | | | |

| CTA | TAC | AAG | TCC | AAC | CAC | AAC | AAT | GAG | TAT | TGG | CTG | ACT | ATC | CCG | CCA | 1394 |
|---|---|---|---|---|---|---|---|---|---|---|---|---|---|---|---|---|
| Leu | Tyr | Lys | Ser | Asn | His | Asn | Asn | Glu | Tyr | Trp | Leu | Thr | Ile | Pro | Pro | |
| | | 445 | | | | | 450 | | | | | 455 | | | | |

| ATG | AAG | AAC | CTA | GCC | CTA | GGT | GTA | ATC | AAC | ACA | TTG | GAG | TGG | ATA | CCG | 1442 |
|---|---|---|---|---|---|---|---|---|---|---|---|---|---|---|---|---|
| Met | Lys | Asn | Leu | Ala | Leu | Gly | Val | Ile | Asn | Thr | Leu | Glu | Trp | Ile | Pro | |
| | 460 | | | | | 465 | | | | | 470 | | | | | |

| AGA | TTC | AAG | GTT | AGT | CCC | AAC | CTC | TTC | ACT | GTC | CCA | ATT | AAG | GAA | GCA | 1490 |
|---|---|---|---|---|---|---|---|---|---|---|---|---|---|---|---|---|
| Arg | Phe | Lys | Val | Ser | Pro | Asn | Leu | Phe | Thr | Val | Pro | Ile | Lys | Glu | Ala | |
| 475 | | | | | 480 | | | | | 485 | | | | | 490 | |

| GGC | GAA | GAC | TGC | CAT | GCC | CCA | ACA | TAC | CTA | CCT | GCG | GAG | GTG | GAT | GGT | 1538 |
|---|---|---|---|---|---|---|---|---|---|---|---|---|---|---|---|---|
| Gly | Glu | Asp | Cys | His | Ala | Pro | Thr | Tyr | Leu | Pro | Ala | Glu | Val | Asp | Gly | |
| | | | | 495 | | | | | 500 | | | | | 505 | | |

| GAT | GTC | AAA | CTC | AGT | TCC | AAT | CTG | GTG | ATC | CTA | CCT | GGT | CAA | GAT | CTC | 1586 |
|---|---|---|---|---|---|---|---|---|---|---|---|---|---|---|---|---|
| Asp | Val | Lys | Leu | Ser | Ser | Asn | Leu | Val | Ile | Leu | Pro | Gly | Gln | Asp | Leu | |
| | | | 510 | | | | | 515 | | | | | 520 | | | |

| CAA | TAT | GTT | TTG | GCA | ACC | TAC | GAT | ACT | TCC | AGG | GTT | GAA | CAT | GCT | GTG | 1634 |
|---|---|---|---|---|---|---|---|---|---|---|---|---|---|---|---|---|
| Gln | Tyr | Val | Leu | Ala | Thr | Tyr | Asp | Thr | Ser | Arg | Val | Glu | His | Ala | Val | |
| | | 525 | | | | | 530 | | | | | 535 | | | | |

| GTT | TAT | TAC | GTT | TAC | AGC | CCA | AGC | CGC | TCA | TTT | TCT | TAC | TTT | TAT | CCT | 1682 |
|---|---|---|---|---|---|---|---|---|---|---|---|---|---|---|---|---|
| Val | Tyr | Tyr | Val | Tyr | Ser | Pro | Ser | Arg | Ser | Phe | Ser | Tyr | Phe | Tyr | Pro | |
| | 540 | | | | | 545 | | | | | 550 | | | | | |

| TTT | AGG | TTG | CCT | ATA | AAG | GGG | ATC | CCC | ATC | GAA | TTA | CAA | GTG | GAA | TGC | 1730 |

|     |     |     |     |     |     |     |     |     |     |     |     |     |     |     |     |     |
|---|---|---|---|---|---|---|---|---|---|---|---|---|---|---|---|---|
| Phe | Arg | Leu | Pro | Ile | Lys | Gly | Ile | Pro | Ile | Glu | Leu | Gln | Val | Glu | Cys | |
| 555 |   |   |   | 560 |   |   |   | 565 |   |   |   |   |   | 570 | | |
| TTC | ACA | TGG | GAC | CAA | AAA | CTC | TGG | TGC | CGT | CAC | TTC | TGT | GTG | CTT | GCG | 1778 |
| Phe | Thr | Trp | Asp | Gln | Lys | Leu | Trp | Cys | Arg | His | Phe | Cys | Val | Leu | Ala | |
|   |   |   |   | 575 |   |   |   | 580 |   |   |   |   | 585 |   |   | |
| GAC | TCA | GAA | TCT | GGT | GGA | CAT | ATC | ACT | CAC | TCT | GGG | ATG | GTG | GGC | ATG | 1826 |
| Asp | Ser | Glu | Ser | Gly | Gly | His | Ile | Thr | His | Ser | Gly | Met | Val | Gly | Met | |
|   |   |   |   | 590 |   |   |   | 595 |   |   |   | 600 |   |   |   | |
| GGA | GTC | AGC | TGC | ACA | GTC | ACC | CGG | GAA | GAT | GGA | ACC | AAT | AGC | AGA |   | 1871 |
| Gly | Val | Ser | Cys | Thr | Val | Thr | Arg | Glu | Asp | Gly | Thr | Asn | Ser | Arg |   | |
|   |   | 605 |   |   |   |   | 610 |   |   |   |   | 615 |   |   |   | |
| TAGGGCTGCT | | | | | | | | | | | | | | | | 1881 |
| AGTGAACCAA | TCTCATGATG | TCACCCAGAC | ATCAGGCA | | | | | | | | | | | | | 1919 |

( 2 ) INFORMATION FOR SEQ ID NO:14:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
| Met | Ser | Pro | Gln | Arg | Asp | Arg | Ile | Asn | Ala | Phe | Tyr | Lys | Asp | Asn | Pro |
| 1 | | | | 5 | | | | 10 | | | | | | 15 | |
| His | Pro | Lys | Gly | Ser | Arg | Ile | Val | Ile | Asn | Arg | Glu | His | Leu | Met | Ile |
| | | | 20 | | | | 25 | | | | | 30 | | | |
| Asp | Arg | Pro | Tyr | Val | Leu | Leu | Ala | Val | Leu | Phe | Val | Met | Phe | Leu | Ser |
| | | 35 | | | | 40 | | | | | 45 | | | | |
| Leu | Ile | Gly | Leu | Leu | Ala | Ile | Ala | Gly | Ile | Arg | Leu | His | Arg | Ala | Ala |
| | 50 | | | | 55 | | | | | 60 | | | | | |
| Ile | Tyr | Thr | Ala | Glu | Ile | His | Lys | Ser | Leu | Ser | Thr | Asn | Leu | Asp | Val |
| 65 | | | | | 70 | | | | 75 | | | | | | 80 |
| Thr | Asn | Ser | Ile | Glu | His | Gln | Val | Lys | Asp | Val | Leu | Thr | Pro | Leu | Phe |
| | | | | 85 | | | | 90 | | | | | 95 | | |
| Lys | Ile | Ile | Gly | Asp | Glu | Val | Gly | Leu | Arg | Thr | Pro | Gln | Arg | Phe | Thr |
| | | | 100 | | | | 105 | | | | | 110 | | | |
| Asp | Leu | Val | Lys | Phe | Ile | Ser | Asp | Lys | Ile | Lys | Phe | Leu | Asn | Pro | Asp |
| | | 115 | | | | 120 | | | | | 125 | | | | |
| Arg | Glu | Tyr | Asp | Phe | Arg | Asp | Leu | Thr | Trp | Cys | Ile | Asn | Pro | Pro | Glu |
| | 130 | | | | 135 | | | | | 140 | | | | | |
| Arg | Ile | Lys | Leu | Asp | Tyr | Asp | Gln | Tyr | Cys | Ala | Asp | Val | Ala | Ala | Glu |
| 145 | | | | | 150 | | | | 155 | | | | | | 160 |
| Glu | Leu | Met | Asn | Ala | Leu | Val | Asn | Ser | Thr | Leu | Leu | Glu | Thr | Arg | Thr |
| | | | | 165 | | | | 170 | | | | | 175 | | |
| Thr | Asn | Gln | Phe | Leu | Ala | Val | Ser | Lys | Gly | Asn | Cys | Ser | Gly | Pro | Thr |
| | | | 180 | | | | 185 | | | | | 190 | | | |
| Thr | Ile | Arg | Gly | Gln | Phe | Ser | Asn | Met | Ser | Leu | Ser | Leu | Leu | Asp | Leu |
| | | 195 | | | | 200 | | | | | 205 | | | | |
| Tyr | Leu | Ser | Arg | Gly | Tyr | Asn | Val | Ser | Ser | Ile | Val | Thr | Met | Thr | Ser |
| | 210 | | | | 215 | | | | | 220 | | | | | |
| Gln | Gly | Met | Tyr | Gly | Gly | Thr | Tyr | Leu | Val | Glu | Lys | Pro | Asn | Leu | Ser |
| 225 | | | | | 230 | | | | 235 | | | | | | 240 |
| Ser | Lys | Gly | Ser | Glu | Leu | Ser | Gln | Leu | Ser | Met | Tyr | Arg | Val | Phe | Glu |
| | | | | 245 | | | | 250 | | | | | 255 | | |
| Val | Gly | Val | Ile | Arg | Asn | Pro | Gly | Leu | Gly | Ala | Pro | Val | Phe | His | Met |

|   |   |   | 260 |   |   |   | 265 |   |   |   | 270 |   |   |   |
|---|---|---|---|---|---|---|---|---|---|---|---|---|---|---|
| Thr | Asn | Tyr 275 | Phe | Glu | Gln | Pro | Val 280 | Ser | Asn | Asp | Leu 285 | Ser | Asn | Cys | Met |
| Val | Ala 290 | Leu | Gly | Glu | Leu | Lys 295 | Leu | Ala | Ala | Leu | Cys 300 | His | Gly | Gly | Asp |
| Ser 305 | Ile | Thr | Ile | Pro | Tyr 310 | Gln | Gly | Ser | Gly | Lys 315 | Gly | Val | Ser | Phe | Gln 320 |
| Leu | Val | Lys | Leu | Gly 325 | Val | Trp | Lys | Ser | Pro 330 | Thr | Asp | Met | Gln | Ser 335 | Trp |
| Val | Pro | Phe | Ser 340 | Thr | Asp | Asp | Pro | Val 345 | Ile | Asp | Arg | Leu | Tyr 350 | Leu | Ser |
| Ser | His | Arg 355 | Gly | Val | Ile | Ala | Asp 360 | Asn | Gln | Ala | Lys | Trp 365 | Ala | Ile | Pro |
| Thr | Thr 370 | Arg | Thr | Asp | Asp | Lys 375 | Leu | Arg | Met | Glu | Thr 380 | Cys | Phe | Gln | Gln |
| Ala 385 | Cys | Lys | Gly | Lys | Ile 390 | Gln | Ala | Leu | Cys | Glu 395 | Asn | Pro | Glu | Trp | Ala 400 |
| Pro | Leu | Lys | Asp | Asn 405 | Arg | Ile | Pro | Ser | Tyr 410 | Gly | Val | Leu | Ser | Val 415 | Asp |
| Leu | Ser | Leu | Thr 420 | Val | Glu | Leu | Lys | Ile 425 | Lys | Ile | Ala | Ser | Gly 430 | Phe | Gly |
| Pro | Leu | Ile 435 | Thr | His | Gly | Ser | Gly 440 | Met | Asp | Leu | Tyr | Lys 445 | Ser | Asn | His |
| Asn | Asn 450 | Glu | Tyr | Trp | Leu | Thr 455 | Ile | Pro | Pro | Met | Lys 460 | Asn | Leu | Ala | Leu |
| Gly 465 | Val | Ile | Asn | Thr | Leu 470 | Glu | Trp | Ile | Pro | Arg 475 | Phe | Lys | Val | Ser | Pro 480 |
| Asn | Leu | Phe | Thr | Val 485 | Pro | Ile | Lys | Glu | Ala 490 | Gly | Glu | Asp | Cys | His 495 | Ala |
| Pro | Thr | Tyr | Leu 500 | Pro | Ala | Glu | Val | Asp 505 | Gly | Asp | Val | Lys | Leu 510 | Ser | Ser |
| Asn | Leu | Val 515 | Ile | Leu | Pro | Gly | Gln 520 | Asp | Leu | Gln | Tyr | Val 525 | Leu | Ala | Thr |
| Tyr | Asp 530 | Thr | Ser | Arg | Val | Glu 535 | His | Ala | Val | Val | Tyr 540 | Tyr | Val | Tyr | Ser |
| Pro 545 | Ser | Arg | Ser | Phe | Ser 550 | Tyr | Phe | Tyr | Pro | Phe 555 | Arg | Leu | Pro | Ile | Lys 560 |
| Gly | Ile | Pro | Ile | Glu 565 | Leu | Gln | Val | Glu | Cys 570 | Phe | Thr | Trp | Asp | Gln 575 | Lys |
| Leu | Trp | Cys | Arg 580 | His | Phe | Cys | Val | Leu 585 | Ala | Asp | Ser | Glu | Ser 590 | Gly | Gly |
| His | Ile | Thr 595 | His | Ser | Gly | Met | Val 600 | Gly | Met | Gly | Val | Ser 605 | Cys | Thr | Val |
| Thr | Arg 610 | Glu | Asp | Gly | Thr | Asn 615 | Ser | Arg |   |   |   |   |   |   |   |

( 2 ) INFORMATION FOR SEQ ID NO:15:

( i ) SEQUENCE CHARACTERISTICS:
        ( A ) LENGTH: 1687 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:

( B ) STRAIN: Moraten [

( i x ) FEATURE:
    ( A ) NAME/KEY: CDS
    ( B ) LOCATION: 16..1668

( x i ) SEQUENCE DESCRIPTION: SEQ ID NO:15:

```
CATCCAATGT CCATC ATG GGT CTC AAG GTG AAC GTC TCT GCC ATA TTC ATG       51
                Met Gly Leu Lys Val Asn Val Ser Ala Ile Phe Met
                 1               5                      10

GCA GTA CTG TTA ACT CTC CAA ACA CCC ACC GGT CAA ATC CAT TGG GGC        99
Ala Val Leu Leu Thr Leu Gln Thr Pro Thr Gly Gln Ile His Trp Gly
         15                  20                  25

AAT CTC TCT AAG ATA GGG GTG GTA GGA ATA GGA AGT GCA AGC TAC AAA       147
Asn Leu Ser Lys Ile Gly Val Val Gly Ile Gly Ser Ala Ser Tyr Lys
     30                  35                  40

GTT ATG ACT CGT TCC AGC CAT CAA TCA TTA GTC ATA AAA TTA ATG CCC       195
Val Met Thr Arg Ser Ser His Gln Ser Leu Val Ile Lys Leu Met Pro
 45                  50                  55                  60

AAT ATA ACT CTC CTC AAT AAC TGC ACG AGG GTA GAG ATT GCA GAA TAC       243
Asn Ile Thr Leu Leu Asn Asn Cys Thr Arg Val Glu Ile Ala Glu Tyr
                 65                  70                  75

AGG AGA CTA CTG AGA ACA GTT TTG GAA CCA ATT AGA GAT GCA CTT AAT       291
Arg Arg Leu Leu Arg Thr Val Leu Glu Pro Ile Arg Asp Ala Leu Asn
             80                  85                  90

GCA ATG ACC CAG AAT ATA AGA CCG GTT CAG AGT GTA GCT TCA AGT AGG       339
Ala Met Thr Gln Asn Ile Arg Pro Val Gln Ser Val Ala Ser Ser Arg
         95                  100                 105

AGA CAC AAG AGA TTT GCG GGA GTA GTC CTG GCA GGT GCG GCC CTA GGC       387
Arg His Lys Arg Phe Ala Gly Val Val Leu Ala Gly Ala Ala Leu Gly
     110                 115                 120

GTT GCC ACA GCT GCT CAG ATA ACA GCC GGC ATT GCA CTT CAC CAG TCC       435
Val Ala Thr Ala Ala Gln Ile Thr Ala Gly Ile Ala Leu His Gln Ser
125                 130                 135                 140

ATG CTG AAC TCT CAA GCC ATC GAC AAT CTG AGA GCG AGC CTG GAA ACT       483
Met Leu Asn Ser Gln Ala Ile Asp Asn Leu Arg Ala Ser Leu Glu Thr
                 145                 150                 155

ACT AAT CAG GCA ATT GAG ACA ATC AGA CAA GCA GGG CAG GAG ATG ATA       531
Thr Asn Gln Ala Ile Glu Thr Ile Arg Gln Ala Gly Gln Glu Met Ile
             160                 165                 170

TTG GCT GTT CAG GGT GTC CAA GAC TAC ATC AAT AAT GAG CTG ATA CCG       579
Leu Ala Val Gln Gly Val Gln Asp Tyr Ile Asn Asn Glu Leu Ile Pro
         175                 180                 185

TCT ATG AAC CAA CTA TCT TGT GAT TTA ATC GGC CAG AAG CTC GGG CTC       627
Ser Met Asn Gln Leu Ser Cys Asp Leu Ile Gly Gln Lys Leu Gly Leu
     190                 195                 200

AAA TTG CTC AGA TAC TAT ACA GAA ATC CTG TCA TTA TTT GGC CCC AGT       675
Lys Leu Leu Arg Tyr Tyr Thr Glu Ile Leu Ser Leu Phe Gly Pro Ser
205                 210                 215                 220

TTA CGG GAC CCC ATA TCT GCG GAG ATA TCT ATC CAG GCT TTG AGC TAT       723
Leu Arg Asp Pro Ile Ser Ala Glu Ile Ser Ile Gln Ala Leu Ser Tyr
                 225                 230                 235

GCG CTT GGA GGA GAC ATC AAT AAG GTG TTA GAA AAG CTC GGA TAC AGT       771
Ala Leu Gly Gly Asp Ile Asn Lys Val Leu Glu Lys Leu Gly Tyr Ser
             240                 245                 250

GGA GGT GAT TTA CTG GGC ATC TTA GAG AGC GGA GGA ATA AAG GCC CGG       819
Gly Gly Asp Leu Leu Gly Ile Leu Glu Ser Gly Gly Ile Lys Ala Arg
         255                 260                 265

ATA ACT CAC GTC GAC ACA GAG TCC TAC TTC ATT GTC CTC AGT ATA GCC       867
Ile Thr His Val Asp Thr Glu Ser Tyr Phe Ile Val Leu Ser Ile Ala
     270                 275                 280
```

```
TAT  CCG  ACG  CTG  TCC  GAG  ATT  AAG  GGG  GTG  ATT  GTC  CAC  CGG  CTA  GAG      915
Tyr  Pro  Thr  Leu  Ser  Glu  Ile  Lys  Gly  Val  Ile  Val  His  Arg  Leu  Glu
285                           290                           295                 300

GGG  GTC  TCG  TAC  AAC  ATA  GGC  TCT  CAA  GAG  TGG  TAT  ACC  ACT  GTG  CCC      963
Gly  Val  Ser  Tyr  Asn  Ile  Gly  Ser  Gln  Glu  Trp  Tyr  Thr  Thr  Val  Pro
                         305                           310                     315

AAG  TAT  GTT  GCA  ACC  CAA  GGG  TAC  CTT  ATC  TCG  AAT  TTT  GAT  GAG  TCA     1011
Lys  Tyr  Val  Ala  Thr  Gln  Gly  Tyr  Leu  Ile  Ser  Asn  Phe  Asp  Glu  Ser
               320                           325                      330

TCG  TGT  ACT  TTC  ATG  CCA  GAG  GGG  ACT  GTG  TGC  AGC  CAA  AAT  GCC  TTG     1059
Ser  Cys  Thr  Phe  Met  Pro  Glu  Gly  Thr  Val  Cys  Ser  Gln  Asn  Ala  Leu
          335                           340                      345

TAC  CCG  ATG  AGT  CCT  CTG  CTC  CAA  GAA  TGC  CTC  CGG  GGG  TAC  ACC  AAG     1107
Tyr  Pro  Met  Ser  Pro  Leu  Leu  Gln  Glu  Cys  Leu  Arg  Gly  Tyr  Thr  Lys
     350                      355                      360

TCC  TGT  GCT  CGT  ACA  CTC  GTA  TCC  GGG  TCT  TTT  GGG  AAC  CGG  TTC  ATT     1155
Ser  Cys  Ala  Arg  Thr  Leu  Val  Ser  Gly  Ser  Phe  Gly  Asn  Arg  Phe  Ile
365                      370                      375                           380

TTA  TCA  CAA  GGG  AAC  CTA  ATA  GCC  AAT  TGT  GCA  TCA  ATC  CTT  TGC  AAG     1203
Leu  Ser  Gln  Gly  Asn  Leu  Ile  Ala  Asn  Cys  Ala  Ser  Ile  Leu  Cys  Lys
                         385                      390                      395

TGT  TAC  ACA  ACA  GGA  ACG  ATC  ATT  AAT  CAA  GAC  CCT  GAC  AAG  ATC  CTA     1251
Cys  Tyr  Thr  Thr  Gly  Thr  Ile  Ile  Asn  Gln  Asp  Pro  Asp  Lys  Ile  Leu
               400                      405                      410

ACA  TAC  ATT  GCT  GCC  GAT  CAC  TGC  CCG  GTA  GTC  GAG  GTG  AAC  GGC  GTG     1299
Thr  Tyr  Ile  Ala  Ala  Asp  His  Cys  Pro  Val  Val  Glu  Val  Asn  Gly  Val
          415                      420                      425

ACC  ATC  CAA  GTC  GGG  AGC  AGG  AGG  TAT  CCA  GAC  GCT  GTG  TAC  TTG  CAC     1347
Thr  Ile  Gln  Val  Gly  Ser  Arg  Arg  Tyr  Pro  Asp  Ala  Val  Tyr  Leu  His
     430                      435                      440

AGA  ATT  GAC  CTC  GGT  CCT  CCC  ATA  TCA  TTG  GAG  AGG  TTG  GAC  GTA  GGG     1395
Arg  Ile  Asp  Leu  Gly  Pro  Pro  Ile  Ser  Leu  Glu  Arg  Leu  Asp  Val  Gly
445                      450                      455                           460

ACA  AAT  CTG  GGG  AAT  GCA  ATT  GCT  AAG  TTG  GAG  GAT  GCC  AAG  GAA  TTG     1443
Thr  Asn  Leu  Gly  Asn  Ala  Ile  Ala  Lys  Leu  Glu  Asp  Ala  Lys  Glu  Leu
                    465                      470                           475

TTG  GAG  TCA  TCG  GAC  CAG  ATA  TTG  AGG  AGT  ATG  AAA  GGT  TTA  TCG  AGC     1491
Leu  Glu  Ser  Ser  Asp  Gln  Ile  Leu  Arg  Ser  Met  Lys  Gly  Leu  Ser  Ser
               480                      485                           490

ACT  AGC  ATA  GTC  TAC  ATC  CTG  ATT  GCA  GTG  TGT  CTT  GGA  GGG  TTG  ATA     1539
Thr  Ser  Ile  Val  Tyr  Ile  Leu  Ile  Ala  Val  Cys  Leu  Gly  Gly  Leu  Ile
          495                      500                      505

GGG  ATC  CCC  GCT  TTA  ATA  TGT  TGC  TGC  AGG  GGG  CGT  TGT  AAC  AAA  AAG     1587
Gly  Ile  Pro  Ala  Leu  Ile  Cys  Cys  Cys  Arg  Gly  Arg  Cys  Asn  Lys  Lys
     510                      515                      520

GGA  GAA  CAA  GTT  GGT  ATG  TCA  AGA  CCA  GGC  CTA  AAG  CCT  GAT  CTT  ACG     1635
Gly  Glu  Gln  Val  Gly  Met  Ser  Arg  Pro  Gly  Leu  Lys  Pro  Asp  Leu  Thr
525                      530                      535                           540

GGA  ACA  TCA  AAA  TCC  TAT  GTA  AGG  TCG  CTC  TGATCCTCTA  CAACTCTTGA           1685
Gly  Thr  Ser  Lys  Ser  Tyr  Val  Arg  Ser  Leu
               545                      550

AA                                                                                 1687
```

( 2 ) INFORMATION FOR SEQ ID NO:16:

( i ) SEQUENCE CHARACTERISTICS:
        ( A ) LENGTH: 550 amino acids
        ( B ) TYPE: amino acid
        ( D ) TOPOLOGY: linear ( i ) MOLECULE TYPE: protein ( x i ) SEQUENCE DESCRIPTION: SEQ ID NO:16:

| Met | Gly | Leu | Lys | Val | Asn | Val | Ser | Ala | Ile | Phe | Met | Ala | Val | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Thr Leu Gln Thr Pro Thr Gly Gln Ile His Trp Gly Asn Leu Ser Lys
                20                    25                    30

Ile Gly Val Val Gly Ile Gly Ser Ala Ser Tyr Lys Val Met Thr Arg
            35                40                    45

Ser Ser His Gln Ser Leu Val Ile Lys Leu Met Pro Asn Ile Thr Leu
        50                55                60

Leu Asn Asn Cys Thr Arg Val Glu Ile Ala Glu Tyr Arg Arg Leu Leu
65                  70                  75                      80

Arg Thr Val Leu Glu Pro Ile Arg Asp Ala Leu Asn Ala Met Thr Gln
                85                  90                  95

Asn Ile Arg Pro Val Gln Ser Val Ala Ser Ser Arg Arg His Lys Arg
            100                 105                 110

Phe Ala Gly Val Val Leu Ala Gly Ala Ala Leu Gly Val Ala Thr Ala
        115                 120                 125

Ala Gln Ile Thr Ala Gly Ile Ala Leu His Gln Ser Met Leu Asn Ser
    130                 135                 140

Gln Ala Ile Asp Asn Leu Arg Ala Ser Leu Glu Thr Thr Asn Gln Ala
145                 150                 155                 160

Ile Glu Thr Ile Arg Gln Ala Gly Gln Glu Met Ile Leu Ala Val Gln
                165                 170                 175

Gly Val Gln Asp Tyr Ile Asn Asn Glu Leu Ile Pro Ser Met Asn Gln
            180                 185                 190

Leu Ser Cys Asp Leu Ile Gly Gln Lys Leu Gly Leu Lys Leu Leu Arg
        195                 200                 205

Tyr Tyr Thr Glu Ile Leu Ser Leu Phe Gly Pro Ser Leu Arg Asp Pro
210                 215                 220

Ile Ser Ala Glu Ile Ser Ile Gln Ala Leu Ser Tyr Ala Leu Gly Gly
225                 230                 235                 240

Asp Ile Asn Lys Val Leu Glu Lys Leu Gly Tyr Ser Gly Gly Asp Leu
                245                 250                 255

Leu Gly Ile Leu Glu Ser Gly Gly Ile Lys Ala Arg Ile Thr His Val
            260                 265                 270

Asp Thr Glu Ser Tyr Phe Ile Val Leu Ser Ile Ala Tyr Pro Thr Leu
    275                 280                 285

Ser Glu Ile Lys Gly Val Ile His Arg Leu Glu Gly Val Ser Tyr
    290                 295                 300

Asn Ile Gly Ser Gln Glu Trp Tyr Thr Thr Val Pro Lys Tyr Val Ala
305                 310                 315                 320

Thr Gln Gly Tyr Leu Ile Ser Asn Phe Asp Glu Ser Ser Cys Thr Phe
                325                 330                 335

Met Pro Glu Gly Thr Val Cys Ser Gln Asn Ala Leu Tyr Pro Met Ser
            340                 345                 350

Pro Leu Leu Gln Glu Cys Leu Arg Gly Tyr Thr Lys Ser Cys Ala Arg
        355                 360                 365

Thr Leu Val Ser Gly Ser Phe Gly Asn Arg Phe Ile Leu Ser Gln Gly
    370                 375                 380

Asn Leu Ile Ala Asn Cys Ala Ser Ile Leu Cys Lys Cys Tyr Thr Thr
385                 390                 395                 400

Gly Thr Ile Ile Asn Gln Asp Pro Asp Lys Ile Leu Thr Tyr Ile Ala
                405                 410                 415

| | | | | | | | | | | | | | | |
|---|---|---|---|---|---|---|---|---|---|---|---|---|---|---|
| Ala | Asp | His | Cys<br>420 | Pro | Val | Val | Glu<br>425 | Val | Asn | Gly | Val | Thr | Ile<br>430 | Gln | Val |
| Gly | Ser | Arg<br>435 | Arg | Tyr | Pro | Asp<br>440 | Ala | Val | Tyr | Leu | His | Arg<br>445 | Ile | Asp | Leu |
| Gly | Pro<br>450 | Pro | Ile | Ser | Leu | Glu<br>455 | Arg | Leu | Asp | Val | Gly<br>460 | Thr | Asn | Leu | Gly |
| Asn<br>465 | Ala | Ile | Ala | Lys | Leu<br>470 | Glu | Asp | Ala | Lys | Glu<br>475 | Leu | Leu | Glu | Ser | Ser<br>480 |
| Asp | Gln | Ile | Leu | Arg<br>485 | Ser | Met | Lys | Gly | Leu<br>490 | Ser | Ser | Thr | Ser | Ile<br>495 | Val |
| Tyr | Ile | Leu | Ile<br>500 | Ala | Val | Cys | Leu | Gly<br>505 | Gly | Leu | Ile | Gly<br>510 | Ile | Pro | Ala |
| Leu | Ile | Cys<br>515 | Cys | Cys | Arg | Gly | Arg<br>520 | Cys | Asn | Lys | Lys | Gly<br>525 | Glu | Gln | Val |
| Gly | Met<br>530 | Ser | Arg | Pro | Gly | Leu<br>535 | Lys | Pro | Asp | Leu | Thr<br>540 | Gly | Thr | Ser | Lys |
| Ser<br>545 | Tyr | Val | Arg | Ser | Leu<br>550 | | | | | | | | | | |

(2) INFORMATION FOR SEQ ID NO:17:

(i) SEQUENCE CHARACTERISTICS:
        (A) LENGTH: 1687 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (B) STRAIN: San Diego f (ix) FEATURE:
        (A) NAME/KEY: CDS
        (B) LOCATION: 16..1668

(xi) SEQUENCE DESCRIPTION: SEQ ID NO:17:

| | | | | | | | | | | | | | |
|---|---|---|---|---|---|---|---|---|---|---|---|---|---|
| CATCCAGTGT | CCATC | ATG<br>Met<br>1 | GGT<br>Gly | CTC<br>Leu | AAG<br>Lys | GTG<br>Val<br>5 | AAC<br>Asn | GTC<br>Val | TTT<br>Phe | GCC<br>Ala | ATA<br>Ile | TTC<br>Phe<br>10 | ATG<br>Met | 51 |
| GCA<br>Ala | GTA<br>Val | CTG<br>Leu<br>15 | TTA<br>Leu | ACT<br>Thr | CTC<br>Leu | CAA<br>Gln | ACA<br>Thr<br>20 | CCC<br>Pro | ACC<br>Thr | GGT<br>Gly | CAA<br>Gln | ATC<br>Ile<br>25 | CAT<br>His | TGG<br>Trp | GGC<br>Gly | 99 |
| AAT<br>Asn | CTC<br>Leu | TCT<br>Ser<br>30 | AAG<br>Lys | ATA<br>Ile | GGG<br>Gly | GTG<br>Val | GTA<br>Val<br>35 | GGG<br>Gly | ATA<br>Ile | GGA<br>Gly | AGT<br>Ser | GCA<br>Ala<br>40 | AGC<br>Ser | TAC<br>Tyr | AAA<br>Lys | 147 |
| GTT<br>Val<br>45 | ATG<br>Met | ACT<br>Thr | CGT<br>Arg | TCC<br>Ser | AGC<br>Ser<br>50 | CAT<br>His | CAA<br>Gln | TCA<br>Ser | TTG<br>Leu | GTC<br>Val<br>55 | ATA<br>Ile | AAA<br>Lys | TTA<br>Leu | ATG<br>Met | CCC<br>Pro<br>60 | 195 |
| AAT<br>Asn | ATA<br>Ile | ACT<br>Thr | CTC<br>Leu | CTC<br>Leu<br>65 | AAT<br>Asn | AAC<br>Asn | TGC<br>Cys | ACG<br>Thr | AGG<br>Arg<br>70 | GTA<br>Val | GAG<br>Glu | ATT<br>Ile | GCA<br>Ala | GAA<br>Glu<br>75 | TAC<br>Tyr | 243 |
| AGG<br>Arg | AGA<br>Arg | CTA<br>Leu | CTG<br>Leu<br>80 | AGA<br>Arg | ACA<br>Thr | GTT<br>Val | TTG<br>Leu | GAA<br>Glu<br>85 | CCA<br>Pro | ATT<br>Ile | AGA<br>Arg | GAT<br>Asp | GCA<br>Ala<br>90 | CTT<br>Leu | AAT<br>Asn | 291 |
| GCA<br>Ala | ATG<br>Met | ACC<br>Thr<br>95 | CAG<br>Gln | AAT<br>Asn | ATA<br>Ile | AGA<br>Arg | CCG<br>Pro<br>100 | GTT<br>Val | CAG<br>Gln | AGT<br>Ser | GTA<br>Val | GCT<br>Ala<br>105 | TCA<br>Ser | AGT<br>Ser | AGG<br>Arg | 339 |
| AGA<br>Arg | CAC<br>His | AAG<br>Lys<br>110 | AGA<br>Arg | TTT<br>Phe | GCG<br>Ala | GGA<br>Gly | GTA<br>Val<br>115 | GTC<br>Val | CTG<br>Leu | GCA<br>Ala | GGT<br>Gly | GCG<br>Ala<br>120 | GCC<br>Ala | CTA<br>Leu | GGC<br>Gly | 387 |
| GTT<br>Val | GCC<br>Ala | ACA<br>Thr | GCT<br>Ala | GCT<br>Ala | CAG<br>Gln | ATA<br>Ile | ACA<br>Thr | GCC<br>Ala | GGC<br>Gly | ATT<br>Ile | GCA<br>Ala | CTT<br>Leu | CAC<br>His | CAG<br>Gln | TCC<br>Ser | 435 |

| | | | | | | | | | | | | | | | | |
|---|---|---|---|---|---|---|---|---|---|---|---|---|---|---|---|---|
| Val | Ala | Thr | Ala | Ala | Gln | Ile | Thr | Ala | Gly | Ile | Ala | Leu | His | Gln | Ser | |
| 125 | | | | | 130 | | | | 135 | | | | | | 140 | |
| ATG | CTG | AAC | TCT | CAA | GCC | ATC | GAC | AAT | CTG | AGA | GCA | AGC | CTG | GAA | ACT | 483 |
| Met | Leu | Asn | Ser | Gln | Ala | Ile | Asp | Asn | Leu | Arg | Ala | Ser | Leu | Glu | Thr | |
| | | | | 145 | | | | | 150 | | | | | 155 | | |
| ACT | AAT | CAG | GCA | ATT | GAG | GCA | ATC | AGA | CAA | GCA | GGG | CAG | GAG | ATG | ATA | 531 |
| Thr | Asn | Gln | Ala | Ile | Glu | Ala | Ile | Arg | Gln | Ala | Gly | Gln | Glu | Met | Ile | |
| | | | 160 | | | | | 165 | | | | | 170 | | | |
| TTG | GCT | GTT | CAG | GGT | GTC | CAA | GAC | TAC | ATC | AAT | AAT | GAG | CTG | ATA | CCG | 579 |
| Leu | Ala | Val | Gln | Gly | Val | Gln | Asp | Tyr | Ile | Asn | Asn | Glu | Leu | Ile | Pro | |
| | | 175 | | | | | 180 | | | | | 185 | | | | |
| TCT | ATG | AAC | CAA | CTA | TCT | TGT | GAT | TTA | ATC | GGC | CAG | AAG | CTA | GGG | CTC | 627 |
| Ser | Met | Asn | Gln | Leu | Ser | Cys | Asp | Leu | Ile | Gly | Gln | Lys | Leu | Gly | Leu | |
| | 190 | | | | 195 | | | | | 200 | | | | | | |
| AAA | TTG | CTC | AGA | TAC | TAT | ACA | GAA | ATC | CTG | TCA | TTA | TTT | GGC | CCC | AGC | 675 |
| Lys | Leu | Leu | Arg | Tyr | Tyr | Thr | Glu | Ile | Leu | Ser | Leu | Phe | Gly | Pro | Ser | |
| 205 | | | | | 210 | | | | | 215 | | | | | 220 | |
| TTA | CGG | GAC | CCC | ATA | TCT | GCG | GAG | ATA | TCC | ATC | CAG | GCT | TTG | AGC | TAT | 723 |
| Leu | Arg | Asp | Pro | Ile | Ser | Ala | Glu | Ile | Ser | Ile | Gln | Ala | Leu | Ser | Tyr | |
| | | | | 225 | | | | | 230 | | | | | 235 | | |
| GCG | CTT | GGG | GGA | GAT | ATC | AAT | AAG | GTA | TTA | GAA | AAG | CTC | GGA | TAC | AGT | 771 |
| Ala | Leu | Gly | Gly | Asp | Ile | Asn | Lys | Val | Leu | Glu | Lys | Leu | Gly | Tyr | Ser | |
| | | | 240 | | | | | 245 | | | | | 250 | | | |
| GGA | GGT | GAT | TTA | CTG | GGC | ATC | TTA | GAG | AGC | AGA | GGA | ATA | AAG | GCC | CGG | 819 |
| Gly | Gly | Asp | Leu | Leu | Gly | Ile | Leu | Glu | Ser | Arg | Gly | Ile | Lys | Ala | Arg | |
| | | 255 | | | | | 260 | | | | | 265 | | | | |
| ATA | ACT | CAC | GTC | GAC | ACA | GAG | TCC | TAC | TTC | ATT | GTC | CTC | AGT | ATA | GCC | 867 |
| Ile | Thr | His | Val | Asp | Thr | Glu | Ser | Tyr | Phe | Ile | Val | Leu | Ser | Ile | Ala | |
| | 270 | | | | 275 | | | | | 280 | | | | | | |
| TAT | CCG | ACG | CTG | TCC | GAG | ATT | AAG | GGG | GTG | ATT | GTC | CAC | CGG | CTA | GAG | 915 |
| Tyr | Pro | Thr | Leu | Ser | Glu | Ile | Lys | Gly | Val | Ile | Val | His | Arg | Leu | Glu | |
| 285 | | | | | 290 | | | | | 295 | | | | | 300 | |
| GGG | GTC | TCG | TAC | AAT | ATA | GGC | TCT | CAA | GAG | TGG | TAT | ACC | ACT | GTG | CCC | 963 |
| Gly | Val | Ser | Tyr | Asn | Ile | Gly | Ser | Gln | Glu | Trp | Tyr | Thr | Thr | Val | Pro | |
| | | | | 305 | | | | 310 | | | | | 315 | | | |
| AAG | TAT | GTT | GCA | ACC | CAA | GGG | TAC | CTT | ATC | TCG | AAT | TTT | GAT | GAG | TCA | 1011 |
| Lys | Tyr | Val | Ala | Thr | Gln | Gly | Tyr | Leu | Ile | Ser | Asn | Phe | Asp | Glu | Ser | |
| | | | 320 | | | | 325 | | | | | 330 | | | | |
| TCG | TGT | ACT | TTC | ATG | CCA | GAG | GGG | ACT | GTG | TGC | AGC | CAA | AAT | GCC | TTG | 1059 |
| Ser | Cys | Thr | Phe | Met | Pro | Glu | Gly | Thr | Val | Cys | Ser | Gln | Asn | Ala | Leu | |
| | | 335 | | | | | 340 | | | | | 345 | | | | |
| TAC | CCG | ATG | AGT | CCT | CTG | CTC | CAA | GAA | TGC | CTC | CGG | GGG | TCC | ACC | AAG | 1107 |
| Tyr | Pro | Met | Ser | Pro | Leu | Leu | Gln | Glu | Cys | Leu | Arg | Gly | Ser | Thr | Lys | |
| | 350 | | | | 355 | | | | | 360 | | | | | | |
| TCC | TGT | GCT | CGT | ACA | CTC | GTA | TCC | GGG | TCT | TTT | GGG | AAC | CGG | TTC | ATT | 1155 |
| Ser | Cys | Ala | Arg | Thr | Leu | Val | Ser | Gly | Ser | Phe | Gly | Asn | Arg | Phe | Ile | |
| 365 | | | | 370 | | | | | 375 | | | | | 380 | | |
| TTA | TCA | CAA | GGG | AAC | CTA | ATA | GCC | AAT | TGT | GCA | TCA | ATC | CTC | TGC | AAG | 1203 |
| Leu | Ser | Gln | Gly | Asn | Leu | Ile | Ala | Asn | Cys | Ala | Ser | Ile | Leu | Cys | Lys | |
| | | | 385 | | | | 390 | | | | | 395 | | | | |
| TGT | TAC | ACA | ACA | GGA | ACG | ATC | ATT | AAT | CAA | GAC | CCT | GAC | AAG | ATC | CTA | 1251 |
| Cys | Tyr | Thr | Thr | Gly | Thr | Ile | Ile | Asn | Gln | Asp | Pro | Asp | Lys | Ile | Leu | |
| | | | 400 | | | | 405 | | | | | 410 | | | | |
| ACA | TAC | ATT | GCT | GCC | GAT | CAC | TGC | CCG | GTA | GTC | GAG | GTG | AAC | GGT | GTG | 1299 |
| Thr | Tyr | Ile | Ala | Ala | Asp | His | Cys | Pro | Val | Val | Glu | Val | Asn | Gly | Val | |
| | | 415 | | | | 420 | | | | | 425 | | | | | |
| ACC | ATC | CAA | GTC | GGG | AGC | AGG | AGG | TAT | CCG | GAC | GCG | GTG | TAC | CTG | CAC | 1347 |
| Thr | Ile | Gln | Val | Gly | Ser | Arg | Arg | Tyr | Pro | Asp | Ala | Val | Tyr | Leu | His | |
| | | 430 | | | | 435 | | | | | 440 | | | | | |
| AGA | ATT | GAC | CTC | GGT | CCT | CCC | ATA | TCA | TTG | GAG | AAG | TTG | GAC | GTA | GGG | 1395 |

| | | | | | | | | | | | | | | | | |
|---|---|---|---|---|---|---|---|---|---|---|---|---|---|---|---|---|
| Arg | Ile | Asp | Leu | Gly | Pro | Pro | Ile | Ser | Leu | Glu | Lys | Leu | Asp | Val | Gly | |
| 445 | | | | 450 | | | | | 455 | | | | | | 460 | |

| ACA | AAT | CTG | GGG | AAT | GCA | ATT | GCT | AAG | CTG | GAG | GAT | GCC | AAG | GAA | TTG | 1443 |
|---|---|---|---|---|---|---|---|---|---|---|---|---|---|---|---|---|
| Thr | Asn | Leu | Gly | Asn | Ala | Ile | Ala | Lys | Leu | Glu | Asp | Ala | Lys | Glu | Leu | |
| | | | | 465 | | | | | 470 | | | | | 475 | | |

| CTG | GAG | TCA | TCG | GAC | CAG | ATA | TTG | AGG | AGT | ATG | AAA | GGT | TTA | TCG | AGC | 1491 |
|---|---|---|---|---|---|---|---|---|---|---|---|---|---|---|---|---|
| Leu | Glu | Ser | Ser | Asp | Gln | Ile | Leu | Arg | Ser | Met | Lys | Gly | Leu | Ser | Ser | |
| | | | 480 | | | | | 485 | | | | | 490 | | | |

| ACT | AGC | ATA | GTT | TAC | ATC | CTG | ATT | GCA | GTG | TGT | CTT | GGA | GGG | TTG | ATA | 1539 |
|---|---|---|---|---|---|---|---|---|---|---|---|---|---|---|---|---|
| Thr | Ser | Ile | Val | Tyr | Ile | Leu | Ile | Ala | Val | Cys | Leu | Gly | Gly | Leu | Ile | |
| | | 495 | | | | | 500 | | | | | 505 | | | | |

| GGG | ATC | CCC | GCT | TTA | ATA | TGT | TGC | TGC | AGG | GGG | CGC | TGT | AAC | AAA | AAG | 1587 |
|---|---|---|---|---|---|---|---|---|---|---|---|---|---|---|---|---|
| Gly | Ile | Pro | Ala | Leu | Ile | Cys | Cys | Cys | Arg | Gly | Arg | Cys | Asn | Lys | Lys | |
| 510 | | | | | 515 | | | | | 520 | | | | | | |

| GGA | GAA | CAA | GTT | GGT | ATG | TCA | AGA | CCA | GGC | CTA | AAG | CCT | GAT | CTT | ACA | 1635 |
|---|---|---|---|---|---|---|---|---|---|---|---|---|---|---|---|---|
| Gly | Glu | Gln | Val | Gly | Met | Ser | Arg | Pro | Gly | Leu | Lys | Pro | Asp | Leu | Thr | |
| 525 | | | | 530 | | | | | 535 | | | | | 540 | | |

| GGG | ACA | TCA | AAA | TCC | TAT | GTA | AGG | TCG | CTC | TGATCCCCTA | CAACTCTTGA | | | | | 1685 |
|---|---|---|---|---|---|---|---|---|---|---|---|---|---|---|---|---|
| Gly | Thr | Ser | Lys | Ser | Tyr | Val | Arg | Ser | Leu | | | | | | | |
| | | | | 545 | | | | | 550 | | | | | | | |

| AA | | | | | | | | | | | | | | | | 1687 |
|---|---|---|---|---|---|---|---|---|---|---|---|---|---|---|---|---|

( 2 ) INFORMATION FOR SEQ ID NO:18:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| | | | | | | | | | | | | | | |
|---|---|---|---|---|---|---|---|---|---|---|---|---|---|---|
| Met | Gly | Leu | Lys | Val | Asn | Val | Phe | Ala | Ile | Phe | Met | Ala | Val | Leu | Leu |
| 1 | | | | 5 | | | | | 10 | | | | | 15 | |
| Thr | Leu | Gln | Thr | Pro | Thr | Gly | Gln | Ile | His | Trp | Gly | Asn | Leu | Ser | Lys |
| | | | 20 | | | | | 25 | | | | | 30 | | |
| Ile | Gly | Val | Val | Gly | Ile | Gly | Ser | Ala | Ser | Tyr | Lys | Val | Met | Thr | Arg |
| | | | 35 | | | | | 40 | | | | | 45 | | |
| Ser | Ser | His | Gln | Ser | Leu | Val | Ile | Lys | Leu | Met | Pro | Asn | Ile | Thr | Leu |
| | 50 | | | | | 55 | | | | | 60 | | | | |
| Leu | Asn | Asn | Cys | Thr | Arg | Val | Glu | Ile | Ala | Glu | Tyr | Arg | Arg | Leu | Leu |
| 65 | | | | | 70 | | | | | 75 | | | | | 80 |
| Arg | Thr | Val | Leu | Glu | Pro | Ile | Arg | Asp | Ala | Leu | Asn | Ala | Met | Thr | Gln |
| | | | | 85 | | | | | 90 | | | | | 95 | |
| Asn | Ile | Arg | Pro | Val | Gln | Ser | Val | Ala | Ser | Ser | Arg | Arg | His | Lys | Arg |
| | | | 100 | | | | | 105 | | | | | 110 | | |
| Phe | Ala | Gly | Val | Val | Leu | Ala | Gly | Ala | Ala | Leu | Gly | Val | Ala | Thr | Ala |
| | | | 115 | | | | | 120 | | | | | 125 | | |
| Ala | Gln | Ile | Thr | Ala | Gly | Ile | Ala | Leu | His | Gln | Ser | Met | Leu | Asn | Ser |
| | 130 | | | | | 135 | | | | | 140 | | | | |
| Gln | Ala | Ile | Asp | Asn | Leu | Arg | Ala | Ser | Leu | Glu | Thr | Thr | Asn | Gln | Ala |
| 145 | | | | | 150 | | | | | 155 | | | | | 160 |
| Ile | Glu | Ala | Ile | Arg | Gln | Ala | Gly | Gln | Glu | Met | Ile | Leu | Ala | Val | Gln |
| | | | | 165 | | | | | 170 | | | | | 175 | |
| Gly | Val | Gln | Asp | Tyr | Ile | Asn | Asn | Glu | Leu | Ile | Pro | Ser | Met | Asn | Gln |
| | | | 180 | | | | | 185 | | | | | 190 | | |
| Leu | Ser | Cys | Asp | Leu | Ile | Gly | Gln | Lys | Leu | Gly | Leu | Lys | Leu | Leu | Arg |
| | | 195 | | | | | 200 | | | | | 205 | | | |

| Tyr | Tyr | Thr | Glu | Ile | Leu | Ser | Leu | Phe | Gly | Pro | Ser | Leu | Arg | Asp | Pro |
|---|---|---|---|---|---|---|---|---|---|---|---|---|---|---|---|
| | 210 | | | | 215 | | | | | 220 | | | | | |
| Ile | Ser | Ala | Glu | Ile | Ser | Ile | Gln | Ala | Leu | Ser | Tyr | Ala | Leu | Gly | Gly |
| 225 | | | | 230 | | | | | 235 | | | | | | 240 |
| Asp | Ile | Asn | Lys | Val | Leu | Glu | Lys | Leu | Gly | Tyr | Ser | Gly | Gly | Asp | Leu |
| | | | | 245 | | | | | 250 | | | | | 255 | |
| Leu | Gly | Ile | Leu | Glu | Ser | Arg | Gly | Ile | Lys | Ala | Arg | Ile | Thr | His | Val |
| | | | 260 | | | | | 265 | | | | | 270 | | |
| Asp | Thr | Glu | Ser | Tyr | Phe | Ile | Val | Leu | Ser | Ile | Ala | Tyr | Pro | Thr | Leu |
| | | 275 | | | | | 280 | | | | | 285 | | | |
| Ser | Glu | Ile | Lys | Gly | Val | Ile | Val | His | Arg | Leu | Glu | Gly | Val | Ser | Tyr |
| | 290 | | | | | 295 | | | | | 300 | | | | |
| Asn | Ile | Gly | Ser | Gln | Glu | Trp | Tyr | Thr | Thr | Val | Pro | Lys | Tyr | Val | Ala |
| 305 | | | | | 310 | | | | | 315 | | | | | 320 |
| Thr | Gln | Gly | Tyr | Leu | Ile | Ser | Asn | Phe | Asp | Glu | Ser | Ser | Cys | Thr | Phe |
| | | | | 325 | | | | | 330 | | | | | 335 | |
| Met | Pro | Glu | Gly | Thr | Val | Cys | Ser | Gln | Asn | Ala | Leu | Tyr | Pro | Met | Ser |
| | | | 340 | | | | | 345 | | | | | 350 | | |
| Pro | Leu | Leu | Gln | Glu | Cys | Leu | Arg | Gly | Ser | Thr | Lys | Ser | Cys | Ala | Arg |
| | | 355 | | | | | 360 | | | | | 365 | | | |
| Thr | Leu | Val | Ser | Gly | Ser | Phe | Gly | Asn | Arg | Phe | Ile | Leu | Ser | Gln | Gly |
| | 370 | | | | | 375 | | | | | 380 | | | | |
| Asn | Leu | Ile | Ala | Asn | Cys | Ala | Ser | Ile | Leu | Cys | Lys | Cys | Tyr | Thr | Thr |
| 385 | | | | | 390 | | | | | 395 | | | | | 400 |
| Gly | Thr | Ile | Ile | Asn | Gln | Asp | Pro | Asp | Lys | Ile | Leu | Thr | Tyr | Ile | Ala |
| | | | | 405 | | | | | 410 | | | | | 415 | |
| Ala | Asp | His | Cys | Pro | Val | Val | Glu | Val | Asn | Gly | Val | Thr | Ile | Gln | Val |
| | | | 420 | | | | | 425 | | | | | 430 | | |
| Gly | Ser | Arg | Arg | Tyr | Pro | Asp | Ala | Val | Tyr | Leu | His | Arg | Ile | Asp | Leu |
| | | 435 | | | | | 440 | | | | | 445 | | | |
| Gly | Pro | Pro | Ile | Ser | Leu | Glu | Lys | Leu | Asp | Val | Gly | Thr | Asn | Leu | Gly |
| | 450 | | | | | 455 | | | | | 460 | | | | |
| Asn | Ala | Ile | Ala | Lys | Leu | Glu | Asp | Ala | Lys | Glu | Leu | Leu | Glu | Ser | Ser |
| 465 | | | | | 470 | | | | | 475 | | | | | 480 |
| Asp | Gln | Ile | Leu | Arg | Ser | Met | Lys | Gly | Leu | Ser | Ser | Thr | Ser | Ile | Val |
| | | | | 485 | | | | | 490 | | | | | 495 | |
| Tyr | Ile | Leu | Ile | Ala | Val | Cys | Leu | Gly | Gly | Leu | Ile | Gly | Ile | Pro | Ala |
| | | | 500 | | | | | 505 | | | | | 510 | | |
| Leu | Ile | Cys | Cys | Cys | Arg | Gly | Arg | Cys | Asn | Lys | Lys | Gly | Glu | Gln | Val |
| | | 515 | | | | | 520 | | | | | 525 | | | |
| Gly | Met | Ser | Arg | Pro | Gly | Leu | Lys | Pro | Asp | Leu | Thr | Gly | Thr | Ser | Lys |
| | 530 | | | | | 535 | | | | | 540 | | | | |
| Ser | Tyr | Val | Arg | Ser | Leu | | | | | | | | | | |
| 545 | | | | | 550 | | | | | | | | | | |

( 2 ) INFORMATION FOR SEQ ID NO:19:

( i ) SEQUENCE CHARACTERISTICS:
        ( A ) LENGTH: 1687 base pairs
        ( B ) TYPE: nucleic acid
        ( C ) STRANDEDNESS: double
        ( D ) TOPOLOGY: linear ( i i ) MOLECULE TYPE: DNA (genomic)

( v i ) ORIGINAL SOURCE:
        ( B ) STRAIN: Chicago 1 f ( i x ) FEATURE:
   ( A ) NAME/KEY: CDS
   ( B ) LOCATION: 16..1668

( x i ) SEQUENCE DESCRIPTION: SEQ ID NO:19:

```
CATCCAGTGT CCATC ATG GGT CTC AAG GTG AAC GTC TTT GCC ATA TTC ATG        51
                 Met Gly Leu Lys Val Asn Val Phe Ala Ile Phe Met
                  1               5                      10

GCA GTA CTG TTA ACT CTC CAA ACA CCC ACC GGT CAA ATC CAT TGG GGC          99
Ala Val Leu Leu Thr Leu Gln Thr Pro Thr Gly Gln Ile His Trp Gly
         15                  20                  25

AAT CTC TCT AAG ATA GGG GTG GTA GGG ATA GGA AGT GCA AGC TAC AAA         147
Asn Leu Ser Lys Ile Gly Val Val Gly Ile Gly Ser Ala Ser Tyr Lys
             30                  35                  40

GTT ATG ACT CGT TCC AGC CAT CAA TCA TTG GTC ATA AAA TTA ATG CCC         195
Val Met Thr Arg Ser Ser His Gln Ser Leu Val Ile Lys Leu Met Pro
 45                  50                  55                  60

AAT ATA ACT CTC CTC AAT AAC TGC ACG AGG GTA GAG ATT GCA GAA TAC         243
Asn Ile Thr Leu Leu Asn Asn Cys Thr Arg Val Glu Ile Ala Glu Tyr
                 65                  70                  75

AGG AGA CTA CTG AGA ACA GTT TTG GAA CCA ATT AGA GAT GCA CTT AAT         291
Arg Arg Leu Leu Arg Thr Val Leu Glu Pro Ile Arg Asp Ala Leu Asn
             80                  85                  90

GCA ATG ACC CAG AAT ATA AGA CCG GTT CAG AGT GTA GCT TCA AGT AGG         339
Ala Met Thr Gln Asn Ile Arg Pro Val Gln Ser Val Ala Ser Ser Arg
         95                 100                 105

AGA CAC AAG AGA TTT GCG GGA GTA GTC CTG GCA GGT GCG GCC CTA GGC         387
Arg His Lys Arg Phe Ala Gly Val Val Leu Ala Gly Ala Ala Leu Gly
    110                 115                 120

GTT GCC ACA GCT GCT CAG ATA ACA GCC GGC ATT GCA CTT CAC CAG TCC         435
Val Ala Thr Ala Ala Gln Ile Thr Ala Gly Ile Ala Leu His Gln Ser
125                 130                 135                 140

ATG CTG AAC TCT CAA GCC ATC GAC AAT CTG AGA GCA AGC CTG GAA ACT         483
Met Leu Asn Ser Gln Ala Ile Asp Asn Leu Arg Ala Ser Leu Glu Thr
                145                 150                 155

ACT AAT CAG GCA ATT GAG GCA ATC AGA CAA GCA GGG CAG GAG ATG ATA         531
Thr Asn Gln Ala Ile Glu Ala Ile Arg Gln Ala Gly Gln Glu Met Ile
            160                 165                 170

TTG GCT GTT CAG GGT GTC CAA GAC TAC ATC AAT AAT GAG CTG ATA CCG         579
Leu Ala Val Gln Gly Val Gln Asp Tyr Ile Asn Asn Glu Leu Ile Pro
        175                 180                 185

TCT ATG AAC CAA CTA TCT TGT GAT TTA ATC GGC CAG AAG CTA GGG CTC         627
Ser Met Asn Gln Leu Ser Cys Asp Leu Ile Gly Gln Lys Leu Gly Leu
    190                 195                 200

AAA TTG CTC AGA TAC TAT ACA GAA ATC CTG TCA TTA TTT GGC CCC AGC         675
Lys Leu Leu Arg Tyr Tyr Thr Glu Ile Leu Ser Leu Phe Gly Pro Ser
205                 210                 215                 220

TTA CGG GAC CCC ATA TCT GCG GAG ATA TCC ATC CAG GCT TTG AGC TAT         723
Leu Arg Asp Pro Ile Ser Ala Glu Ile Ser Ile Gln Ala Leu Ser Tyr
                225                 230                 235

GCG CTT GGG GGA GAT ATC AAT AAG GTA TTA GAA AAG CTC GGA TAC AGT         771
Ala Leu Gly Gly Asp Ile Asn Lys Val Leu Glu Lys Leu Gly Tyr Ser
            240                 245                 250

GGA GGT GAT TTA CTG GGC ATC TTA GAG AGC AGA GGA ATA AAG GCC CGG         819
Gly Gly Asp Leu Leu Gly Ile Leu Glu Ser Arg Gly Ile Lys Ala Arg
        255                 260                 265

ATA ACT CAC GTC GAC ACA GAG TCC TAC TTC ATT GTC CTC AGT ATA GCC         867
Ile Thr His Val Asp Thr Glu Ser Tyr Phe Ile Val Leu Ser Ile Ala
    270                 275                 280

TAT CCG ACG CTG TCC GAG ATT AAG GGG GTG ATT GTC CAC CGG CTA GAG         915
Tyr Pro Thr Leu Ser Glu Ile Lys Gly Val Ile Val His Arg Leu Glu
```

| | | | | | | | | | | | | | | | | |
|---|---|---|---|---|---|---|---|---|---|---|---|---|---|---|---|---|
| 285 | | | | | 290 | | | | | 295 | | | | | 300 | |
| GGG | GTC | TCG | TAC | AAT | ATA | GGC | TCT | CAA | GAG | TGG | TAT | ACC | ACT | GTG | CCC | 963 |
| Gly | Val | Ser | Tyr | Asn | Ile | Gly | Ser | Gln | Glu | Trp | Tyr | Thr | Thr | Val | Pro | |
| | | | | 305 | | | | 310 | | | | | 315 | | | |
| AAG | TAT | GTT | GCA | ACC | CAA | GGG | TAC | CTT | ATC | TCG | AAT | TTT | GAT | GAG | TCA | 1011 |
| Lys | Tyr | Val | Ala | Thr | Gln | Gly | Tyr | Leu | Ile | Ser | Asn | Phe | Asp | Glu | Ser | |
| | | | 320 | | | | 325 | | | | 330 | | | | | |
| TCG | TGT | ACT | TTC | ATG | CCA | GAG | GGG | ACT | GTG | TGC | AGC | CAA | AAT | GCC | TTG | 1059 |
| Ser | Cys | Thr | Phe | Met | Pro | Glu | Gly | Thr | Val | Cys | Ser | Gln | Asn | Ala | Leu | |
| | | 335 | | | | 340 | | | | | 345 | | | | | |
| TAC | CCG | ATG | AGT | CCT | CTG | CTC | CAA | GAA | TGC | CTC | CGG | GGG | TCC | ACC | AAG | 1107 |
| Tyr | Pro | Met | Ser | Pro | Leu | Leu | Gln | Glu | Cys | Leu | Arg | Gly | Ser | Thr | Lys | |
| | 350 | | | | 355 | | | | | 360 | | | | | | |
| TCC | TGT | GCT | CGT | ACA | CTC | GTA | TCC | GGG | TCT | TTT | GGG | AAC | CGG | TTC | ATT | 1155 |
| Ser | Cys | Ala | Arg | Thr | Leu | Val | Ser | Gly | Ser | Phe | Gly | Asn | Arg | Phe | Ile | |
| 365 | | | | | 370 | | | | 375 | | | | | | 380 | |
| TTA | TCA | CAA | GGG | AAC | CTA | ATA | GCC | AAT | TGT | GCA | TCA | ATC | CTC | TGC | AAG | 1203 |
| Leu | Ser | Gln | Gly | Asn | Leu | Ile | Ala | Asn | Cys | Ala | Ser | Ile | Leu | Cys | Lys | |
| | | | | 385 | | | | | 390 | | | | | 395 | | |
| TGT | TAC | ACA | ACA | GGA | ACG | ATC | ATT | AAT | CAA | GAC | CCT | GAC | AAG | ATC | CTA | 1251 |
| Cys | Tyr | Thr | Thr | Gly | Thr | Ile | Ile | Asn | Gln | Asp | Pro | Asp | Lys | Ile | Leu | |
| | | | 400 | | | | | 405 | | | | | 410 | | | |
| ACA | TAC | ATT | GCT | GCC | GAT | CAC | TGC | CCG | GTA | GTC | GAG | GTG | AAC | GGT | GTG | 1299 |
| Thr | Tyr | Ile | Ala | Ala | Asp | His | Cys | Pro | Val | Val | Glu | Val | Asn | Gly | Val | |
| | | 415 | | | | | 420 | | | | | 425 | | | | |
| ACC | ATC | CAA | GTC | GGG | AGC | AGG | AGG | TAT | CCG | GAC | GCG | GTG | TAC | CTG | CAC | 1347 |
| Thr | Ile | Gln | Val | Gly | Ser | Arg | Arg | Tyr | Pro | Asp | Ala | Val | Tyr | Leu | His | |
| | 430 | | | | | 435 | | | | | 440 | | | | | |
| AGA | ATT | GAC | CTC | GGT | CCT | CCC | ATA | TCA | TTG | GAG | AAG | TTG | GAC | GTA | GGG | 1395 |
| Arg | Ile | Asp | Leu | Gly | Pro | Pro | Ile | Ser | Leu | Glu | Lys | Leu | Asp | Val | Gly | |
| 445 | | | | | 450 | | | | | 455 | | | | | 460 | |
| ACA | AAT | CTG | GGG | AAT | GCA | ATT | GCT | AAG | CTG | GAG | GAT | GCC | AAG | GAA | TTG | 1443 |
| Thr | Asn | Leu | Gly | Asn | Ala | Ile | Ala | Lys | Leu | Glu | Asp | Ala | Lys | Glu | Leu | |
| | | | | 465 | | | | | 470 | | | | | 475 | | |
| CTG | GAG | TCA | TCG | GAC | CAG | ATA | TTG | AGG | AGT | ATG | AAA | GGT | TTA | TCG | AGC | 1491 |
| Leu | Glu | Ser | Ser | Asp | Gln | Ile | Leu | Arg | Ser | Met | Lys | Gly | Leu | Ser | Ser | |
| | | | 480 | | | | | 485 | | | | | 490 | | | |
| ACT | AGC | ATA | GTT | TAC | ATC | CTG | ATT | GCA | GTG | TGT | CTT | GGA | GGG | TTG | ATA | 1539 |
| Thr | Ser | Ile | Val | Tyr | Ile | Leu | Ile | Ala | Val | Cys | Leu | Gly | Gly | Leu | Ile | |
| | | 495 | | | | | 500 | | | | | 505 | | | | |
| GGG | ATC | CCC | GCT | TTA | ATA | TGT | TGC | TGC | AGG | GGG | CGT | TGT | AAC | AAA | AAG | 1587 |
| Gly | Ile | Pro | Ala | Leu | Ile | Cys | Cys | Cys | Arg | Gly | Arg | Cys | Asn | Lys | Lys | |
| | 510 | | | | | 515 | | | | | 520 | | | | | |
| GGA | GAA | CAA | GTT | GGT | ATG | TCA | AGA | CCA | GGC | CTA | AAG | CCT | GAT | CTT | ACA | 1635 |
| Gly | Glu | Gln | Val | Gly | Met | Ser | Arg | Pro | Gly | Leu | Lys | Pro | Asp | Leu | Thr | |
| 525 | | | | | 530 | | | | | 535 | | | | | 540 | |
| GGG | ACA | TCA | AAA | TCC | TAT | GTA | AGG | TCG | CTC | TGATCCCCTA | | CAACTCTTGA | | | | 1685 |
| Gly | Thr | Ser | Lys | Ser | Tyr | Val | Arg | Ser | Leu | | | | | | | |
| | | | | 545 | | | | 550 | | | | | | | | |
| AA | | | | | | | | | | | | | | | | 1687 |

( 2 ) INFORMATION FOR SEQ ID NO:20:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

| | | | | | | | | | | | | | | |
|---|---|---|---|---|---|---|---|---|---|---|---|---|---|---|
| Met | Gly | Leu | Lys | Val | Asn | Val | Phe | Ala | Ile | Phe | Met | Ala | Val | Leu | Leu |
| 1 | | | | 5 | | | | | 10 | | | | | 15 |
| Thr | Leu | Gln | Thr | Pro | Thr | Gly | Gln | Ile | His | Trp | Gly | Asn | Leu | Ser | Lys |
| | | | 20 | | | | 25 | | | | | 30 | | | |
| Ile | Gly | Val | Val | Gly | Ile | Gly | Ser | Ala | Ser | Tyr | Lys | Val | Met | Thr | Arg |
| | | 35 | | | | 40 | | | | | 45 | | | | |
| Ser | Ser | His | Gln | Ser | Leu | Val | Ile | Lys | Leu | Met | Pro | Asn | Ile | Thr | Leu |
| 50 | | | | | 55 | | | | | 60 | | | | | |
| Leu | Asn | Asn | Cys | Thr | Arg | Val | Glu | Ile | Ala | Glu | Tyr | Arg | Arg | Leu | Leu |
| 65 | | | | 70 | | | | 75 | | | | | | 80 | |
| Arg | Thr | Val | Leu | Glu | Pro | Ile | Arg | Asp | Ala | Leu | Asn | Ala | Met | Thr | Gln |
| | | | | 85 | | | | | 90 | | | | | 95 | |
| Asn | Ile | Arg | Pro | Val | Gln | Ser | Val | Ala | Ser | Ser | Arg | Arg | His | Lys | Arg |
| | | | 100 | | | | | 105 | | | | | 110 | | |
| Phe | Ala | Gly | Val | Val | Leu | Ala | Gly | Ala | Ala | Leu | Gly | Val | Ala | Thr | Ala |
| | | 115 | | | | | 120 | | | | | 125 | | | |
| Ala | Gln | Ile | Thr | Ala | Gly | Ile | Ala | Leu | His | Gln | Ser | Met | Leu | Asn | Ser |
| | 130 | | | | | 135 | | | | | 140 | | | | |
| Gln | Ala | Ile | Asp | Asn | Leu | Arg | Ala | Ser | Leu | Glu | Thr | Thr | Asn | Gln | Ala |
| 145 | | | | | 150 | | | | | 155 | | | | | 160 |
| Ile | Glu | Ala | Ile | Arg | Gln | Ala | Gly | Gln | Glu | Met | Ile | Leu | Ala | Val | Gln |
| | | | | 165 | | | | | 170 | | | | | 175 | |
| Gly | Val | Gln | Asp | Tyr | Ile | Asn | Asn | Glu | Leu | Ile | Pro | Ser | Met | Asn | Gln |
| | | | 180 | | | | | 185 | | | | | 190 | | |
| Leu | Ser | Cys | Asp | Leu | Ile | Gly | Gln | Lys | Leu | Gly | Leu | Lys | Leu | Leu | Arg |
| | | 195 | | | | | 200 | | | | | 205 | | | |
| Tyr | Tyr | Thr | Glu | Ile | Leu | Ser | Leu | Phe | Gly | Pro | Ser | Leu | Arg | Asp | Pro |
| | 210 | | | | | 215 | | | | | 220 | | | | |
| Ile | Ser | Ala | Glu | Ile | Ser | Ile | Gln | Ala | Leu | Ser | Tyr | Ala | Leu | Gly | Gly |
| 225 | | | | | 230 | | | | | 235 | | | | | 240 |
| Asp | Ile | Asn | Lys | Val | Leu | Glu | Lys | Leu | Gly | Tyr | Ser | Gly | Gly | Asp | Leu |
| | | | | 245 | | | | | 250 | | | | | 255 | |
| Leu | Gly | Ile | Leu | Glu | Ser | Arg | Gly | Ile | Lys | Ala | Arg | Ile | Thr | His | Val |
| | | | 260 | | | | | 265 | | | | | 270 | | |
| Asp | Thr | Glu | Ser | Tyr | Phe | Ile | Val | Leu | Ser | Ile | Ala | Tyr | Pro | Thr | Leu |
| | | 275 | | | | | 280 | | | | | 285 | | | |
| Ser | Glu | Ile | Lys | Gly | Val | Ile | Val | His | Arg | Leu | Glu | Gly | Val | Ser | Tyr |
| | 290 | | | | | 295 | | | | | 300 | | | | |
| Asn | Ile | Gly | Ser | Gln | Glu | Trp | Tyr | Thr | Thr | Val | Pro | Lys | Tyr | Val | Ala |
| 305 | | | | | 310 | | | | | 315 | | | | | 320 |
| Thr | Gln | Gly | Tyr | Leu | Ile | Ser | Asn | Phe | Asp | Glu | Ser | Ser | Cys | Thr | Phe |
| | | | | 325 | | | | | 330 | | | | | 335 | |
| Met | Pro | Glu | Gly | Thr | Val | Cys | Ser | Gln | Asn | Ala | Leu | Tyr | Pro | Met | Ser |
| | | | 340 | | | | | 345 | | | | | 350 | | |
| Pro | Leu | Leu | Gln | Glu | Cys | Leu | Arg | Gly | Ser | Thr | Lys | Ser | Cys | Ala | Arg |
| | | | 355 | | | | | 360 | | | | | 365 | | |
| Thr | Leu | Val | Ser | Gly | Ser | Phe | Gly | Asn | Arg | Phe | Ile | Leu | Ser | Gln | Gly |
| | | 370 | | | | | 375 | | | | | 380 | | | |
| Asn | Leu | Ile | Ala | Asn | Cys | Ala | Ser | Ile | Leu | Cys | Lys | Cys | Tyr | Thr | Thr |
| 385 | | | | | 390 | | | | | 395 | | | | | 400 |
| Gly | Thr | Ile | Ile | Asn | Gln | Asp | Pro | Asp | Lys | Ile | Leu | Thr | Tyr | Ile | Ala |
| | | | | 405 | | | | | 410 | | | | | 415 | |
| Ala | Asp | His | Cys | Pro | Val | Val | Glu | Val | Asn | Gly | Val | Thr | Ile | Gln | Val |
| | | | 420 | | | | | 425 | | | | | 430 | | |

Gly Ser Arg Arg Tyr Pro Asp Ala Val Tyr Leu His Arg Ile Asp Leu
        435             440                 445

Gly Pro Pro Ile Ser Leu Glu Lys Leu Asp Val Gly Thr Asn Leu Gly
    450             455                 460

Asn Ala Ile Ala Lys Leu Glu Asp Ala Lys Glu Leu Leu Glu Ser Ser
465             470             475                         480

Asp Gln Ile Leu Arg Ser Met Lys Gly Leu Ser Ser Thr Ser Ile Val
            485             490                     495

Tyr Ile Leu Ile Ala Val Cys Leu Gly Leu Ile Gly Ile Pro Ala
            500             505             510

Leu Ile Cys Cys Cys Arg Gly Arg Cys Asn Lys Lys Gly Glu Gln Val
        515             520             525

Gly Met Ser Arg Pro Gly Leu Lys Pro Asp Leu Thr Gly Thr Ser Lys
    530             535                 540

Ser Tyr Val Arg Ser Leu
545             550

( 2 ) INFORMATION FOR SEQ ID NO:21:

( i ) SEQUENCE CHARACTERISTICS:
        ( A ) LENGTH: 617 amino acids
        ( B ) TYPE: amino acid
        ( D ) TOPOLOGY: linear ( i i ) MOLECULE TYPE: protein ( v i ) ORIGINAL SOURCE:
        ( B ) STRAIN: consensus HA polypeptide ( i x ) FEATURE:
        ( A ) NAME/KEY: Modified-site
        ( B ) LOCATION: 4
        ( D ) OTHER INFORMATION: /note="Xaa denotes Gln or His"

( i x ) FEATURE:
        ( A ) NAME/KEY: Modified-site
        ( B ) LOCATION: 19
        ( D ) OTHER INFORMATION: /note="Xaa denotes Lys or Arg"

( i x ) FEATURE:
        ( A ) NAME/KEY: Modified-site
        ( B ) LOCATION: 176
        ( D ) OTHER INFORMATION: /note="Xaa denotes Thr, Val or Ala"

( i x ) FEATURE:
        ( A ) NAME/KEY: Modified-site
        ( B ) LOCATION: 235
        ( D ) OTHER INFORMATION: /note="Xaa denotes Glu or Gly"

( i x ) FEATURE:
        ( A ) NAME/KEY: Modified-site
        ( B ) LOCATION: 295
        ( D ) OTHER INFORMATION: /note="Xaa denotes Lys or Arg"

( i x ) FEATURE:
        ( A ) NAME/KEY: Modified-site
        ( B ) LOCATION: 303
        ( D ) OTHER INFORMATION: /note="Xaa denotes Glu or Gly"

( i x ) FEATURE:
        ( A ) NAME/KEY: Modified-site
        ( B ) LOCATION: 305
        ( D ) OTHER INFORMATION: /note="Xaa represents Ser or Phe"

( i x ) FEATURE:
        ( A ) NAME/KEY: Modified-site
        ( B ) LOCATION: 306
        ( D ) OTHER INFORMATION: /note="Xaa denotes Ile or Val"

( i x ) FEATURE:

( A ) NAME/KEY: Modified-site
( B ) LOCATION: 308
( D ) OTHER INFORMATION: /note="Xaa denotes Ile or Val"

( i x ) FEATURE:
( A ) NAME/KEY: Modified-site
( B ) LOCATION: 320
( D ) OTHER INFORMATION: /note="Xaa denotes Gln or Arg"

( i x ) FEATURE:
( A ) NAME/KEY: Modified-site
( B ) LOCATION: 339
( D ) OTHER INFORMATION: /note="Xaa denotes Leu or Phe"

( i x ) FEATURE:
( A ) NAME/KEY: Modified-site
( B ) LOCATION: 348
( D ) OTHER INFORMATION: /note="Xaa denotes Arg or Lys"

( i x ) FEATURE:
( A ) NAME/KEY: Modified-site
( B ) LOCATION: 367
( D ) OTHER INFORMATION: /note="Xaa denotes Val or Ile"

( i x ) FEATURE:
( A ) NAME/KEY: Modified-site
( B ) LOCATION: 389
( D ) OTHER INFORMATION: /note="Xaa denotes Lys or Arg"

( i x ) FEATURE:
( A ) NAME/KEY: Modified-site
( B ) LOCATION: 390
( D ) OTHER INFORMATION: /note="Xaa denotes Ile or Asn"

( i x ) FEATURE:
( A ) NAME/KEY: Modified-site
( B ) LOCATION: 446
( D ) OTHER INFORMATION: /note="Xaa denotes Ser or Thr"

( i x ) FEATURE:
( A ) NAME/KEY: Modified-site
( B ) LOCATION: 451
( D ) OTHER INFORMATION: /note="Xaa denotes Val or Glu"

( i x ) FEATURE:
( A ) NAME/KEY: Modified-site
( B ) LOCATION: 485
( D ) OTHER INFORMATION: /note="Xaa denotes Val or Ile"

( i x ) FEATURE:
( A ) NAME/KEY: Modified-site
( B ) LOCATION: 501
( D ) OTHER INFORMATION: /note="Xaa denotes Pro or Ser"

( i x ) FEATURE:
( A ) NAME/KEY: Modified-site
( B ) LOCATION: 544
( D ) OTHER INFORMATION: /note="Xaa denotes Ser or Asn"

( i x ) FEATURE:
( A ) NAME/KEY: Modified-site
( B ) LOCATION: 546
( D ) OTHER INFORMATION: /note="Xaa denotees Ser or Gly"

( i x ) FEATURE:
( A ) NAME/KEY: Modified-site
( B ) LOCATION: 559
( D ) OTHER INFORMATION: /note="Xaa denotes Ile or Val"

( i x ) FEATURE:
( A ) NAME/KEY: Modified-site
( B ) LOCATION: 560
( D ) OTHER INFORMATION: /note="Xaa denotes Lys or Arg"

( i x ) FEATURE:
( A ) NAME/KEY: Modified-site
( B ) LOCATION: 562
( D ) OTHER INFORMATION: /note="Xaa denotes Val, Ile or
        Phe"

( i x ) FEATURE:
    ( A ) NAME/KEY: Modified-site
    ( B ) LOCATION: 593
    ( D ) OTHER INFORMATION: /note="Xaa denotes His or Tyr"

( i x ) FEATURE:
    ( A ) NAME/KEY: Modified-site
    ( B ) LOCATION: 616
    ( D ) OTHER INFORMATION: /note="Xaa denotes Arg or Ser"

( x i ) SEQUENCE DESCRIPTION: SEQ ID NO:21:

```
Met Ser Pro Xaa Arg Asp Arg Ile Asn Ala Phe Tyr Lys Asp Asn Pro
 1               5                  10                  15

His Pro Xaa Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
            35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Phe Ile Ser Asp Lys Ile Lys Phe Leu Asn Pro Asp
            115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Ala Arg Xaa
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
    195                 200                 205

Tyr Leu Ser Arg Gly Tyr Asn Val Ser Ser Ile Val Thr Met Thr Ser
    210                 215                 220

Gln Gly Met Tyr Gly Gly Thr Tyr Leu Val Xaa Lys Pro Asn Leu Ser
225                 230                 235                 240

Ser Lys Gly Ser Glu Leu Ser Gln Leu Ser Met His Arg Val Phe Glu
            245                 250                 255

Val Gly Val Ile Arg Asn Pro Gly Leu Gly Ala Pro Val Phe His Met
            260                 265                 270

Thr Asn Tyr Phe Glu Gln Pro Val Ser Asn Asp Phe Ser Asn Cys Met
    275                 280                 285

Val Ala Leu Gly Glu Leu Xaa Phe Ala Ala Leu Cys His Arg Xaa Asp
    290                 295                 300

Xaa Xaa Thr Xaa Pro Tyr Gln Gly Ser Gly Lys Gly Val Ser Phe Xaa
305                 310                 315                 320

Leu Val Lys Leu Gly Val Trp Lys Ser Pro Thr Asp Met Gln Ser Trp
            325                 330                 335

Val Pro Xaa Ser Thr Asp Asp Pro Val Ile Asp Xaa Leu Tyr Leu Ser
            340                 345                 350

Ser His Arg Gly Val Ile Ala Asp Asn Gln Ala Lys Trp Ala Xaa Pro
    355                 360                 365
```

| | | | | | | | | | | | | | | |
|---|---|---|---|---|---|---|---|---|---|---|---|---|---|---|
| Thr | Thr 370 | Arg | Thr | Asp | Asp 375 | Lys | Leu | Arg | Met | Thr 380 | Cys | Phe | Gln | Gln |
| Ala 385 | Cys | Lys | Gly | Xaa | Xaa 390 | Gln | Ala | Leu | Cys | Glu 395 | Asn | Pro | Glu | Trp | Ala 400 |
| Pro | Leu | Lys | Asp | Asn 405 | Arg | Ile | Pro | Ser | Tyr 410 | Gly | Val | Leu | Ser | Val 415 | Asn |
| Leu | Ser | Leu | Thr 420 | Val | Glu | Leu | Lys | Ile 425 | Lys | Ile | Ala | Ser | Gly 430 | Phe | Gly |
| Pro | Leu | Ile 435 | Thr | His | Gly | Ser | Gly 440 | Met | Asp | Leu | Tyr | Lys 445 | Xaa | Asn | His |
| Asn | Asn 450 | Xaa | Tyr | Trp | Leu | Thr 455 | Ile | Pro | Pro | Met | Lys 460 | Asn | Leu | Ala | Leu |
| Gly 465 | Val | Ile | Asn | Thr | Leu 470 | Glu | Trp | Ile | Pro | Arg 475 | Phe | Lys | Val | Ser | Pro 480 |
| Asn | Leu | Phe | Thr | Xaa 485 | Pro | Ile | Lys | Glu | Ala 490 | Gly | Glu | Asp | Cys | His 495 | Ala |
| Pro | Thr | Tyr | Leu | Xaa 500 | Ala | Glu | Val | Asp | Gly 505 | Asp | Val | Lys | Leu 510 | Ser | Ser |
| Asn | Leu | Val | Ile 515 | Leu | Pro | Gly | Gln | Asp 520 | Leu | Gln | Tyr | Val 525 | Leu | Ala | Thr |
| Tyr | Asp 530 | Thr | Ser | Arg | Val | Glu 535 | His | Ala | Val | Val | Tyr 540 | Tyr | Val | Tyr | Xaa |
| Pro 545 | Xaa | Arg | Ser | Phe | Ser 550 | Tyr | Phe | Tyr | Pro | Phe 555 | Arg | Leu | Pro | Xaa | Xaa 560 |
| Gly | Xaa | Pro | Ile | Glu 565 | Leu | Gln | Val | Glu | Cys 570 | Phe | Thr | Trp | Asp | Gln 575 | Lys |
| Leu | Trp | Cys | Arg 580 | His | Phe | Cys | Val | Leu 585 | Ala | Asp | Ser | Glu | Ser 590 | Gly | Gly |
| Xaa | Ile | Thr 595 | His | Ser | Gly | Met | Val 600 | Gly | Met | Gly | Val | Ser 605 | Cys | Thr | Val |
| Thr | Arg 610 | Glu | Asp | Gly | Thr | Asn 615 | Xaa | Arg | | | | | | | |

( 2 ) INFORMATION FOR SEQ ID NO:22:

( i ) SEQUENCE CHARACTERISTICS:
        ( A ) LENGTH: 550 amino acids
        ( B ) TYPE: amino acid
        ( D ) TOPOLOGY: linear ( i i ) MOLECULE TYPE: peptide ( v i ) ORIGINAL SOURCE:
        ( B ) STRAIN: consensus fusion polypeptide ( x i ) SEQUENCE DESCRIPTION: SEQ ID NO:22:

| | | | | | | | | | | | | | | |
|---|---|---|---|---|---|---|---|---|---|---|---|---|---|---|
| Val 1 | Gly | Leu | Lys | Val 5 | Asn | Val | Phe | Ala | Ile 10 | Phe | Met | Ala | Val | Leu 15 | Leu |
| Thr | Leu | Gln | Thr 20 | Pro | Thr | Gly | Gln | Ile 25 | His | Trp | Gly | Asn | Leu 30 | Ser | Lys |
| Ile | Gly | Val | Val 35 | Gly | Ile | Gly | Ser 40 | Ala | Ser | Tyr | Lys | Val 45 | Met | Thr | Arg |
| Ser | Ser 50 | His | Gln | Ser | Leu | Val 55 | Ile | Lys | Leu | Met | Pro 60 | Asn | Ile | Thr | Leu |
| Leu 65 | Asn | Asn | Cys | Thr | Arg 70 | Val | Glu | Ile | Ala | Glu 75 | Tyr | Arg | Arg | Leu | Leu 80 |
| Arg | Thr | Val | Leu | Glu | Pro | Ile | Arg | Asp | Ala | Leu | Asn | Ala | Met | Thr | Gln |

-continued

|   |   |   |   | 85 |   |   |   | 90 |   |   |   | 95 |   |
|---|---|---|---|---|---|---|---|---|---|---|---|---|---|
| Asn | Ile | Arg | Pro<br>100 | Val | Gln | Ser | Val<br>105 | Ala | Ser | Ser | Arg | Arg<br>110 | His | Lys | Arg |
| Phe | Ala | Gly<br>115 | Val | Val | Leu | Ala<br>120 | Gly | Ala | Ala | Leu | Gly<br>125 | Val | Ala | Thr | Ala |
| Ala | Gln<br>130 | Ile | Thr | Ala | Gly<br>135 | Ile | Ala | Leu | His | Gln<br>140 | Ser | Met | Leu | Asn | Ser |
| Gln<br>145 | Ala | Ile | Asp | Asn<br>150 | Leu | Arg | Ala | Ser | Leu<br>155 | Glu | Thr | Thr | Asn | Gln | Ala<br>160 |
| Ile | Glu | Ala | Ile | Arg<br>165 | Gln | Ala | Gly | Gln | Glu<br>170 | Met | Ile | Leu | Ala | Val<br>175 | Gln |
| Gly | Val | Gln | Asp<br>180 | Tyr | Ile | Asn | Asn | Glu<br>185 | Leu | Ile | Pro | Ser | Met<br>190 | Asn | Gln |
| Leu | Ser | Cys<br>195 | Asp | Leu | Ile | Gly | Gln<br>200 | Lys | Leu | Gly | Leu | Lys<br>205 | Leu | Leu | Arg |
| Tyr | Tyr | Thr<br>210 | Glu | Ile | Leu | Ser<br>215 | Leu | Phe | Gly | Pro | Ser<br>220 | Leu | Arg | Asp | Pro |
| Ile<br>225 | Ser | Ala | Glu | Ile | Ser<br>230 | Ile | Gln | Ala | Leu | Ser<br>235 | Tyr | Ala | Leu | Gly | Gly<br>240 |
| Asp | Ile | Asn | Lys | Val<br>245 | Leu | Glu | Lys | Leu | Gly<br>250 | Tyr | Ser | Gly | Gly | Asp<br>255 | Leu |
| Leu | Gly | Ile | Leu<br>260 | Glu | Ser | Arg | Gly | Ile<br>265 | Lys | Ala | Arg | Ile | Thr<br>270 | His | Val |
| Asp | Thr | Glu<br>275 | Ser | Tyr | Phe | Ile | Val<br>280 | Leu | Ser | Ile | Ala | Tyr<br>285 | Pro | Thr | Leu |
| Ser | Glu<br>290 | Ile | Lys | Gly | Val | Ile<br>295 | Val | His | Arg | Leu | Glu<br>300 | Gly | Val | Ser | Tyr |
| Asn<br>305 | Ile | Gly | Ser | Gln | Glu<br>310 | Trp | Tyr | Thr | Thr | Val<br>315 | Pro | Lys | Tyr | Val | Ala<br>320 |
| Thr | Gln | Gly | Tyr | Leu<br>325 | Ile | Ser | Asn | Phe | Asp<br>330 | Glu | Ser | Ser | Cys<br>335 | Thr | Phe |
| Met | Pro | Glu | Gly<br>340 | Thr | Val | Cys | Ser | Gln<br>345 | Asn | Ala | Leu | Tyr | Pro<br>350 | Met | Ser |
| Pro | Leu | Leu<br>355 | Gln | Glu | Cys | Leu | Arg<br>360 | Gly | Ser | Thr | Lys | Ser<br>365 | Cys | Ala | Arg |
| Thr | Leu<br>370 | Val | Ser | Gly | Ser | Phe<br>375 | Gly | Asn | Arg | Phe | Ile<br>380 | Leu | Ser | Gln | Gly |
| Asn<br>385 | Leu | Ile | Ala | Asn | Cys<br>390 | Ala | Ser | Ile | Leu | Cys<br>395 | Lys | Cys | Tyr | Thr | Thr<br>400 |
| Gly | Thr | Ile | Ile | Asn<br>405 | Gln | Asp | Pro | Asp | Lys<br>410 | Ile | Leu | Thr | Tyr | Ile<br>415 | Ala |
| Ala | Asp | His | Cys<br>420 | Pro | Val | Val | Glu | Val<br>425 | Asn | Gly | Val | Thr | Ile<br>430 | Gln | Val |
| Gly | Ser | Arg<br>435 | Arg | Tyr | Pro | Asp | Ala<br>440 | Val | Tyr | Leu | His | Arg<br>445 | Ile | Asp | Leu |
| Gly | Pro<br>450 | Pro | Ile | Ser | Leu | Glu<br>455 | Lys | Leu | Asp | Val | Gly<br>460 | Thr | Asn | Leu | Gly |
| Asn<br>465 | Ala | Ile | Ala | Lys | Leu<br>470 | Glu | Asp | Ala | Lys | Glu<br>475 | Leu | Leu | Glu | Ser | Ser<br>480 |
| Asp | Gln | Ile | Leu | Arg<br>485 | Ser | Met | Lys | Gly | Leu<br>490 | Ser | Ser | Thr | Ser | Ile<br>495 | Val |
| Tyr | Ile | Leu | Ile<br>500 | Ala | Val | Cys | Leu | Gly<br>505 | Gly | Leu | Ile | Gly | Ile<br>510 | Pro | Ala |

| | | | | | | | | | | | | | |
|---|---|---|---|---|---|---|---|---|---|---|---|---|---|
| Leu | Ile | Cys 515 | Cys | Cys | Arg | Gly | Arg 520 | Cys | Asn | Lys | Lys | Gly 525 | Glu | Gln | Val |
| Gly | Met 530 | Ser | Arg | Pro | Gly | Leu 535 | Lys | Pro | Asp | Leu | Thr 540 | Gly | Thr | Ser | Lys |
| Ser 545 | Tyr | Val | Arg | Ser | Leu 550 | | | | | | | | |